(12) United States Patent
Hanon et al.

(10) Patent No.: US 7,939,084 B1
(45) Date of Patent: May 10, 2011

(54) VACCINE AGAINST VARICELLA ZOSTER VIRUS

(75) Inventors: Emmanuel Jules Hanon, Rixensart (BE); Jean Stephenne, Rixensart (BE)

(73) Assignee: GlaxoSmithKline Biologicals, s.a., Rixensart (BE)

( * ) Notice: Subject to any disclaimer, the term of this patent is extended or adjusted under 35 U.S.C. 154(b) by 0 days.

(21) Appl. No.: 12/986,928

(22) Filed: Jan. 7, 2011

Related U.S. Application Data

(63) Continuation of application No. 12/784,296, filed on May 20, 2010, which is a continuation of application No. 11/817,175, filed as application No. PCT/EP2006/002070 on Mar. 1, 2006.

(30) Foreign Application Priority Data

Mar. 3, 2005 (EP) ..................................... 0504436

(51) Int. Cl.
*A61K 39/245* (2006.01)

(52) U.S. Cl. ......................................... 424/230.1; 435/6
(58) Field of Classification Search ........................ None
See application file for complete search history.

(56) References Cited

FOREIGN PATENT DOCUMENTS
WO        WO 00/43527 A   *   7/2000

OTHER PUBLICATIONS

Haumont et al, Virus Research, 1996, vol. 40, pp. 199-204.*

* cited by examiner

*Primary Examiner* — Ali R. Salimi
(74) *Attorney, Agent, or Firm* — Convergent Law Group LLP

(57) ABSTRACT

Use of an immunogenic composition comprising VZV gE, or immunogenic fragment thereof, and a TH-1 adjuvant in the preparation of a medicament for the prevention or amelioration of shingles and/or post herpetic neuralgia. Compositions comprising a truncated VZV gE antigen and an adjuvant containing QS21, cholesterol and 3D MPL are also claimed.

17 Claims, 6 Drawing Sheets

Figure 1

```
  1 MGTVNKPVVG VLMGFGIITG TLRITNPVRA SVLRYDDFHI DEDKLDTNSV YEPYYHSDHA
 61 ESSWVNRGES SRKAYDHNSP YIWPRNDYDG FLENAHEHHG VYNQGRGIDS GERLMQPTQM
121 SAQEDLGDDT GIHVIPTLNG DDRHKIVNVD QRQYGDVFKG DLNPKPQGQR LIEVSVEENH
181 PFTLRAPIQR IYGVRYTETW SFLPSLTCTG DAAPAIQHIC LKHTTCFQDV VVDVDCAENT
241 KEDQLAEISY RFQGKKEADQ PWIVVNTSTL FDELELDPPE IEPGVLKVLR TEKQYLGVYI
301 WNMRGSDGTS TYATFLVTWK GDEKTRNPTP AVTPQPRGAE FHMWNYHSHV FSVGDTFSLA
361 MHLQYKIHEA PFDLLLEWLY VPIDPTCQPM RLYSTCLYHP NAPQCLSHMN SGCTFTSPHL
421 AQRVASTVYQ NCEHADNYTA YCLGISHMEP SFGLILHDGG TTLKFVDTPE SLSGLYVFVV
481 YFNGHVEAVA YTVVSTVDHF VNAIEERGFP PTAGQPPATT KPKEITPVNP GTSPLIRYAA
541 WTGGLA
```

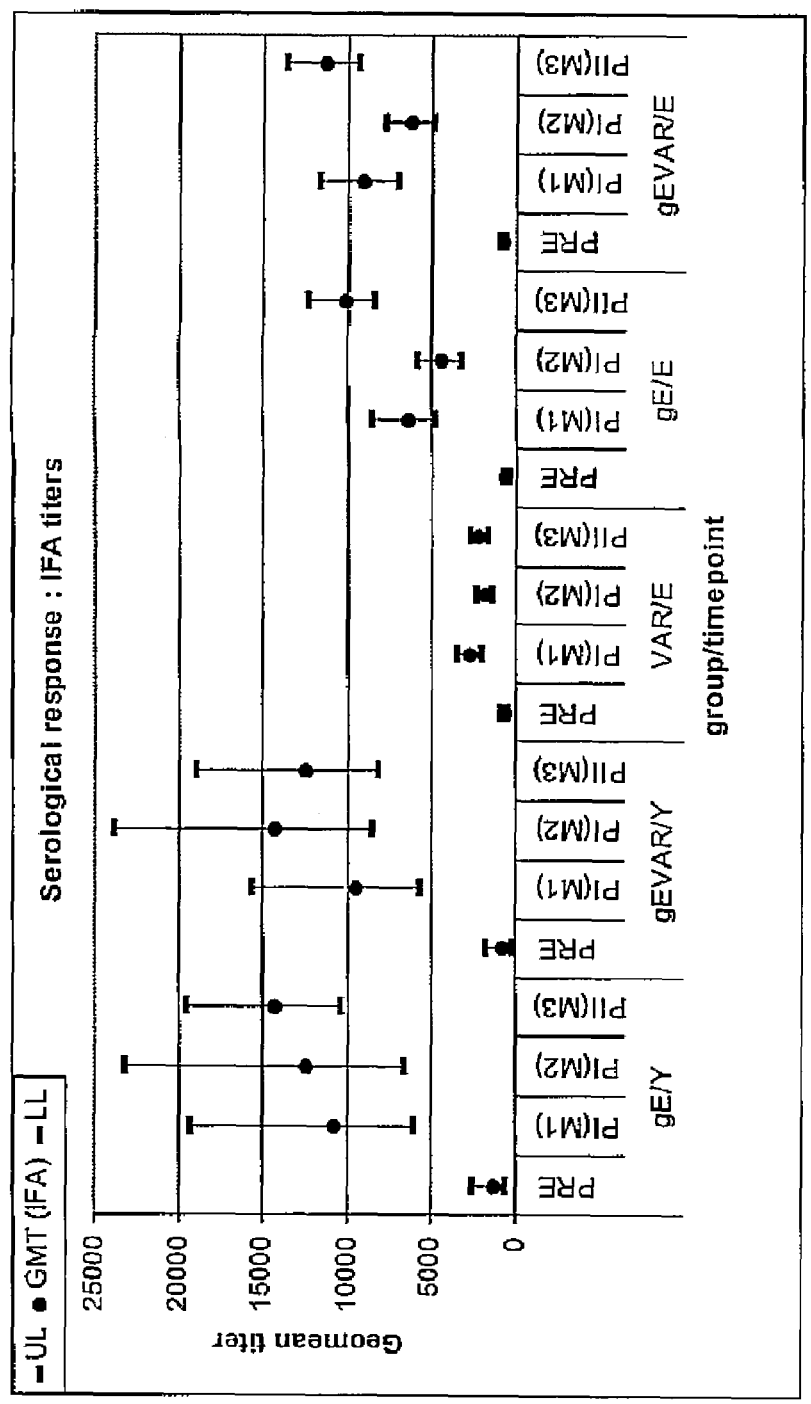
Fig 2  CRD-004 study : humoral results

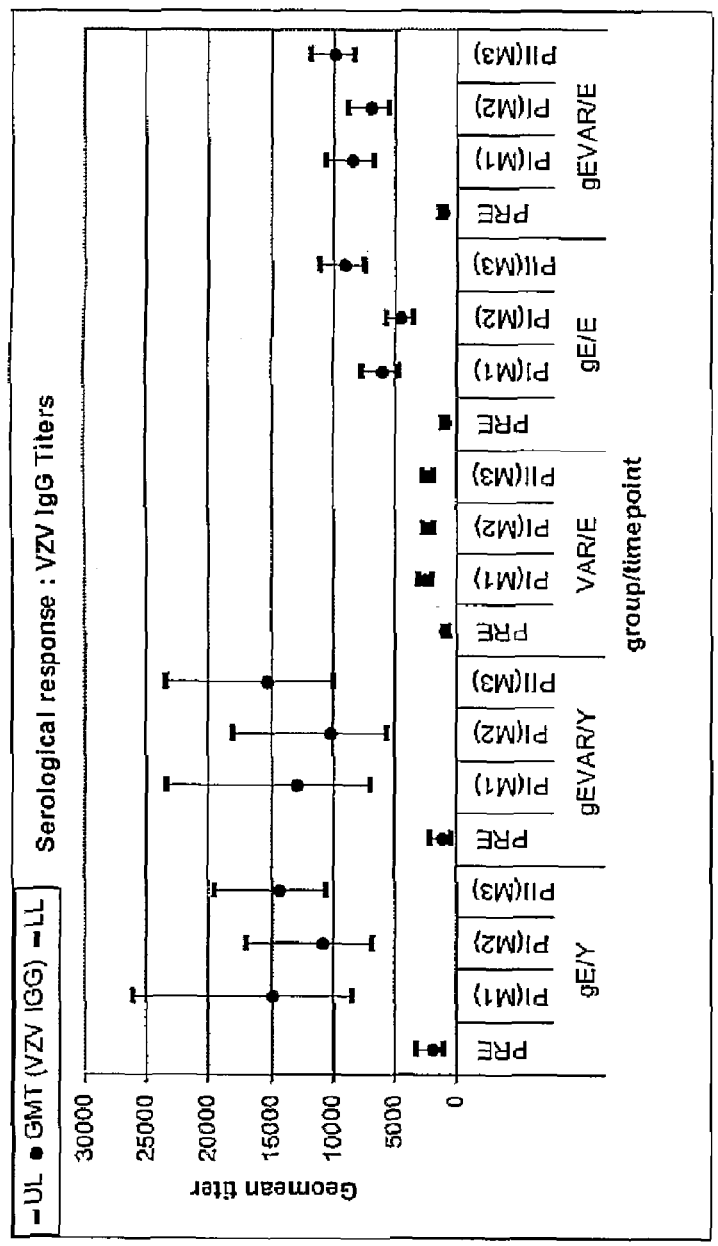
Fig 3  CRD-004 study : humoral results

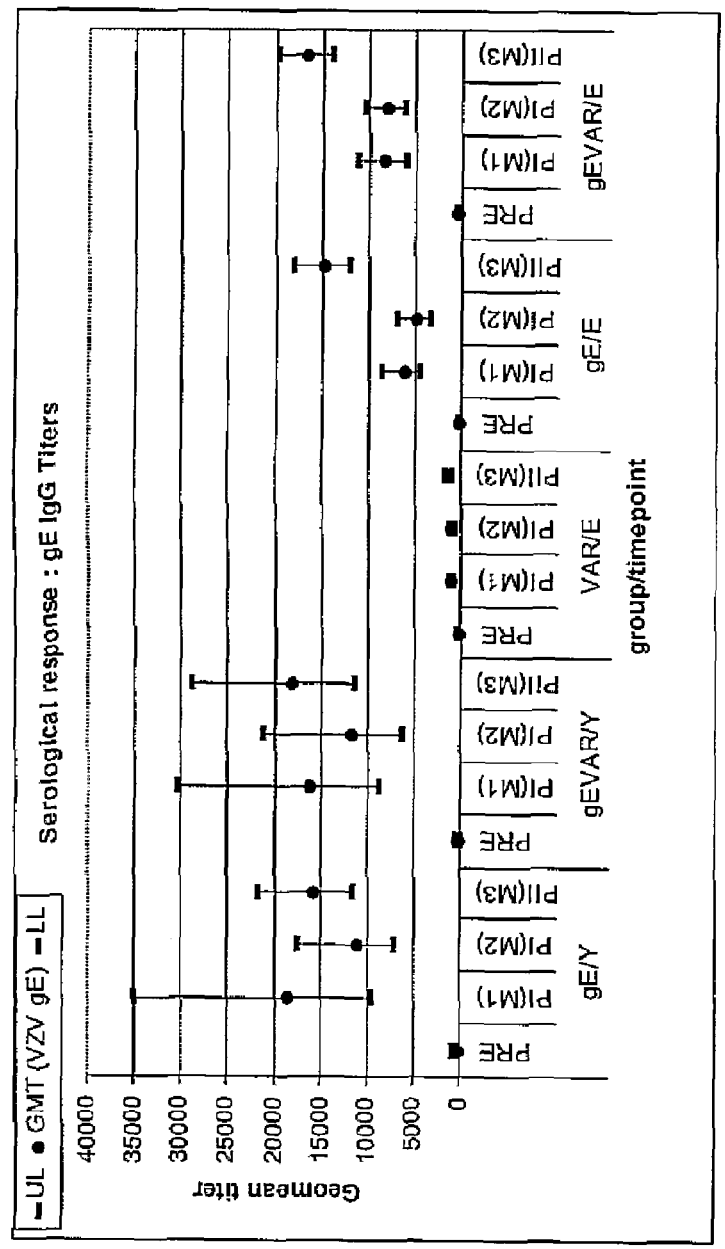
Fig 4 CRD-004 study : humoral results

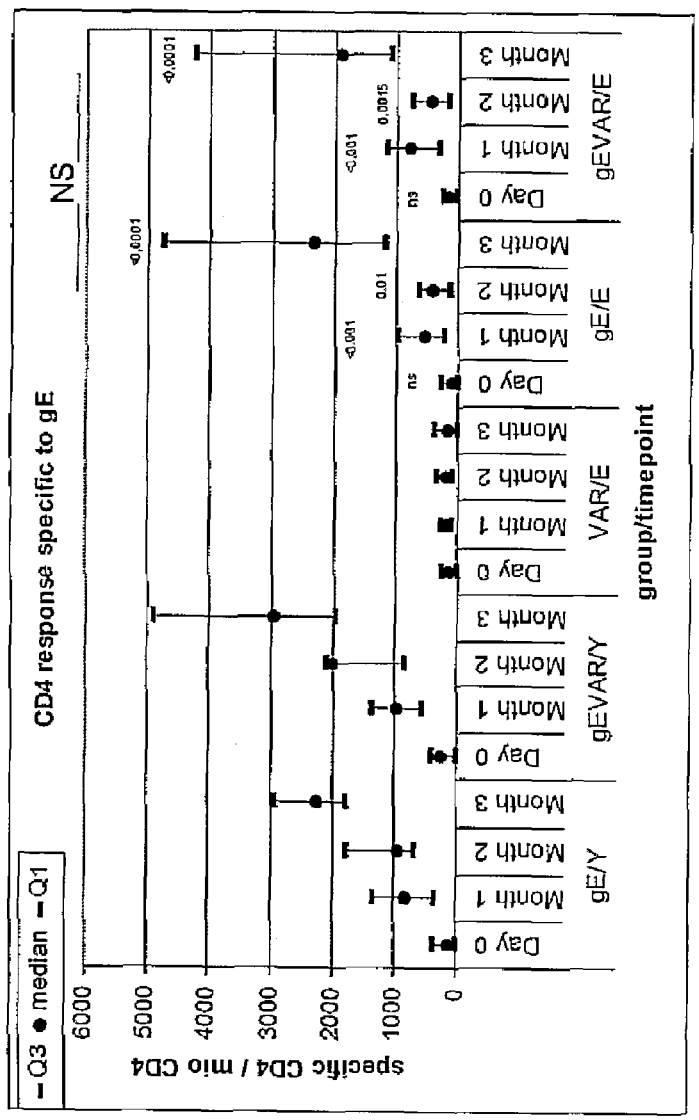
Fig 5  CRD-004 study : CMI results (ICS)

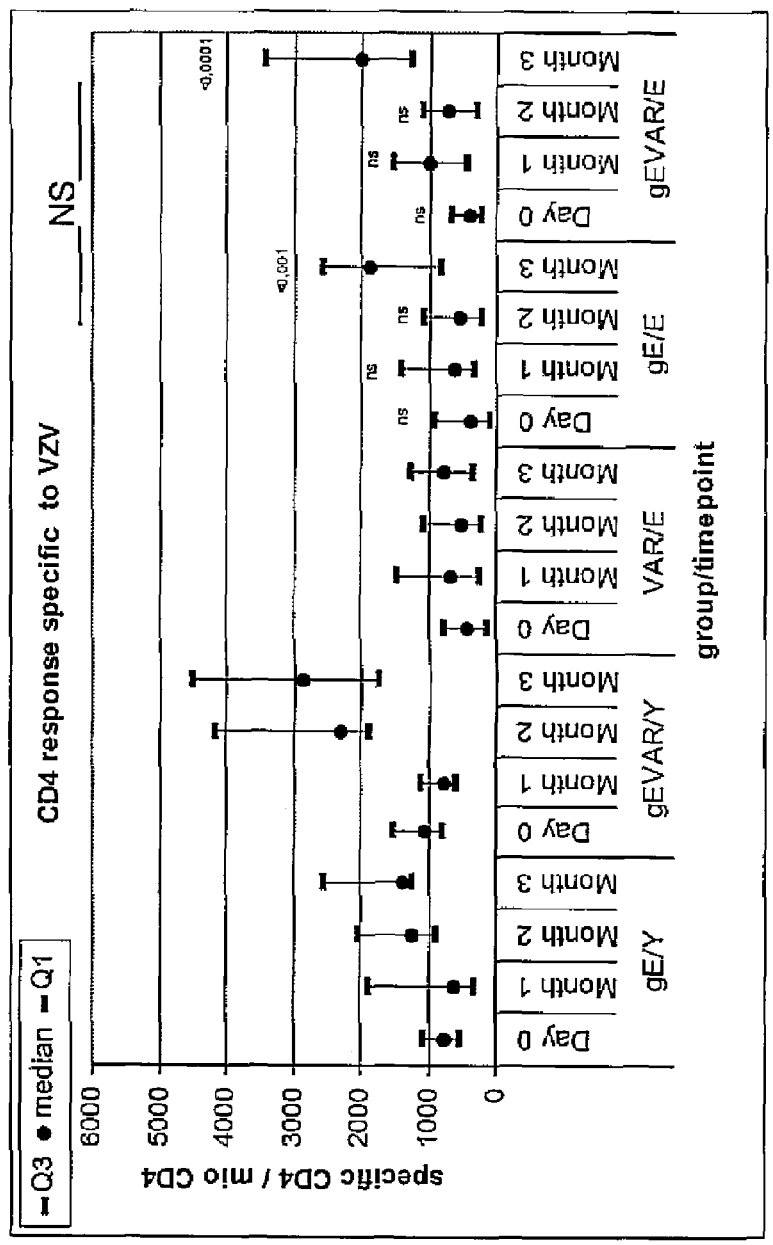
Fig 6  CRD-004 study : CMI results (ICS)

VACCINE AGAINST VARICELLA ZOSTER VIRUS

This application claims priority from co-pending U.S. application Ser. No. 12/784,296 filed May 20, 2010, and U.S. application Ser. No. 11/817,175, filed Aug. 27, 2007, which claims priority to GB application 0504436.7, filed Mar. 3, 2005, and EPO PCT/EP2006/002070 filed Mar. 1, 2006, each of which is hereby incorporated by reference in its entirety.

This invention relates to compositions capable of inducing an immune response against Varicella-Zoster Virus.

Varicella-Zoster Virus (VZV) is a human herpes virus which is the etiological agent of chicken pox (varicella) and shingles (zoster). Varicella results from an initial, or primary infection, usually contracted during childhood which is relatively benign. However, for adults who were not exposed to varicella during childhood, and occasionally to individuals who are immunocomprised, VZV can be life-threatening. Similarly, a VZV infection can be life-threatening to neonates, for the virus is capable of crossing the placenta. With direct contact, varicella is known to be a highly transmissible infectious disease.

Like most Herpes-Viruses, VZV has a tendency to infect some cells in which its development is arrested. After a variable latent period, the Varicella-Zoster (VZ) virus can be released to initiate infection in other cells. This reactivation of the VZ virus causes an estimated 5 million cases of zoster annually (Plotkin et al., Postgrad Med J 61: 155-63 (1985)). Zoster is characterized by inflammation of the cerebral ganglia and peripheral nerves, and it is associated with acute pain.

It has been shown that humans vaccinated with attenuated strains of VZV have received protective immunity from VZV infections (Arbeter et al., J. Pediatr 100 886-93 (1982) and Brunell et al., Lancet ii: 1069-72 (1982)). In particular the OKA strain of VZV has been used in trials for the prevention of herpes zoster and post herpetic neuralgia. The OKA strain has also been used in the preparation of vaccines for chickenpox for many years and is well characterised—for example see EP651789 and references therein.

A large clinical trial using the OKA strain for the zoster indication has been published in The New England Journal of Medicine 2005, number 22, Volume 352:2271-2284 (M. N. Oxman et al).

There is still a need for improved vaccines against herpes zoster and related disorders such as post herpetic neuralgia (PHN).

STATEMENT OF INVENTION

First Aspect

The present invention provides in a first aspect an immunogenic composition comprising a VZV antigen or immunogenic derivative thereof in combination with a live attenuated VZV or whole inactivated VZV.

The invention further relates to a vaccine composition comprising a VZV antigen or immunogenic derivative thereof in combination with a live attenuated VZV or whole inactivated VZV.

The invention further relates to a method of preventing and/or decreasing the severity of herpes zoster and/or post herpetic neuralgia (PHN) comprising delivering to an individual an immunogenic composition comprising a VZV antigen or immunogenic derivative thereof in combination with a live attenuated VZV or whole inactivated VZV.

In a further embodiment the invention relates to a method of preventing and/or decreasing the severity of herpes zoster and/or post herpetic neuralgia, the method comprising sequential or concomitant delivery to an individual of a VZV antigen or immunogenic derivative thereof and a live attenuated VZV or whole inactivated VZV.

In a still further embodiment the invention relates to a kit comprising a live attenuated VZV or whole inactivated VZV and, separately, a VZV antigen or immunogenic derivative thereof, the components suitable for concomitant or sequential delivery, or for mixing as a single composition prior to delivery.

The invention also relates to a method for the manufacture of an immunogenic composition, the method comprising combining a live attenuated VZV or whole inactivated VZV with a VZV antigen or immunogenic derivative thereof.

The invention further relates to use of a live attenuated VZV strain or whole inactivated VZV and a VZV antigen or immunogenic derivative thereof in the preparation of an immunogenic composition for preventing and/or decreasing the severity of herpes zoster and/or post herpetic neuralgia.

Second Aspect

In a second aspect the invention relates to an immunogenic composition and/or vaccine comprising gE or an immunogenic derivative or immunogenic fragment thereof in combination with a TH1-adjuvant.

The invention also relates to use of a composition comprising gE or an immunogenic derivative or immunogenic fragment thereof in combination with a TH1-adjuvant, in the preparation of a medicament for the prevention or amelioration of herpes zoster reactivation and/or post herpetic neuralgia.

The invention also relates to a method for the prevention or amelioration of herpes zoster reactivation and/or post herpetic neuralgia, the method comprising delivering to an individual in need thereof an immunogenic composition or vaccine comprising gE or an immunogenic derivative or immunogenic fragment thereof in combination with a TH1-adjuvant.

FIGURES

FIG. 1 discloses the sequence of a truncated VZV gE.

FIGS. 2-4 disclose humoral responses obtained in human clinical trials using compositions of the invention.

FIGS. 5 and 6 disclose cell mediated immunity obtained in human clinical trials using compositions of the invention.

DETAILED DESCRIPTION

In its broadest aspect the present invention relates to compositions and regimes as described herein for provoking an immune response to VZV. In one aspect the immune response generated by exposure to such compositions is suitably reproducibly higher and statistically significant when compared to that obtained in individuals who have received no exposure to the compositions of the invention. The immune response may be assessed by analysis of any one or more aspects of CMI response and/or antibody responses using any of the techniques outlined below.

In another aspect the invention relates to approaches for preventing and/or decreasing the severity of herpes zoster and/or post herpetic neuralgia (PHN). For the avoidance of doubt, the invention relates in one aspect to use in the prevention of the incidence of zoster. Where zoster does occur then the severity of the reactivation of zoster is suitably reduced compared with an unvaccinated control (amelioration of zoster). In a further aspect, where zoster does occur, the invention relates to use in the prevention of the incidence of PHN. In a further aspect where PHN does occur then the severity of the PHN is suitably reduced compared with an unvaccinated control (amelioration of PHN). Reduction in severity can suitably be assessed by a reduction in the pain caused by zoster or PHN, for example, using known measures of burden of pain (e.g. Coplan et al J Pain 2004; 5 (6) 344-56). Reduction in severity can also be assessed by other criteria such as duration of zoster or PHN, proportion of body area affected by zoster or PHN; or the site of zoster/PHN.

The above statements relate to all aspects of the invention.

Where a live attenuated strain is used in the first aspect of the invention, then in one aspect the live attenuated VZV strain is the OKA strain, a strain well known in the art, for example as disclosed in Arbeter et al. (Journal of Pediatrics, vol 100, No 6, p 886 ff), WO9402596, and references therein, such as U.S. Pat. No. 3,985,615, all incorporated herein by reference. Any other suitable live attenuated strain may also be used in the invention. For example, the Varilrix™ and Varivax™ strains are both appropriate and commercially available and could be employed in the invention.

Whole inactivated VZV strains, such as inactivated VZV OKA are also suitable for use in the present invention.

The VZV antigen for use in the invention may be any suitable VZV antigen or immunogenic derivative thereof, suitably being a purified VZV antigen. In one aspect the antigen or derivative is one that is able to elicit, when delivered in combination, concomitantly or sequentially with a live attenuated VZV strain or whole inactivated VZV, an immune response which is improved over that elicited by the live attenuated strain/whole inactivated strain alone or by the VZV antigen alone. Such a response may be, for example, improved in terms of one or more of the magnitude of immune response, duration of immune response, the number or % or responders, or the breadth of response (e.g. the range of antibody or T cell responses detected), or may provide an improvement at the clinical level in terms of incidence, reduction of pain or symptoms. Improvements in the immune response can be assessed by, for example, antibody levels or cell mediated immunity (CMI) activity using standard techniques in the art; improvements at the clinical level can be also assessed using known clinical criteria.

In particular, in one aspect the immune response elicited by the composition or vaccine of present invention shows one or more of:

a statistically significant increase in the CMI and/or antibody response, in comparison with pre-vaccination levels, when compared to VZV antigen or live attenuated strain/whole inactivated strain alone;

An improved multivalent CMI response, in comparison with pre-vaccination levels, when compared to VZV antigen or live attenuated strain/whole inactivated strain alone. A multivalent CMI response considers a range of markers for CMI such as (but not limited to) IFN gamma, IL2, TNF alpha and CD40L and an improved multivalent response induces a CMI response across a wider range of such markers or a higher response in one or more of the markers when compared to a VZV antigen or live attenuated strain/whole inactivated strain alone;

Better persistent CMI or antibody response, in comparison with pre-vaccination levels, when compared to VZV antigen or live attenuated strain/whole inactivated strain alone. In one aspect persistence is measured over after 1 month, 2 months, 3 months, 4 months, 5 months, 6 months, 12 months, 24 months, 36 months or 48 months.

In one aspect improvements in the immune response are assessed in the elderly population, suitably the populations over 50 years of age, for whom the risk of zoster or PHN is increased with respect to the population under 50 years of age. Improved immune responses can also be examined in immuno-compromised populations. In one aspect such populations are target populations for any embodiment of the present invention.

In one aspect the population is over 50 years, suitably over 60 years, over 70 years, or even over 80 years and above. In one aspect the population is 50-70 years old.

Thus in one aspect the invention relates to use of the compositions and approaches of the invention in preventing and/or decreasing the severity of zoster or PHN in humans over 50 years of age.

In one aspect the invention relates to use of the compositions and approaches of the invention in preventing and/or decreasing the severity of zoster or PHN in immunocompromised individuals, such as transplant patients or those who are HIV positive.

The term 'immunogenic derivative' encompasses any molecule which retains the ability to induce an immune response to VZV following administration to man. Immunogenic compounds herein are suitably capable of reacting detectably within an immunoassay (such as an ELISA or T-cell stimulation assay) with antisera and/or T-cells from a patient with VZV. Screening for immunogenic activity can be performed using techniques well known to the skilled artisan. For example, such screens can be performed using methods such as those described in Harlow and Lane, Antibodies: A Laboratory Manual, Cold Spring Harbor Laboratory, 1988.

Suitable methods for the generation of derivatives are well known in the art and include standard molecular biology techniques as disclosed, for example, in Sambrook et al [Molecular Cloning: A Laboratory Manual, third edition, 2000, Cold Spring Harbor Laboratory Press], such as techniques for the addition, deletion, substitution or rearrangement of amino acids or chemical modifications thereof. In one aspect derivatives include, for example, truncations or other fragments.

In one aspect derivatives in the context of this invention are amino acid sequences comprising epitopes, i.e., antigenic determinants substantially responsible for the immunogenic properties of a polypeptide and being capable of eliciting an immune response, in one aspect being T cell epitopes.

In one aspect, the level of immunogenic activity of the immunogenic derivative is at least about 50%, in one aspect at least about 70% and in one aspect at least or greater than about 90% of the immunogenicity for the polypeptide from which it is derived, suitably as assessed by immunoassay techniques described above. In some aspects of the invention immunogenic portions may be identified that have a level of immunogenic activity greater than that of the corresponding full-length polypeptide, e.g., having greater than about 100% or 150% or more immunogenic activity.

In one aspect the VZV antigen is a glycoprotein, in one aspect the gE antigen (also known as gp1), or immunogenic derivative thereof.

The gE antigen, anchorless derivatives thereof (which are also immunogenic derivatives) and production thereof is described in EPO405867 and references therein [see also Vafai A. Antibody binding sites on truncated forms of varicella-zoster virus gpI(gE) glycoprotein Vaccine 1994 12:1265-9]. EP192902 also discloses gE and production thereof.

The disclosure of all cited documents is herein fully incorporated by reference.

In one aspect gE is a truncated gE having the sequence of FIG. 1 herein, and as disclosed in Virus research, vol 40, 1996 p 199 ff, herein incorporated fully by reference. Reference to gE hereinafter includes reference to truncated gE, unless otherwise apparent from the context.

Other suitable antigens include, by way of example, gB, gH, gC, gI, IE63 (e.g. see, Huang et al. J. Virol. 1992, 66: 2664, Sharp et al. J. Inf. Dis. 1992, 165:852, Debrus, J. Virol. 1995 May; 69(5):3240-5 and references therein), IE62 (e.g. see Arvin et al. J. Immunol. 1991 146:257, Sabella J. Virol. 1993 December; 67(12):7673-6 and references therein) ORF4 or ORF 10 (Arvin et al. Viral Immunol. 2002 15: 507.)

The present invention herein also contemplates that antigen combinations may be used with the live attenuated or killed VZV, and in one aspect gE may be included in any such combination. In one aspect the invention relates to combinations of gE with IE63 and gE with IE62, for example.

VZV antigens and derivatives of VZV antigens can be tested for suitable immunogenic activity by use in the model systems as described in the Examples of the present application, or by clinical trials in humans. One or more of the following indicators of activity are suitable for consideration in assessment of immunogenic activity:

Increased CD4 or CD8 T cell responses to VZV or antigen derivatives.

Elevation in VZV or antigens derivative specific antibodies.

Enhanced production of cytokines such as interferon γ or IL-2 or TNF α.

Enhanced expression of CD40L on CD4 and CD8 T cells.

Reduction in the incidence of zoster below the incidence found in the general population of similarly at risk individuals, and likewise reduced disease severity and/or associated pain below the incidence found in the general population of similarly at risk individuals.

Increases or reductions, as described above, are suitably statistically significant with respect to appropriate controls, such as an age-matched non-vaccinated group. In one aspect the live attenuated VZV or killed VZV and the VZV antigen or antigen derivatives do not significantly interfere with one another, such that when used in combination the 2 components are still able to provide an immunogenic response to VZV. In one aspect the response is a protective immunogenic response, whether the 2 components are used as a composition or used in sequential administration or coadministration. It will be appreciated that some interference is tolerated, however, provided that the overall protective immune response is improved in some way (increased in magnitude, increased % responders or broadened antigenic responses, for example) over that of either of the original components used individually.

In one aspect the invention relates to the combination of the gE antigen and the OKA strain, used for concomitant or sequential administration, in either order. Where delivery is concomitant then the 2 components are delivered into different injection sites but during the same day, for example. In one aspect different delivery routes are used for the 2 components, in particular subcutaneous delivery for the virus strain such as OKA and intramuscular delivery for the antigen such as gE The present invention also extends to cover, in all embodiments described, the use of combinations of VZV antigens or derivatives with a live attenuated VZV strain or killed VZV. Suitable combinations of antigens include in one aspect gE or immunogenic derivative thereof.

The combined composition, or either or both of the individual components may additionally comprise an adjuvant or immunostimulant such as but not limited to detoxified lipid A from any source and non-toxic derivatives of lipid A, saponins and other reagents, suitably capable of stimulating a TH1 type response.

In one aspect the composition comprises an adjuvant capable of stimulating a TH1 type response.

High levels of Th1-type cytokines tend to favour the induction of cell mediated immune responses to a given antigen, whilst high levels of Th2-type cytokines tend to favour the induction of humoral immune responses to the antigen.

The distinction of Th1 and Th2-type immune response is not absolute. In reality an individual will support an immune response which is described as being predominantly Th1 or predominantly Th2. However, it is often convenient to consider the families of cytokines in terms of that described in murine CD4+ ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p 145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of 11-4, IL-5, IL-6, IL-10.

Suitable adjuvant systems which promote a predominantly Th1 response include, Monophosphoryl lipid A or a derivative thereof, particularly 3-de-O-acylated monophosphoryl lipid A. It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., NY, p 407-419) and has the following structure:

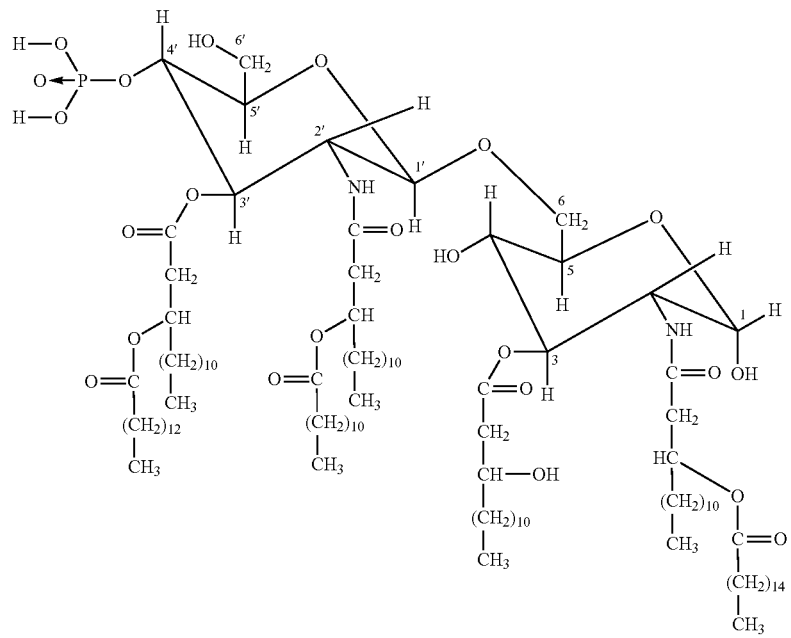

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

In one aspect 3D-MPL is in the form of an emulsion having a small particle size less than 0.2 μm in diameter, and its method of manufacture is disclosed in WO 94/21292. Aqueous formulations comprising monophosphoryl lipid A and a surfactant have been described in WO9843670A2.

The bacterial lipopolysaccharide derived adjuvants to be formulated in the compositions of the present invention may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al., 1986, Int. Arch. Allergy. Immunol., 79(4):392-6; Hilgers et al., 1987, Immunology, 60(1):141-6; and EP 0 549 074 B1). In one aspect the bacterial lipopolysaccharide adjuvant is 3D-MPL.

Accordingly, the LPS derivatives that may be used in the present invention are those immunostimulants that are similar in structure to that of LPS or MPL or 3D-MPL. In another embodiment of the present invention the LPS derivatives may be an acylated monosaccharide, which is a sub-portion to the above structure of MPL.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree *Quillaja Saponaria* Molina), and fractions thereof, are described in U.S. Pat. No. 5,057,540 and "Saponins as vaccine adjuvants", Kensil, C. R., Crit. Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Other saponins which have been used in systemic vaccination studies include those derived from other plant species such as *Gypsophila* and *Saponaria* (Bomford et al., Vaccine, 10(9):572-577, 1992). An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739. In one aspect the combination of QS21 with 3D MPL is used in the present invention.

In one aspect the adjuvant for use in the invention comprises QS21 and a liposomal formulation comprising cholesterol and 3D MPL.

A particularly potent adjuvant formulation involving QS21 and 3D-MPL in an oil in water emulsion is described in WO 95/17210 and is also suitable for use in the present invention.

Accordingly in one embodiment of the present invention there is provided a composition comprising a VZV antigen or derivative of the present invention adjuvanted with detoxified lipid A or a non-toxic derivative of lipid A. In one aspect the composition is adjuvanted with a monophosphoryl lipid A or derivative thereof.

In one aspect the composition additionally comprises a saponin, which in one aspect is QS21, and in another aspect is QS21 quenched with cholesterol as disclosed in WO 96/33739.

The immunogenic composition of the invention optionally comprises an oil in water emulsion, which may be used in combination with other adjuvants such as QS21 and/or 3D MPL as disclosed above. Adjuvant formulations comprising an oil in water emulsion are disclosed in WO9911241 and WO9912565, incorporated herein by reference.

An alternative adjuvant choice is an unmethylated CpG dinucleotides ("CpG"). CpG is an abbreviation for cytosine-guanosine dinucleotide motifs present in nucleic acid. CpG oligonucleotides are disclosed in WO 96/02555 and EP 468520.

In one aspect a combination of any of the adjuvants of the invention described herein (QS21 or QS21 quenched with cholesterol+3DMPL, optionally with an oil in water emulsion) is used with gE, or immunogenic derivative thereof, used in concomitant or sequential administration with a live attenuated VZV or inactivated whole VZV.

The present invention also provides a method for producing a kit suitable for inducing an immune response against zoster, the method comprising mixing a VZV antigen preparation of the present invention together with an adjuvant or adjuvant combination, and combining in a kit with a live attenuated VZV.

The amount of VZV antigen is selected as an amount which induces an immunoprotective response without significant, adverse side effects in typical vaccines. Such amount will vary depending upon which specific immunogen is employed and how it is presented. Generally, it is expected that each dose will comprise 1-1000 µg of protein, such as 2-100 µg, or 5-60 µg. Where gE is used then in one aspect 25-100 µg of gE may be used in humans, such as 40-100 µg of gE for human use, in one aspect about 25 µg, about 50 µg or about 100 µg of gE, suitably 25 µg, 50 µg or 100 µg gE. For the OKA strain, for example, a suitable dose is 500-50000 pfu/0.5 ml, such as 2000-6000 pfu/0.5 ml, with a suitable dose of the GSK Varilrix Oka strain for example being 6000-25,000 per dose, for example 10,000 pfu/dose. Higher doses such as 30,000 pfu, 40000 pfu, 50,000 pfu 60,000 pfu, 70000 pfu, 80000 pfu, 90000 pfu or even 100000 pfu may be employed.

An optimal amount for a particular vaccine can be ascertained by standard studies involving observation of appropriate immune responses in subjects. Following an initial vaccination, subjects may receive one or several booster immunisation adequately spaced. The composition(s) of the present invention may be formulated for any appropriate manner of administration, including for example, topical, oral, nasal, mucosal, intravenous, intradermal, intraperitoneal, subcutaneous and intramuscular administration. Delivery of the OKA strain is, in one aspect, by subcutaneous delivery.

The immunogenic composition of the present invention may be used in a vaccine composition, optionally in combination with an adjuvant and/or (other) suitable carrier.

The VZV antigen and attenuated VZV of the present invention may be used together in a composition to provoke an immune response to VZV, or separately—either concomitantly or sequentially in a prime boost regime. For concomitant or sequential delivery the components of the vaccine may be used in either order. In one embodiment, delivery of a live attenuated VZV or whole inactivated VZV is followed by a VZV antigen or immunogenic derivative thereof. In another embodiment delivery of a VZV antigen or immunogenic derivative thereof is followed by delivery of live attenuated VZV or whole inactivated VZV.

The invention further relates to a method of preventing and/or decreasing the severity of herpes zoster and/or post herpetic neuralgia comprising delivering to an individual at risk of zoster an immunogenic composition comprising a live attenuated VZV and a VZV antigen.

In a further embodiment the invention relates to a method of preventing and/or decreasing the severity of herpes zoster and/or post herpetic neuralgia comprising sequential or concomitant delivery to an individual at risk of zoster of a live attenuated VZV and a VZV antigen.

In one aspect the invention relates to a prime boost regime wherein a VZV antigen, in one aspect an adjuvanted antigen, is delivered first, after which the immune system is boosted with delivery of an attenuated VZV.

A prime boost regime in humans comprises, in one aspect, priming with 25-100 µg gE, in one aspect 40-100 µg gE, such as 50 or about 50 µg gE, or an immunogenic derivative thereof, adjuvanted with QS21 (for example QS21 quenched with cholesterol as described above) and 3D-MPL, and boosting with the OKA strain of VZV.

Where prime boost regimes are used, or where multiple vaccination regimes are used, then 2, 3, 4 or more immunisations may be employed. Suitable regimes for prime boost include 1, 2, 3, 4, 5 or 6 months between individual immunisations.

A prime boost schedule comprises, in one aspect, delivery of a VZV antigen or immunogenic derivative thereof, suitably an adjuvanted VZV antigen or derivative, at 0 months and boosting with a live attenuated VZV at 2M.

In an alternative delivery schedule there is concomitant delivery of both of the two individual components (VZV antigen or derivative and live attenuated VZV) at both 0 and 2 months.

In a still further embodiment the invention relates to a kit comprising a live attenuated VZV or inactivated whole VZV and a VZV antigen.

The invention also relates to a method for the manufacture of an immunogenic composition, the method comprising combining a live attenuated VZV/whole inactivated and a VZV antigen.

The invention further relates to use of a live attenuated VZV strain in the preparation of a combination vaccine with a VZV antigen for the prevention of herpes zoster, and to use of a VZV antigen in the preparation of a combination vaccine with a live attenuated VZV strain for the prevention of herpes zoster.

In a second, aspect of the invention a gE antigen, or immunogenic derivative or immunogenic fragment thereof, may be used with an adjuvant to provide an immunogenic composition or vaccine. That is, the gE antigen or immunogenic derivative or immunogenic fragment thereof may be used in a vaccination schedule in the absence of a live attenuated strain or whole inactivated strain.

Thus the second aspect of the invention relates to an immunogenic composition or vaccine comprising gE or immunogenic derivative or immunogenic fragment thereof in combination with a TH1-adjuvant.

The invention also particularly relates to use of a composition comprising gE or an immunogenic derivative or immunogenic fragment thereof in combination with a TH-1 adjuvant, in the preparation of a medicament for the prevention or amelioration of herpes zoster reactivation and/or post herpetic neuralgia.

The term "immunogenic derivative" in respect of gE is as described above, along with methods to obtain such derivatives such as fragments of gE. Immunogenic fragments as described herein are immunogenic derivatives which retain the ability to induce an immune response to VZV following administration to man.

In one aspect of the invention a gE truncate is used in which gE has a C terminal truncation.

In one aspect the truncation removes from 4 to 20 percent of the total amino acid residues at the carboxy terminal end.

In one aspect the gE is lacking the carboxy terminal anchor region (suitably approximately amino acids 547-623 of the wild type sequence). In one aspect gE is a truncated gE having the sequence of FIG. 1 herein, and as disclosed in Virus research, (Haumont et al Vol 40, 1996 p 199-204), herein incorporated fully by reference.

Reference to gE hereinafter includes reference to truncated gE, or other fragments or derivative of gE, unless otherwise apparent from the context.

In another aspect of the invention the composition comprises full length gE.

In another aspect the gE or derivative or fragment thereof is lyophilised. In another aspect the gE or derivative or fragment thereof is reconstituted in a solution containing an adjuvant (such as an adjuvant containing QS21, cholesterol and 3D MPL) before delivery.

In one embodiment the composition or vaccine comprises gE and a TH-1 adjuvant and does not comprise an IE63 antigen or portion thereof. In one embodiment the composition or vaccine comprises gE and a TH-1 adjuvant and does not comprise any other VZV antigen. In one embodiment the composition or vaccine comprises gE and a TH-1 adjuvant and does not comprise any other viral antigen.

In one aspect the gE or immunogenic fragment thereof is not in the form of a fusion protein.

In one aspect the composition or vaccine consists essentially of QS21, a truncated VZV gE antigen and liposomes comprising cholesterol and 3D-MPL.

In one aspect the composition or vaccine consists of 3D-MPL, QS21, a truncated VZV gE antigen, liposomes comprising cholesterol and a pharmaceutically acceptable carrier.

The composition may be used in the preparation of a medicament for the prevention or amelioration of herpes zoster reactivation and/or post herpetic neuralgia.

The composition or vaccine is suitably used in the population of people 50 or older than 50. Suitably the population is the population of those older than 55, 60, 65, 70, 75, 80, or older than 80. Suitably the population is 50-70 years.

In one aspect the population of individuals are those who have had varicella or who have had a live varicella vaccine.

Thus the invention relates to use of a composition as described above in the preparation of a medicament for the prevention or amelioration of herpes zoster reactivation and/or post herpetic neuralgia in a population of people 50 or above.

The invention thus also relates to a method for the prevention or amelioration of herpes zoster reactivation and/or post herpetic neuralgia, the method comprising delivering to an individual in need thereof a composition of the invention.

In one aspect the composition of the first and second aspects of the invention are used in those individuals in whom the varicella zoster virus has not reactivated.

The composition may be used at doses and delivery routes as outlined above for the first aspect of the invention. Specifically the amount of gE is selected as an amount which induces an immunoprotective response without significant, adverse side effects in typical vaccines. Such amount will vary depending upon which specific immunogen is employed and how it is presented. Generally, it is expected that each dose will comprise 1-1000 µg of protein, such as 2-100 µg, or 5-60 µg. Where gE is used then suitably 25-100 µg gE is used, in one aspect 40-100 µg of gE, such as about 25 µg, 50 µg or about 100 µg of gE, suitably 25 µg, 50 µg or 100 µg gE. An optimal amount for a particular vaccine can be ascertained by standard studies involving observation of appropriate immune responses in subjects. Following an initial vaccination, subjects may receive one or several booster immunisation adequately spaced.

In one aspect the gE and adjuvant composition or vaccine is used in a one dose delivery regime. In one aspect the gE and adjuvant composition or vaccine is used in a two dose delivery regime.

In one aspect the composition or vaccine of the invention is used in a 2 dose regime with a 2 month spacing between doses.

In one aspect the TH-1 adjuvant is any adjuvant identified above for the first aspect of the invention. In particular, a combination of 3D MPL and QS21 may be used, for example as disclosed in WO94/00153, or a less reactogenic composition where the QS21 is quenched with cholesterol as disclosed in WO 96/33739 and U.S. Pat. No. 6,846,489. An alternative adjuvant comprises QS21 and 3D-MPL in an oil in water emulsion as described in WO 95/17210.

In one aspect a formulation comprises a C terminal truncation of the VZV gE antigen, for example that given in FIG. 1, in combination with 3D MPL and QS21.

In another aspect the invention relates to a kit comprising, as separate components, a TH-1 adjuvant and a gE antigen or immunogenic fragment thereof, as described above, suitable for extemporaneous preparation of a vaccine composition. In one aspect both components are liquids. In one aspect one component is lyophilised and is suitable for reconstitution with the other component. In one aspect the kit comprises a gE antigen having the sequence of FIG. 1 and an adjuvant comprising QS21 and liposomes comprising cholesterol and 3D MPL.

Vaccine preparation is generally described in New Trends and Developments in Vaccines, Voller et al. (eds), University Park Press, Baltimore, Md., 1978.

Aspects of the present invention include:

A An immunogenic composition comprising a VZV antigen or immunogenic derivative thereof in combination with a live attenuated VZV or whole inactivated VZV.

B A method of preventing and/or decreasing the severity of herpes zoster and/or post herpetic neuralgia (PHN) comprising delivering to an individual an immunogenic composition comprising a VZV antigen or immunogenic derivative thereof in combination with a live attenuated VZV or whole inactivated VZV.

C A method of preventing and/or decreasing the severity of herpes zoster and/or post herpetic neuralgia, the method comprising sequential or concomitant delivery to an individual of a VZV antigen or immunogenic derivative thereof and a live attenuated VZV or whole inactivated VZV.

D A method according to paragraph C wherein a VZV antigen is delivered before live attenuated VZV.

E A method according to paragraph C wherein a VZV antigen is delivered after live attenuated VZV.

F A method according to paragraph C wherein a VZV antigen is delivered concomitantly with live attenuated VZV, preferably with each component in a different arm of a patient.

G A kit comprising a live attenuated VZV or whole inactivated VZV and, separately, a VZV antigen or immunogenic derivative thereof, the components suitable for concomitant or sequential delivery, or for mixing as a single composition prior to delivery.

H A method for the manufacture of an immunogenic composition, the method comprising combining a live attenuated VZV or whole inactivated VZV with a VZV antigen or immunogenic derivative thereof.

I Use of a live attenuated VZV strain in the preparation of an immunogenic composition for preventing and/or decreasing the severity of herpes zoster and/or post herpetic neuralgia, wherein the live attenuated VZV strain is used in combination with a VZV antigen or immunogenic derivative thereof.

J Use of a whole inactivated VZV strain in the preparation of an immunogenic composition for preventing and/or decreasing the severity of herpes zoster and/or post herpetic neuralgia, wherein the whole inactivated VZV strain is used in combination with a VZV antigen or immunogenic derivative thereof.

K Use of a VZV antigen or immunogenic derivative thereof in the preparation of an immunogenic composition for preventing and/or decreasing the severity of herpes zoster and/or post herpetic neuralgia, wherein the VZV antigen is used in combination with a live attenuated VZV strain or whole inactivated VZV strain.

L Use according to any of paragraphs I-K wherein the antigen or derivative thereof is delivered in a prime boost approach before the VZV strain.

M Use according to any of paragraphs I-K wherein the antigen or derivative thereof is delivered in a prime boost approach after the VZV strain.

N Use according to any of paragraphs I-K wherein the antigen or derivative thereof is delivered concomitantly with the VZV strain.

O Use according to any of paragraphs I-K wherein the antigen or derivative thereof is delivered in admixture with the VZV strain.

P A use, method, kit, or composition according to any preceding paragraph wherein the live attenuated VZV strain is the OKA strain.

Q A use method, kit, composition according to any preceding paragraph wherein the VZV antigen the gE antigen or immunogenic derivative thereof.

R A use, method, kit, composition or vaccine according to any preceding claim wherein the VZV antigen is delivered with an adjuvant capable of stimulating a TH1 type response.

The present invention is illustrated by the following, non limiting Examples.

EXAMPLE 1

Three experimental groups may be set up to study both aspects of the invention:

| | | Regime |
|---|---|---|
| 1 | 50 μg gE + adjuvant AS1 (MPL ®/QS21) | 0, 2 months |
| 2 | OKA strain (Varilrix ™)~10,000 pfu/dosc | 0, 2 months |
| 3 | Concomitant administration of 50 μg gE + AS1 group (as in 1) with Varilrix ™ (as in 2) | 0, 2 months |

MPL ® = 3D-MPL

The gE used can be truncated gE, as disclosed in FIG. 1. Varilrix™ is a commercially available OKA strain.

Human volunteers (for example, 50 per group—healthy, aged 50-70 years) can be selected to be vaccinated according to the above protocol, and results may be assessed by measuring both cell mediated immunity and antibody responses, for example by intracellular staining (ICS, Roederer et al. 2004 Clin. Immunol. 110: 199) or ELISA techniques respectively, these being well known in the art.

Specific cell-mediated immunity may be evaluated by, for example, in vitro incubation of patient PBMC with varicella-zoster virus extracts as well as specific VZV antigens or peptides gE, IE63 and IE62. Analysis may be made at the level of, for example:

a Lymphoproliferation (data expressed as Stimulation Index [SI]): GM, GM fold increase and % of responders b Analysis of IFNγ or IL2 or TNFα, or CD 40L expression by CD4 and CD8 cells by ICS (intracellular cytokine staining): GM, GM fold increase and % of responders Efficacy can be assessed by looking for a significant increase in the CMI and/or antibody response in comparison with pre-vaccination levels.

Efficacy of other antigens or approaches can be assessed using these or similar techniques, and comparing pre-vaccination levels with post vaccination levels.

EXAMPLE 2

The experiment of Example 1 was carried out in human volunteers of different ages, as follows:

| | |
|---|---|
| Group A | gE AS1 in adults 18-30 years |
| Group B | gE delivered concomitantly with the Varilrix OKA strain 18-30 years |
| Group C | Varilrix OKA strain alone in adults 50-70 years |
| Group D | gE AS1 in adults 50-70 years |
| Group E | gE delivered concomitantly with the Varilrix OKA strain 50-70 years |

The vaccination schedule was as follows:

| Group | Age (Y) | N | Vacc 1 (Month 0) | Vacc 2 (Month 2) |
|---|---|---|---|---|
| A | 18-30 | 10 | gE-AS1 | gE-AS1 |
| B | 18-30 | 10 | gE-AS1 + Varilrix ™ | gE AS1 + Varilrix ™ |
| C | 50-70 | 45 | Varilrix ™ | Varilrix ™ |
| D | 50-70 | 45 | gE-AS1 | gE-AS1 |
| E | 50-70 | 45 | gE-AS1 + Varilrix ™ | gE-AS1 + Varilrix ™ |

The adjuvant AS1 comprises 3D MPL and QS21 in a quenched form with cholesterol, and was made as described in WO9633739, incorporated herein by reference. In particular the AS1 adjuvant was prepared essentially as Example 1.1 of WO9633739.

The adjuvant comprises: liposomes, which in turn comprise dioleoyl phosphatidylcholine (DOPC), cholesterol and 3D MPL [in an amount of 1000 μg DOPC, 250 μg cholesterol and 50 μg 3D MPL, each value given approx per vaccine dose], QS21 [50 μg/dose], PBS and water to a volume of 0.5 ml.

In the process of production of liposomes containing MPL the DOPC (Dioleyl phosphatidylcholine), cholesterol and MPL are dissolved in ethanol. A lipid film is formed by solvent evaporation under vacuum. Phosphate Buffer Saline or PBS (9 mM $Na_2HPO_4$, 41 mM $KH_2PO_4$, 100 mM NaCl) at pH 6.1 is added and the mixture is submitted to prehomogenization followed by microfluidization at 15,000 psi (20 cycles). This leads to the production of liposomes which are sterile filtered through a 0.22 μm membrane in an aseptic (class 100) area. The sterile product is then distributed in sterile glass containers and stored in a cold room (+2 to +8° C.). In this way the liposomes produced contain MPL in the membrane (the "MPL in" embodiment of WO9633739).

The truncated gE of FIG. 1 was expressed in CHO K1 cells using standard techniques and purified using, in order, anion exchange chromatography, hydrophobic interaction chromatography, ion exchange chromatography, diafiltration, and nanofiltration followed by sterilisation through a 0.22 µm filter.

In particular, the following steps were used in the purification of gE

First Stage Anion Exchange Chromatography

The culture supernatant containing the gE (approx. 30 mg/l) is purified, either directly after clarification of the cell suspension or after defrosting at 4° C. After transfer into a 20-liter carboy, the pH of the supernatant is adjusted to 6.

The capture stage takes place at ambient temperature on a chromatography column containing a Q Sepharose XL resin.

After sanitisation with sodium hydroxide, the column is conditioned in the capture buffer (piperazine 20 mM pH 6). The supernatant is then loaded on the column and the column is washed with equilibration buffer and a solution of piperazine 20 mM+NaCl 150 mM pH 6.

The fraction containing the gE is then eluted with a solution of piperazine 20 mM+NaCl-250 mM at pH 6.

Second Stage Hydrophobic Interaction Chromatography

This chromatography stage takes place at ambient temperature on a Toyopearl butyl-650 M resin (Tosoh Biosep).

The fraction eluted with 20 mM piperazine+250 mM NaCl in the Q Sepharose XL stage is made up to 1M in ammonium sulphate and adjusted to pH 7.5.

After sanitisation with sodium hydroxide and before loading of this fraction, the column is conditioned in the capture buffer (50 mM $KH_2PO_4$+1 μM ammonium sulphate pH 7.5). After loading, the column is washed with buffer 50 mM $KH_2PO_4$+100 mM $(NH_4)_2SO_4$ pH 7.5. The gE is eluted with buffer 50 mM $KH_2PO_4$+25 mM $(NH_4)_2SO_4$ pH 7.5.

Third Stage Affinity Chromatography on Immobilised Metal Ion

This chromatography stage takes place at ambient temperature on a Chelating Sepharose Fast Flow resin. This resin is saturated in metal ion (Ni) by application of a nickel sulphate solution (1%) and excess unbound ions (Ni), removed by washing. The gE fraction eluted at 50 mM $KH_2PO_4$+25 mM $(NH_4)_2SO_4$ pH 7.5 in the hydrophobic phase is made up to 0.5 M NaCl and adjusted to pH 7.5.

After sanitisation, the column is equilibrated in the capture buffer (50 mM $KH_2PO_4$+0.5 M NaCl pH 7.5). The gE solution is loaded on the column, which is then washed with a solution of 50 mM $KH_2PO_4$+0.5 M NaCl pH 5.6. The gE is then eluted with a buffer of 50 mM sodium acetate+0.5 M NaCl pH 5, and neutralised with a Tris 1M solution pH 9.5.

Fourth Stage: Diafiltration

The buffer exchange and the elimination of salts from the gE fraction eluted at pH 5 in the previous stage are carried out by tangential ultrafiltration. This stage is carried out entirely at +4° C.

The ultrafiltration is run by the Millipore Proflux M12 system, fitted with a 10 kDa Pellicon2 Mini membrane of regenerated cellulose (cat: P2C010C01) of limit nominal molecular weight and a surface area of 0.1 $m^2$ placed in a Pellicon2 mini-cassette housing (cat.XX42PMINI).

After rinsing with water and sanitisation with sodium hydroxide, the whole system with membrane is rinsed with 2 liters of modified PBS buffer (=8.1 mM $Na_2HPO_42H_2O$, 1.47 mM $KH_2PO_4$, 137 mM NaCl, 2.68 mM KCL pH 7.2) and then equilibrated with 2 liters of the same buffer until a pH value of 7.2 is reached in the permeate.

The measurement of the permeability of the membrane is verified. The integrity test on the membrane is carried out by putting the system under pressure up to 1 bar before and at the end of the diafiltration stage. If this membrane is used twice with an interval of one week, the integrity will be tested 3 times (once before each ultrafiltration and once after the second filtration). The membrane is considered to be intact if the loss of pressure recorded over 5 minutes is less than 0.1 bar. The concentration of the gE fraction eluted at pH 5 in the affinity stage is evaluated by measuring the optical density at 280 nm. The correlation between the absorbance at 280 nm and the protein concentration of the gE by microBCA is fixed at 1 $OD_280$=1.75 mg/ml.

The solution containing the gE is dia-filtered against 10 volumes of modified PBS buffer (=8.1 mM $Na_2HPO_42H_2O$, 1.47 mM $KH_2PO_4$, 137 mM NaCl, 2.68 mM KCL pH 7.2). The pressure conditions are set such that the diafiltration period is about 1½-2 hours (permeate flow approx. 60 ml/min). The diafiltration residue is then recovered and on the basis of the baseline $OD_280$ the membrane is rinsed with modified PBS to give an approximate final concentration of 0.4 mg/ml.

Fifth Stage: Nanofiltration

This next stage makes it possible to eliminate viruses with a diameter of more than 15 nm by retention. The stage is carried out entirely at +4° C.

The nanofiltration is carried out on a PLANOVA 15N filter (mean pore size 15 nm; filtration surface area 0.12 $m^2$ (ASAHI cat: 15NZ-120)). Under a constant pressure of 0.45 bar, the gE solution is filtered on the membrane and recovered on the other side with viruses removed.

The pipes and housing (column XK50) are sanitised for 2 hours with a solution of NaOH 0.5M. The whole is then rinsed and neutralised with the modified PBS buffer (same buffer as for the diafiltration) until a pH value of 7.2 is achieved.

After fixing the nanofilter PLANOVA 15N (feed side) under the casing, the filter is rinsed and equilibrated with a modified PBS solution.

The diafiltration residue containing the gE solution is first pre-filtered through 0.22 μm (mini kleenpak OU Acropak20, depending on the volume to be filtered) before being nanofiltered at a constant pressure of 0.45 bar on the PLANOVA 15N.

At the end of nanofiltration, the filter is rinsed with a sufficient volume of modified PBS to give a final concentration of the bulk of approx. 0.3 mg/ml.

To end, the membrane is washed with 50 ml modified PBS. The solution is recovered through the residue outlet.

The integrity tests on the PLANOVA 15N membrane are then carried out as follows:

the first test consists of putting the membrane under pressure (1.0 kg/$cm^2$) and observing for formation of air bubbles. This test detects any large splits.

the second test: elimination of particles of gold (PARTICORPLANOVA-QCVAL4) verifies the structure of the membrane (good distribution of large pores and capillaries).

Vaccine Composition

The gE component of the vaccine comprises 50 μg gE and the excipients sodium chloride, potassium chloride, monopotassium phosphate, disodium phosphate and water for injection as well as the AS1 adjuvant. The function of the inorganic salts is to ensure isotonicity and physiological pH.

In a sterile glass container, water for injection, concentrated phosphate buffered saline and gE antigen were mixed in order to reach the ingredient concentration as below:

| Ingredients | Quantitative (per dose) |
|---|---|
| gE | 50 μg |
| Sodium chloride (NaCl) | 1603 μg |
| Disodium phosphate (NaH₂PO₄) | 288 μg |
| Monopotassium phosphate (KH₂PO₄) | 40 μg |
| Potassium chloride (KCl) | 40 μg |
| Water for injection | q.s. ad 0.2 mL |

The solution is mixed for 30 to 40 minutes. The pH is checked and adjusted at 7.2+−.0.1 with HCl or NaCl or appropriate and stir for an additional 10 minutes.

The final bulk was stored in polypropylene bottles at −20° C. and transferred to GSK Bio for filling. The vaccine is filled into 3 ml, sterile, siliconised glass vials (0.25 ml/vial) which are closed with grey chlorobutyl rubber stoppers and sealed with central tear-off aluminium cap. The inspected, approved vials are then stored at −20° C.

Vaccine Delivery

The gE-AS1 vaccine for administration was obtained by mixing the liquid antigen preparation with the liquid AS1 adjuvant immediately prior to injection (a maximum of one hour before injection). The OKA (Varilrix™) was a commercially available lot prepared according to the manufacturer's instructions.

Vaccine formulations were as follows:

| Vaccine | gE |
|---|---|
| Formulation | 50 μg VZV (gE) antigen in 0.2 ml volume AS1 in 0.5 ml volume |
| Presentation | Glass vial containing liquid gE |
| Total Dose Volume* | 0.7 ml (after reconstitution) |

| Vaccine | Varilrix with diluent |
|---|---|
| Formulation | Approximately $10^{4.0}$ pfu/dose 0/5 ml volume |
| Presentation | Glass vial containing containing lyophilized vaccine for reconstitution |
| Total Dose Volume* | 0.5 ml |

The gE AS1 component was administered by intramuscular injection.

The Varilrix component was administered by subcutaneous injection.

Analysis of Results

The clinical trial protocol, filed in preparation for the clinical trial, outlined the types of studies that were to be carried out in the trial, as follows:

a Lymphoproliferation (data expressed as Stimulation Index [SI]): GM, fold increase in GM and % of responders after stimulation by VZV lysate.

b IFN gamma and/or IL2, TNF alpha, CD40L, CD4 and CD8 response by ICS (intracellular staining): GM, -fold increase in GM and % of responders after stimulation by VZV lysate and gE, IE62 and IE63 peptides.

Lymphoproliferation

Peripheral blood antigen-specific lymphocytes can be restimulated in vitro to proliferate if incubated with their corresponding antigen. Consequently, the amount of antigen specific lymphocytes can be estimated by counting tritiated thymidine incorporation assay. In the present study, VZV antigen or peptide derived from VZV proteins will be used as antigen to restimulate VZV-specific lymphocytes. Results will be expressed as a stimulation index (SI) which corresponds to the ratio between antigen-specific and background lymphoproliferation.

Cytokine Flow Cytometry (CFC)

Peripheral blood antigen-specific CD4 and CD8 T cells can be restimulated in vitro to express CD40L, IL-2, TNF alpha and IFN gamma if incubated with their corresponding antigen. Consequently, antigen-specific CD4 and CD8 T cells can be enumerated by flow cytometry following conventional immunofluorescence labelling of cellular phenotype as well as intracellular cytokines production. In the present study, VZV antigen or peptide derived from VZV proteins will be used as antigen to restimulate VZV-specific T cells. Results will be expressed as a frequency of cytokine(s)-positive CD4 or CD8 T cell within the CD4 or CD8 T cell sub-population.

Specific Antibody (Anti-VZV and Anti-gE)

Antibody levels against VZV and gE will be measured using classical ELISA assays.

Results of the experiment are shown in tabular form. FIGS. 2-6 present results in a graphical form for antibody (FIGS. 2-4, see tables 1.1 a-c) and CMI responses (FIGS. 5 and 6—see table C1/"CD4 all doubles" test with gE antigen or Varilirix, median values).

| HUMORAL IMMUNE RESPONSE | |
|---|---|
| Table I.1a | Seropositivity rates and GMTs for VZV IGG antibodies (ATP cohort for immunogenicity) . . . |
| Table I.1b | Seropositivity rates and GMTs for VZV.GE antibodies (ATP cohort for immunogenicity) . . . |
| Table I.1c | Seropositivity rates and GMTs for IFA antibodies (ATP cohort for immunogenicity) . . . |
| Table I.2b | Seroconversion rates for gE antibody titer at each post-vaccination time point (ATP cohort for immunogenicity) . . . |
| Table I.3a | Vaccine response for VZV antibody titer at each post-vaccination time point (ATP cohort for immunogenicity) . . . |
| Table I.3b | Vaccine response for gE antibody titer at each post-vaccination time point (ATP cohort for immunogenicity) . . . |
| Table I.3c | Vaccine response for IFA antibody titer at each post-vaccination time point (ATP cohort for immunogenicity) . . . |

TABLE I.Ia

Seropositivity rates and GMTs for VZV IGG antibodies (ATP cohort for immunogenicity)

| | | | | | >=50 MIU/ML | | | GMT | | | | |
|---|---|---|---|---|---|---|---|---|---|---|---|---|
| | | | | | | 95% CI | | | 95% CI | | | |
| Antibody | Group | Timing | N | n | % | LL | UL | value | LL | UL | Min | Max |
| VZV IGG | gF/Y | PRE | 10 | 10 | 100 | 69.2 | 100 | 1875.9 | 1077.2 | 3266.8 | 455.0 | 4634.0 |
| | | PI(M1) | 10 | 10 | 100 | 69.2 | 100 | 14843.0 | 8457.7 | 26049.0 | 6351.0 | 65242.0 |

TABLE I.Ia-continued

Seropositivity rates and GMTs for VZV IGG antibodies (ATP cohort for immunogenicity)

| Antibody | Group | Timing | N | n | % | >=50 MIU/ML 95% CI LL | UL | GMT value | 95% CI LL | UL | Min | Max |
|---|---|---|---|---|---|---|---|---|---|---|---|---|
| | | PI(M2) | 10 | 10 | 100 | 69.2 | 100 | 10697.6 | 6768.2 | 16908.4 | 3167.0 | 29622.0 |
| | | PII(M3) | 10 | 10 | 100 | 69.2 | 100 | 14330.6 | 10492.9 | 19571.9 | 7173.0 | 30894.0 |
| | gEVAR/Y | PRE | 10 | 10 | 100 | 69.2 | 100 | 1047.4 | 519.3 | 2112.6 | 300.0 | 5754.0 |
| | | PI(M1) | 10 | 10 | 100 | 69.2 | 100 | 12859.4 | 7063.0 | 23412.8 | 3346.0 | 49163.0 |
| | | PI(M2) | 10 | 10 | 100 | 69.2 | 100 | 10072.2 | 5631.4 | 18014.7 | 3678.0 | 36289.0 |
| | | PII(M3) | 10 | 10 | 100 | 69.2 | 100 | 15245.7 | 9930.9 | 23404.8 | 6381.0 | 36534.0 |
| | VAR/E | PRE | 45 | 45 | 100 | 92.1 | 100 | 856.9 | 647.5 | 1134.1 | 100.0 | 5377.0 |
| | | PI(M1) | 45 | 45 | 100 | 92.1 | 100 | 2538.8 | 2072.3 | 3110.3 | 288.0 | 8034.0 |
| | | PI(M2) | 45 | 45 | 100 | 92.1 | 100 | 2292.2 | 1880.6 | 2793.9 | 374.0 | 7549.0 |
| | | PII(M3) | 45 | 45 | 100 | 92.1 | 100 | 2338.3 | 1933.6 | 2827.7 | 523.0 | 16994.0 |
| | gE/E | PRE | 45 | 45 | 100 | 92.1 | 100 | 940.1 | 744.2 | 1187.6 | 208.0 | 4221.0 |
| | | PI(M1) | 45 | 45 | 100 | 92.1 | 100 | 5897.4 | 4594.7 | 7569.5 | 659.0 | 27042.0 |
| | | PI(M2) | 45 | 45 | 100 | 92.1 | 100 | 4523.3 | 3570.6 | 5729.4 | 598.0 | 19268.0 |
| | | PII(M3) | 45 | 45 | 100 | 92.1 | 100 | 9083.9 | 7437.6 | 11094.5 | 2493.0 | 42073.0 |
| | gEVAR/E | PRE | 44 | 44 | 100 | 92.0 | 100 | 1165.1 | 954.6 | 1422.1 | 209.0 | 5558.0 |
| | | PI(M1) | 44 | 44 | 100 | 92.0 | 100 | 8371.7 | 6637.2 | 10559.5 | 2509.0 | 56066.0 |
| | | PI(M2) | 44 | 44 | 100 | 92.0 | 100 | 6849.1 | 5422.6 | 8650.8 | 1753.0 | 55958.0 |
| | | PII(M3) | 44 | 44 | 100 | 92.0 | 100 | 9849.1 | 8201.7 | 11827.3 | 3528.0 | 38664.0 | gEY = gE-AS1/18-30 years
gEVAR/Y = gE-AS1 + Varilrix/18-30 years
VAR /E = Varilrix/50-70 years
gE/E = gE-AS1/50-70 years
gEVARE = gE-AS1 + Varilrix/50-70 years
GMC = geometric mean antibody concentration calculated on all subjects
N = number of subjects with available results
n/% = number/percentage of subjects with concentration within the specified range
95% CI = 95% confidence interval;
LL = Lower Limit,
UL = Upper Limit
MIN/MAX = Minimum/Maximum
PRE = Pre-vaccination dose 1
PI(M1) = Post-vaccination dose 1 (Month 1)
PI(M2) = Post-vaccination dose 1 (Month 2)
PII(M3) = Post-vaccination dose 2 (Month 3)

TABLE I.1b

Seropositivity rates and GMTs for VZV.GE antibodies (ATP cohort for immunogenicity)

| Antibody | Group | Timing | N | n | % | >=109 ELU/ML 95% CI LL | UL | GMT value | 95% CI LL | UL | Min | Max |
|---|---|---|---|---|---|---|---|---|---|---|---|---|
| VZV.GE | gE/Y | PRE | 10 | 8 | 80.0 | 44.4 | 97.5 | 302.6 | 120.5 | 759.9 | <109.0 | 2169.0 |
| | | PI(M1) | 10 | 10 | 100 | 69.2 | 100 | 18365.0 | 9610.6 | 35094.1 | 5697.0 | 106829.0 |
| | | PI(M2) | 10 | 10 | 100 | 69.2 | 100 | 11076.6 | 7037.4 | 17433.9 | 3528.0 | 30190.0 |
| | | PII(M3) | 10 | 10 | 100 | 69.2 | 100 | 15842.6 | 11543.4 | 21743.1 | 7502.0 | 30487.0 |
| | gEVAR/Y | PRE | 10 | 7 | 70.0 | 34.8 | 93.3 | 190.3 | 96.4 | 375.6 | <109.0 | 661.0 |
| | | PI(M1) | 10 | 10 | 100 | 69.2 | 100 | 16225.7 | 8657.3 | 30410.6 | 3613.0 | 58950.0 |
| | | PI(M2) | 10 | 10 | 100 | 69.2 | 100 | 11554.7 | 6312.5 | 21150.4 | 3656.0 | 47423.0 |
| | | PII(M3) | 10 | 10 | 100 | 69.2 | 100 | 18101.2 | 11384.7 | 28780.5 | 7649.0 | 44539.0 |
| | VAR/E | PRE | 44 | 35 | 79.5 | 64.7 | 90.2 | 266.9 | 189.6 | 375.8 | <109.0 | 5866.0 |
| | | PI(M1) | 45 | 45 | 100 | 92.1 | 100 | 1011.3 | 770.0 | 1328.2 | 177.0 | 6386.0 |
| | | PI(M2) | 45 | 45 | 100 | 92.1 | 100 | 948.1 | 701.6 | 1281.2 | 127.0 | 6759.0 |
| | | PII(M3) | 45 | 45 | 100 | 92.1 | 100 | 1146.9 | 841.5 | 1563.0 | 164.0 | 16249.0 |
| | gE/E | PRE | 45 | 37 | 82.2 | 67.9 | 92.0 | 231.1 | 178.8 | 298.7 | <109.0 | 899.0 |
| | | PI(M1) | 45 | 45 | 100 | 92.1 | 100 | 6099.1 | 4401.9 | 8450.8 | 367.0 | 40101.0 |
| | | PI(M2) | 45 | 45 | 100 | 92.1 | 100 | 4844.2 | 3406.5 | 6888.8 | 288.0 | 42488.0 |
| | | PII(M3) | 45 | 45 | 100 | 92.1 | 100 | 14816.8 | 12122.2 | 18110.2 | 3047.0 | 58792.0 |
| | gEVAR/E | PRE | 44 | 42 | 95.5 | 84.5 | 99.4 | 336.1 | 268.0 | 421.5 | <109.0 | 1531.0 |
| | | PI(M1) | 44 | 44 | 100 | 92.0 | 100 | 8272.6 | 6071.1 | 11272.4 | 363.0 | 54878.0 |

TABLE I.1b-continued

Seropositivity rates and GMTs for VZV.GE antibodies (ATP cohort for immunogenicity)

| Antibody | Group | Timing | N | n | % | >=109 ELU/ML 95% CI LL | UL | GMT value | 95% CI LL | UL | Min | Max |
|---|---|---|---|---|---|---|---|---|---|---|---|---|
| | | PI(M2) | 44 | 44 | 100 | 92.0 | 100 | 7870.4 | 5937.0 | 10433.4 | 1512.0 | 84465.0 |
| | | PII(M3) | 44 | 44 | 100 | 92.0 | 100 | 16616.0 | 13972.3 | 19760.0 | 4774.0 | 61558.0 | gE/Y = gE-AS1/18-30 years
gEVAR/Y - gE-AS1 + Varilrix/18-30 years
VAR/E = Varilrix/50-70 years
gE/E = gE-AS1/50-70 years
gEVAR/E = gE-AS1 + Varilrix/50-70 years
GMC = geometric mean antibody concentration calculated on all subjects
N = number of subjects with available results
n/% = number/percentage of subjects with concentration within the specified range
95% CI = 95% confidence interval;
LL = Lower Limit,
UL = Upper Limit
MIN/MAX = Minimum/Maximum
PRE = Pre-vaccination dose 1
PI(M1) = Post-vaccination dose 1 (Month 1)
PI(M2) = Post-vaccination dose 1 (Month 2)
PII(M3) = Post-vaccination dose 2 (Month 3)

TABLE I. 1c

Seropositivity rates and GMTs for IFA antibodies (ATP cohort for immunogenicity)

| Antibody | Group | Timing | N | n | % | >=4 1/DIL 95% CI LL | UL | GMT value | 95 CI LL | UL | Min | Max |
|---|---|---|---|---|---|---|---|---|---|---|---|---|
| IFA | gE/Y | PRE | 10 | 10 | 100 | 69.2 | 100 | 1351.2 | 691.9 | 2638.8 | 256.0 | 4096.0 |
| | | PI(M1) | 10 | 10 | 100 | 69.2 | 100 | 10809.4 | 6040.0 | 19345.1 | 4096.0 | 65536.0 |
| | | PI(M2) | 10 | 10 | 100 | 69.2 | 100 | 12416.8 | 6631.6 | 23248.7 | 2048.0 | 32768.0 |
| | | PII(M3) | 10 | 10 | 100 | 69.2 | 100 | 14263.1 | 10423.6 | 19516.8 | 8192.0 | 32768.0 |
| | gEVAR/Y | PRE | 10 | 10 | 100 | 69.2 | 100 | 776.0 | 321.6 | 1872.5 | 256.0 | 16384.0 |
| | | PI(M1) | 10 | 10 | 100 | 69.2 | 100 | 9410.1 | 5638.8 | 15703.7 | 4096.0 | 32768.0 |
| | | PI(M2) | 10 | 10 | 100 | 69.2 | 100 | 14263.1 | 8546.9 | 23802.4 | 8192.0 | 65536.0 |
| | | PII(M3) | 10 | 10 | 100 | 69.2 | 100 | 12416.8 | 8173.6 | 18862.6 | 8192.0 | 32768.0 |
| | VAR/E | PRE | 45 | 45 | 100 | 92.1 | 100 | 686.1 | 508.5 | 925.6 | 128.0 | 8192.0 |
| | | PI(M1) | 45 | 45 | 100 | 92.1 | 100 | 2702.4 | 2115.6 | 3451.9 | 512.0 | 32768.0 |
| | | PI(M2) | 45 | 45 | 100 | 92.1 | 100 | 1838.7 | 1454.0 | 2325.2 | 256.0 | 16384.0 |
| | | PII(M3) | 45 | 45 | 100 | 92.1 | 100 | 2144.9 | 1707.4 | 2694.4 | 256.0 | 8192.0 |
| | gE/E | PRE | 45 | 45 | 100 | 92.1 | 100 | 597.3 | 452.8 | 787.8 | 128.0 | 8192.0 |
| | | PI(M1) | 45 | 45 | 100 | 92.1 | 100 | 6402.6 | 4799.2 | 8541.8 | 512.0 | 32768.0 |
| | | PI(M2) | 45 | 45 | 100 | 92.1 | 100 | 4356.3 | 3247.0 | 5844.7 | 256.0 | 32768.0 |
| | | PII(M3) | 45 | 45 | 100 | 92.1 | 100 | 10163.5 | 8426.4 | 12258.9 | 1024.0 | 32768.0 |
| | gEVAR/E | PRE | 44 | 44 | 100 | 92.0 | 100 | 783.4 | 620.8 | 988.7 | 128.0 | 4096.0 |
| | | PI(M1) | 44 | 44 | 100 | 92.0 | 100 | 9004.1 | 6946.4 | 11671.3 | 2048.0 | 65536.0 |
| | | PI(M2) | 44 | 44 | 100 | 92.0 | 100 | 6169.4 | 4908.2 | 7754.6 | 2048.0 | 32768.0 |
| | | PII(M3) | 44 | 44 | 100 | 92.0 | 100 | 11225.9 | 9284.5 | 13573.3 | 4096.0 | 32768.0 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years
GMT = geometric mean antibody titre calculated on all subjects
N = number of subjects with available results
n/% = number/percentage of subjects with titre within the specified range
95% CI = 95% confidence interval;
LL = Lower Limit,
UL = Upper Limit
MIN/MAX = Minimum/Maximum
PRE = Pre-vaccination dose 1
PI(M1) = Post-vacciantion dose 1 (Month 1)
PI(M2) = Post-vaccination dose 1 (Month 2)
PII(M3) = Post-vaccination dose 2 (Month 3)

TABLE I.2b

Seroconversion rates for gE antibody titer at each post-vaccination time point (ATP cohort for immunogenicity)

| Group | Timing | N | n | % | 95% CI LL | 95% CI UL |
|---|---|---|---|---|---|---|
| gE/Y | Month 1 | 2 | 2 | 100.0 | 15.8 | 100.0 |
|  | Month 2 | 2 | 2 | 100.0 | 15.8 | 100.0 |
|  | Month 3 | 2 | 2 | 100.0 | 15.8 | 100.0 |
| gEVAR/Y | Month 1 | 3 | 3 | 100.0 | 29.2 | 100.0 |
|  | Month 2 | 3 | 3 | 100.0 | 29.2 | 100.0 |
|  | Month 3 | 3 | 3 | 100.0 | 29.2 | 100.0 |
| VAR/E | Month 1 | 9 | 9 | 100.0 | 66.4 | 100.0 |
|  | Month 2 | 9 | 9 | 100.0 | 66.4 | 100.0 |
|  | Month 3 | 9 | 9 | 100.0 | 66.4 | 100.0 |
| gE/E | Month 1 | 8 | 8 | 100.0 | 63.1 | 100.0 |
|  | Month 2 | 8 | 8 | 100.0 | 63.1 | 100.0 |
|  | Month 3 | 8 | 8 | 100.0 | 63.1 | 100.0 |
| gEVAR/E | Month 1 | 2 | 2 | 100.0 | 15.8 | 100.0 |
|  | Month 2 | 2 | 2 | 100.0 | 15.8 | 100.0 |
|  | Month 3 | 2 | 2 | 100.0 | 15.8 | 100.0 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years
N = number of seronegative subjects at day 0
n/% = number/percentage of initially seronegative subjects who became seropositive at the specified post-vaccination time point
95% CI = 95% confidence interval;
LL = Lower Limit,
UL = Upper Limit TABLE I.3a Vaccine response for VZV antibody titer at each post-vaccination time point (ATP cohort for immunogenicity)

| Group | Timing | N | n | % | 95% CI LL | 95% CI UL |
|---|---|---|---|---|---|---|
| gE/Y | Month 1 | 10 | 7 | 70.0 | 34.8 | 93.3 |
|  | Month 2 | 10 | 6 | 60.0 | 26.2 | 87.8 |
|  | Month 3 | 10 | 9 | 90.0 | 55.5 | 99.7 |
| gEVAR/Y | Month 1 | 10 | 10 | 100.0 | 69.2 | 100.0 |
|  | Month 2 | 10 | 10 | 100.0 | 69.2 | 100.0 |
|  | Month 3 | 10 | 10 | 100.0 | 69.2 | 100.0 |
| VAR/E | Month 1 | 45 | 11 | 24.4 | 12.9 | 39.5 |
|  | Month 2 | 45 | 10 | 22.2 | 11.2 | 37.1 |
|  | Month 3 | 45 | 11 | 24.4 | 12.9 | 39.5 |
| gE/E | Month 1 | 45 | 29 | 64.4 | 48.8 | 78.1 |
|  | Month 2 | 45 | 24 | 53.3 | 37.9 | 68.3 |
|  | Month 3 | 45 | 39 | 86.7 | 73.2 | 94.9 |
| gEVAR/E | Month 1 | 44 | 33 | 75.0 | 59.7 | 86.8 |
|  | Month 2 | 44 | 27 | 61.4 | 45.5 | 75.6 |
|  | Month 3 | 44 | 38 | 86.4 | 72.6 | 94.8 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years
N = number of seropositive subjects at day 0
n/% = number/percentage of initially seropositive subjects with a four-fold increase at the specified post-vaccination time point
95% CI = 95% confidence interval;
LL = Lower Limit,
UL = Upper Limit Analysis of CMI responses is given below

LIST OF TABLES

| | |
|---|---|
| Table C.1 | Intracellular Cytokine Staining (ICS): Descriptive Statistics on CD4 T cells at each time point (Total vaccinated Cohort) . . . |
| Supplementary Table C.1 | Intracellular Cytokine Staining (ICS): Descriptive Statistics on CD8 T cells at each time point (Total vaccinated Cohort) . . . |
| Table C.2 | Intracellular Cytokine Staining (ICS): Inferential statistics: P-values from Kruskal-Wallis Tests for CD4 T cells at each time point (Total Vaccinated Cohort) . . . |
| Supplementary Table C.2 | Intracellular Cytokine Staining (ICS): Inferential statistics: P-values from Kruskal-Wallis Tests for CD8 T cells at each time point (Total vaccinated Cohort) . . . |
| Table C.3 | Intracellular Cytokine Staining (ICS): Descriptive Statistics on CD4 T cells at POST-PRE (Total vaccinated Cohort) . . . |
| Supplementary Table C.3 | Intracellular Cytokine Staining (ICS): Descriptive Statistics on CD8 T cells at POST-PRE (Total vaccinated Cohort) . . . |
| Table C.4 | Intracellular Cytokine Staining (ICS): Inferential statistics: P-values from Kruskal-Wallis Tests for CD4 T cells at POST-PRE (Total Vaccinated Cohort) . . . |
| Supplementary Table C.4 | Intracellular Cytokine Staining (ICS): Inferential statistics: P-values from Kruskal-Wallis Tests for CD8 T cells at POST-PRE (Total vaccinated Cohort) . . . |

TABLE C.1

Intracellular Cytokine Staining (ICS): Descriptive Statistics on CD4 T cells at each time point (Total vaccinated Cohort)

| Test | Antigen | Group | Timing | N | N miss. | Mean | SD | Min | Q1 | Median | Q3 | Max |
|---|---|---|---|---|---|---|---|---|---|---|---|---|
| CD4-ALL DOUBLES | Pool gE | gE/Y | Day 0 | 9 | 1 | 213.44 | 202.59 | 1.00 | 1.00 | 139.00 | 385.00 | 490.00 |
|  |  |  | Month 1 | 9 | 1 | 1383.78 | 1629.94 | 256.00 | 342.00 | 807.00 | 1333.00 | 5207.00 |
|  |  |  | Month 2 | 9 | 1 | 1787.56 | 1818.51 | 497.00 | 677.00 | 919.00 | 1775.00 | 5539.00 |
|  |  |  | Month 3 | 9 | 1 | 2739.89 | 1856.98 | 581.00 | 1770.00 | 2234.00 | 2909.00 | 6963.00 |
|  |  | gEVAR/Y | Day 0 | 10 | 0 | 253.20 | 246.76 | 1.00 | 1.00 | 246.00 | 391.00 | 783.00 |
|  |  |  | Month 1 | 10 | 0 | 1179.70 | 991.68 | 1.00 | 567.00 | 979.00 | 1364.00 | 3535.00 |
|  |  |  | Month 2 | 9 | 1 | 1546.44 | 886.57 | 116.00 | 846.00 | 1996.00 | 2092.00 | 2538.00 |
|  |  |  | Month 3 | 10 | 0 | 3298.50 | 1477.17 | 1699.00 | 1970.00 | 2944.00 | 4924.00 | 5840.00 |
|  |  | VAR/E | Day 0 | 44 | 1 | 299.98 | 922.48 | 1.00 | 1.00 | 126.00 | 238.00 | 6152.00 |
|  |  |  | Month 1 | 43 | 2 | 458.28 | 1256.04 | 1.00 | 89.00 | 194.00 | 294.00 | 8000.00 |

TABLE C.1-continued

Intracellular Cytokine Staining (ICS): Descriptive Statistics on
CD4 T cells at each time point (Total vaccinated Cohort)

| Test | Antigen | Group | Timing | N | N miss. | Mean | SD | Min | Q1 | Median | Q3 | Max |
|---|---|---|---|---|---|---|---|---|---|---|---|---|
| | | | Month 2 | 44 | 1 | 246.09 | 243.71 | 1.00 | 87.50 | 177.00 | 339.00 | 1252.00 |
| | | | Month 3 | 45 | 0 | 476.40 | 1149.12 | 1.00 | 1.00 | 151.00 | 365.00 | 6264.00 |
| | | gE/E | Day 0 | 44 | 1 | 166.27 | 180.38 | 1.00 | 104.50 | 291.50 | 657.00 | |
| | | | Month 1 | 42 | 3 | 849.10 | 1090.91 | 1.00 | 226.00 | 540.00 | 949.00 | 4487.00 |
| | | | Month 2 | 43 | 2 | 522.12 | 577.93 | 1.00 | 115.00 | 402.00 | 627.00 | 2372.00 |
| | | | Month 3 | 43 | 2 | 3221.91 | 2534.70 | 1.00 | 1184.00 | 2323.00 | 4767.00 | 11480.00 |
| | | gEVAR/E | Day 0 | 45 | 0 | 206.02 | 265.71 | 1.00 | 36.00 | 158.00 | 249.00 | 1552.00 |
| | | | Month 1 | 44 | 1 | 826.70 | 614.40 | 1.00 | 322.50 | 770.00 | 1158.50 | 2927.00 |
| | | | Month 2 | 45 | 0 | 509.16 | 411.89 | 1.00 | 166.00 | 447.00 | 737.00 | 1553.00 |
| | | | Month 3 | 45 | 0 | 2918.04 | 2522.39 | 8.00 | 1081.00 | 1902.00 | 4251.00 | 10468.00 |
| | Varilrix | gE/Y | Day 0 | 9 | 1 | 1045.78 | 770.48 | 369.00 | 544.00 | 761.00 | 1067.00 | 2590.00 |
| | | | Month 1 | 9 | 1 | 1302.67 | 1378.05 | 1.00 | 314.00 | 597.00 | 1877.00 | 4109.00 |
| | | | Month 2 | 9 | 1 | 1656.00 | 1224.33 | 561.00 | 890.00 | 1238.00 | 2019.00 | 4494.00 |
| | | | Month 3 | 9 | 1 | 1816.33 | 994.51 | 590.00 | 1241.00 | 1368.00 | 2540.00 | 3755.00 |
| | | gEVAR/Y | Day 0 | 10 | 0 | 1188.40 | 580.19 | 412.00 | 783.00 | 1058.50 | 1535.00 | 2332.00 |
| | | | Month 1 | 10 | 0 | 1090.00 | 1168.31 | 1.00 | 610.00 | 770.00 | 1123.00 | 4267.00 |
| | | | Month 2 | 9 | 1 | 2659.78 | 1316.29 | 873.00 | 1868.00 | 2282.00 | 4171.00 | 4246.00 |
| | | | Month 3 | 10 | 0 | 3369.70 | 2127.99 | 1147.00 | 1738.00 | 2854.50 | 4494.00 | 7745.00 |
| | | VAR/E | Day 0 | 44 | 1 | 581.02 | 635.92 | 1.00 | 129.50 | 415.00 | 753.50 | 3327.00 |
| | | | Month 1 | 43 | 2 | 992.35 | 1093.91 | 1.00 | 268.00 | 661.00 | 1447.00 | 5359.00 |
| | | | Month 2 | 44 | 1 | 815.75 | 928.07 | 1.00 | 222.50 | 517.00 | 1065.00 | 4575.00 |
| | | | Month 3 | 45 | 0 | 984.67 | 832.16 | 1.00 | 364.00 | 774.00 | 1278.00 | 3287.00 |
| | | gE/E | Day 0 | 44 | 1 | 758.18 | 982.52 | 1.00 | 81.50 | 395.00 | 929.50 | 4479.00 |
| | | | Month 1 | 42 | 3 | 1216.60 | 1674.07 | 1.00 | 307.00 | 591.00 | 1410.00 | 7779.00 |
| | | | Month 2 | 43 | 2 | 869.35 | 1017.90 | 1.00 | 217.00 | 543.00 | 1072.00 | 4556.00 |
| | | | Month 3 | 43 | 2 | 2192.42 | 1977.14 | 56.00 | 840.00 | 1862.00 | 2557.00 | 9167.00 |
| | | gEVAR/E | Day 0 | 45 | 0 | 510.73 | 512.13 | 1.00 | 219.00 | 376.00 | 675.00 | 2218.00 |
| | | | Month 1 | 44 | 1 | 1179.50 | 1005.41 | 1.00 | 434.50 | 982.00 | 1529.00 | 4478.00 |
| | | | Month 2 | 45 | 0 | 961.78 | 915.99 | 1.00 | 292.00 | 704.00 | 1078.00 | 3975.00 |
| | | | Month 3 | 45 | 0 | 2484.47 | 1713.46 | 109.00 | 1270.00 | 2008.00 | 3429.00 | 6585.00 |
| CD4-CD40L | Pool gE | gE/Y | Day 0 | 9 | 1 | 204.67 | 193.66 | 1.00 | 1.00 | 139.00 | 356.00 | 490.00 |
| | | | Month 1 | 9 | 1 | 1347.33 | 1570.63 | 244.00 | 400.00 | 768.00 | 1273.00 | 5021.00 |
| | | | Month 2 | 9 | 1 | 1724.44 | 1737.59 | 466.00 | 660.00 | 869.00 | 1859.00 | 5252.00 |
| | | | Month 3 | 9 | 1 | 2567.89 | 1723.12 | 514.00 | 1744.00 | 1905.00 | 2813.00 | 6414.00 |
| | | gEVAR/Y | Day 0 | 10 | 0 | 253.80 | 240.23 | 1.00 | 41.00 | 265.50 | 361.00 | 752.00 |
| | | | Month 1 | 10 | 0 | 1122.30 | 999.38 | 1.00 | 480.00 | 948.00 | 1266.00 | 3534.00 |
| | | | Month 2 | 9 | 1 | 1520.33 | 898.50 | 116.00 | 732.00 | 2045.00 | 2068.00 | 2633.00 |
| | | | Month 3 | 10 | 0 | 3169.30 | 1452.28 | 1555.00 | 1857.00 | 2910.50 | 4539.00 | 5840.00 |
| | | VAR/E | Day 0 | 44 | 1 | 292.50 | 872.61 | 1.00 | 1.00 | 119.50 | 238.50 | 5812.00 |
| | | | Month 1 | 43 | 2 | 444.93 | 1175.20 | 1.00 | 70.00 | 214.00 | 316.00 | 7453.00 |
| | | | Month 2 | 44 | 1 | 242.66 | 242.66 | 1.00 | 95.00 | 178.00 | 333.00 | 1252.00 |
| | | | Month 3 | 45 | 0 | 465.67 | 1124.33 | 1.00 | 18.00 | 154.00 | 365.00 | 6072.00 |
| | | gE/E | Day 0 | 44 | 1 | 158.55 | 173.14 | 1.00 | 5.50 | 98.50 | 290.50 | 564.00 |
| | | | Month 1 | 42 | 3 | 840.79 | 1061.43 | 1.00 | 237.00 | 530.00 | 910.00 | 4428.00 |
| | | | Month 2 | 43 | 2 | 529.58 | 558.23 | 1.00 | 147.00 | 365.00 | 645.00 | 2251.00 |
| | | | Month 3 | 43 | 2 | 3133.65 | 2453.67 | 1.00 | 1172.00 | 2294.00 | 4703.00 | 10561.00 |
| | | gEVAR/E | Day 0 | 45 | 0 | 206.16 | 257.80 | 1.00 | 35.00 | 167.00 | 278.00 | 1525.00 |
| | | | Month 1 | 44 | 1 | 814.57 | 606.93 | 1.00 | 314.00 | 773.00 | 1153.00 | 2762.00 |
| | | | Month 2 | 45 | 0 | 515.11 | 400.69 | 1.00 | 204.00 | 459.00 | 737.00 | 1523.00 |
| | | | Month 3 | 45 | 0 | 2898.40 | 2512.50 | 97.00 | 1073.00 | 1915.00 | 4200.00 | 10418.00 |
| | Varilrix | gE/Y | Day 0 | 9 | 1 | 1027.78 | 746.06 | 373.00 | 544.00 | 761.00 | 1033.00 | 2507.00 |
| | | | Month 1 | 9 | 1 | 1264.11 | 1345.95 | 1.00 | 277.00 | 554.00 | 1854.00 | 3992.00 |
| | | | Month 2 | 9 | 1 | 1609.67 | 1112.38 | 561.00 | 978.00 | 1238.00 | 1992.00 | 4094.00 |
| | | | Month 3 | 9 | 1 | 1750.67 | 987.16 | 573.00 | 1039.00 | 1329.00 | 2556.00 | 3598.00 |
| | | gEVAR/Y | Day 0 | 10 | 0 | 1174.60 | 581.33 | 379.00 | 747.00 | 1061.50 | 1535.00 | 2327.00 |
| | | | Month 1 | 10 | 0 | 1051.70 | 1159.05 | 1.00 | 610.00 | 706.50 | 1019.00 | 4211.00 |
| | | | Month 2 | 9 | 1 | 2623.56 | 1344.14 | 873.00 | 1726.00 | 2281.00 | 4168.00 | 4273.00 |
| | | | Month 3 | 10 | 0 | 3229.20 | 2099.64 | 1089.00 | 1624.00 | 2797.00 | 4400.00 | 7592.00 |
| | | VAR/E | Day 0 | 44 | 1 | 574.57 | 617.51 | 1.00 | 129.50 | 410.00 | 785.50 | 3268.00 |
| | | | Month 1 | 43 | 2 | 976.98 | 1068.41 | 1.00 | 282.00 | 661.00 | 1386.00 | 5305.00 |
| | | | Month 2 | 44 | 1 | 801.14 | 922.73 | 1.00 | 230.50 | 519.50 | 1044.00 | 4601.00 |
| | | | Month 3 | 45 | 0 | 965.73 | 817.64 | 1.00 | 409.00 | 733.00 | 1255.00 | 3264.00 |
| | | gE/E | Day 0 | 44 | 1 | 742.41 | 978.83 | 1.00 | 85.00 | 367.50 | 906.00 | 4506.00 |
| | | | Month 1 | 42 | 3 | 1184.31 | 1577.03 | 1.00 | 307.00 | 608.00 | 1410.00 | 7748.00 |
| | | | Month 2 | 43 | 2 | 868.70 | 1000.52 | 2.00 | 195.00 | 521.00 | 1020.00 | 4435.00 |
| | | | Month 3 | 43 | 2 | 2143.84 | 1963.92 | 64.00 | 840.00 | 1849.00 | 2508.00 | 9008.00 |
| | | gEVAR/E | Day 0 | 45 | 0 | 506.91 | 508.06 | 1.00 | 177.00 | 367.00 | 586.00 | 2191.00 |
| | | | Month 1 | 44 | 1 | 1172.11 | 1005.52 | 19.00 | 452.00 | 949.50 | 1507.50 | 4478.00 |
| | | | Month 2 | 45 | 0 | 963.98 | 907.43 | 7.00 | 325.00 | 680.00 | 1091.00 | 3975.00 |
| | | | Month 3 | 45 | 0 | 2438.44 | 1675.69 | 73.00 | 1239.00 | 2008.00 | 3372.00 | 6538.00 |
| CD4-IFNγ | Pool gE | gE/Y | Day 0 | 9 | 1 | 111.00 | 101.80 | 1.00 | 1.00 | 104.00 | 154.00 | 295.00 |
| | | | Month 1 | 9 | 1 | 966.89 | 1288.87 | 1.00 | 212.00 | 499.00 | 824.00 | 3972.00 |
| | | | Month 2 | 9 | 1 | 1263.67 | 1422.73 | 193.00 | 498.00 | 665.00 | 1298.00 | 4705.00 |
| | | | Month 3 | 9 | 1 | 1952.44 | 1798.75 | 358.00 | 1189.00 | 1302.00 | 2103.00 | 6292.00 |

TABLE C.1-continued

Intracellular Cytokine Staining (ICS): Descriptive Statistics on
CD4 T cells at each time point (Total vaccinated Cohort)

| Test | Antigen | Group | Timing | N | N miss. | Mean | SD | Min | Q1 | Median | Q3 | Max |
|---|---|---|---|---|---|---|---|---|---|---|---|---|
| | | gEVAR/Y | Day 0 | 10 | 0 | 177.30 | 118.58 | 24.00 | 112.00 | 138.00 | 242.00 | 437.00 |
| | | | Month 1 | 10 | 0 | 823.50 | 948.60 | 1.00 | 272.00 | 591.00 | 851.00 | 3334.00 |
| | | | Month 2 | 9 | 1 | 1087.22 | 751.60 | 39.00 | 503.00 | 1290.00 | 1626.00 | 2226.00 |
| | | | Month 3 | 10 | 0 | 2285.60 | 1272.75 | 1146.00 | 1243.00 | 1967.00 | 2691.00 | 5437.00 |
| | | VAR/E | Day 0 | 44 | 1 | 174.95 | 478.34 | 1.00 | 29.50 | 54.50 | 154.00 | 3179.00 |
| | | | Month 1 | 43 | 2 | 290.14 | 764.08 | 1.00 | 47.00 | 92.00 | 220.00 | 4988.00 |
| | | | Month 2 | 44 | 1 | 172.70 | 201.53 | 1.00 | 40.50 | 117.00 | 216.00 | 1105.00 |
| | | | Month 3 | 45 | 0 | 279.49 | 586.44 | 1.00 | 1.00 | 100.00 | 193.00 | 3226.00 |
| | | gE/E | Day 0 | 44 | 1 | 128.91 | 150.94 | 1.00 | 10.50 | 75.50 | 197.00 | 586.00 |
| | | | Month 1 | 42 | 3 | 513.38 | 768.05 | 1.00 | 55.00 | 250.00 | 520.00 | 3471.00 |
| | | | Month 2 | 43 | 2 | 293.86 | 414.90 | 1.00 | 48.00 | 144.00 | 333.00 | 1894.00 |
| | | | Month 3 | 43 | 2 | 1672.33 | 1602.24 | 1.00 | 596.00 | 1307.00 | 2104.00 | 6309.00 |
| | | gEVAR/E | Day 0 | 45 | 0 | 123.78 | 173.17 | 1.00 | 36.00 | 76.00 | 159.00 | 1078.00 |
| | | | Month 1 | 44 | 1 | 474.86 | 405.90 | 1.00 | 161.00 | 326.00 | 746.50 | 1536.00 |
| | | | Month 2 | 45 | 0 | 295.87 | 316.87 | 1.00 | 68.00 | 190.00 | 425.00 | 1132.00 |
| | | | Month 3 | 45 | 0 | 1516.18 | 1303.21 | 67.00 | 620.00 | 1024.00 | 2188.00 | 5829.00 |
| | Varilrix | gE/Y | Day 0 | 9 | 1 | 855.44 | 722.82 | 310.00 | 391.00 | 577.00 | 839.00 | 2466.00 |
| | | | Month 1 | 9 | 1 | 1051.89 | 1228.06 | 1.00 | 247.00 | 384.00 | 1462.00 | 3637.00 |
| | | | Month 2 | 9 | 1 | 1283.67 | 1065.12 | 410.00 | 475.00 | 966.00 | 1482.00 | 3808.00 |
| | | | Month 3 | 9 | 1 | 1362.44 | 910.53 | 448.00 | 833.00 | 1045.00 | 1873.00 | 3297.00 |
| | | gEVAR/Y | Day 0 | 10 | 0 | 946.70 | 536.60 | 438.00 | 548.00 | 822.50 | 1097.00 | 2162.00 |
| | | | Month 1 | 10 | 0 | 921.30 | 1143.99 | 1.00 | 365.00 | 586.00 | 1047.00 | 4042.00 |
| | | | Month 2 | 9 | 1 | 2176.56 | 1249.74 | 838.00 | 1181.00 | 1711.00 | 3439.00 | 3885.00 |
| | | | Month 3 | 10 | 0 | 2715.60 | 1892.41 | 716.00 | 1327.00 | 2380.50 | 3836.00 | 6992.00 |
| | | VAR/E | Day 0 | 44 | 1 | 481.73 | 550.51 | 1.00 | 95.50 | 367.50 | 600.00 | 2960.00 |
| | | | Month 1 | 43 | 2 | 827.30 | 941.73 | 1.00 | 253.00 | 529.00 | 1287.00 | 4765.00 |
| | | | Month 2 | 44 | 1 | 641.86 | 757.75 | 3.00 | 160.00 | 444.50 | 797.50 | 3922.00 |
| | | | Month 3 | 45 | 0 | 772.67 | 690.72 | 1.00 | 244.00 | 580.00 | 1003.00 | 2797.00 |
| | | gE/E | Day 0 | 44 | 1 | 629.98 | 847.28 | 1.00 | 72.50 | 228.00 | 819.00 | 3920.00 |
| | | | Month 1 | 42 | 3 | 972.52 | 1380.48 | 1.00 | 186.00 | 419.00 | 1154.00 | 6695.00 |
| | | | Month 2 | 43 | 2 | 673.05 | 857.44 | 1.00 | 137.00 | 371.00 | 730.00 | 4126.00 |
| | | | Month 3 | 43 | 2 | 1581.98 | 1625.99 | 58.00 | 618.00 | 1381.00 | 1735.00 | 7796.00 |
| | | gEVAR/E | Day 0 | 45 | 0 | 386.82 | 395.99 | 1.00 | 92.00 | 263.00 | 483.00 | 1579.00 |
| | | | Month 1 | 44 | 1 | 937.20 | 879.65 | 1.00 | 338.50 | 656.50 | 1132.50 | 3637.00 |
| | | | Month 2 | 45 | 0 | 786.73 | 775.90 | 1.00 | 343.00 | 566.00 | 901.00 | 3205.00 |
| | | | Month 3 | 45 | 0 | 1769.78 | 1236.32 | 1.00 | 884.00 | 1439.00 | 2289.00 | 4992.00 |
| CD4-IL2 | Pool gE | gE/Y | Day 0 | 9 | 1 | 166.44 | 178.37 | 1.00 | 1.00 | 66.00 | 337.00 | 420.00 |
| | | | Month 1 | 9 | 1 | 1259.44 | 1464.99 | 240.00 | 371.00 | 768.00 | 1119.00 | 4701.00 |
| | | | Month 2 | 9 | 1 | 1662.11 | 1698.78 | 402.00 | 593.00 | 892.00 | 1721.00 | 5076.00 |
| | | | Month 3 | 9 | 1 | 2317.67 | 1497.67 | 410.00 | 1423.00 | 2011.00 | 2595.00 | 5534.00 |
| | | gEVAR/Y | Day 0 | 10 | 0 | 237.20 | 233.77 | 1.00 | 50.00 | 231.00 | 349.00 | 751.00 |
| | | | Month 1 | 10 | 0 | 987.90 | 796.31 | 1.00 | 509.00 | 751.50 | 1361.00 | 2799.00 |
| | | | Month 2 | 9 | 1 | 1404.67 | 723.26 | 270.00 | 802.00 | 1905.00 | 1975.00 | 2029.00 |
| | | | Month 3 | 10 | 0 | 2747.80 | 1210.11 | 1436.00 | 1563.00 | 2367.50 | 4296.00 | 4451.00 |
| | | VAR/E | Day 0 | 44 | 1 | 269.98 | 833.31 | 1.00 | 33.00 | 119.00 | 212.00 | 5582.00 |
| | | | Month 1 | 43 | 2 | 388.26 | 995.89 | 1.00 | 58.00 | 164.00 | 293.00 | 6248.00 |
| | | | Month 2 | 44 | 1 | 211.18 | 231.64 | 1.00 | 53.50 | 158.00 | 286.50 | 1182.00 |
| | | | Month 3 | 45 | 0 | 397.51 | 916.41 | 1.00 | 2.00 | 146.00 | 329.00 | 4728.00 |
| | | gE/E | Day 0 | 44 | 1 | 149.86 | 153.06 | 1.00 | 9.50 | 95.50 | 252.00 | 550.00 |
| | | | Month 1 | 42 | 3 | 761.98 | 992.38 | 5.00 | 157.00 | 451.50 | 800.00 | 4039.00 |
| | | | Month 2 | 43 | 2 | 467.58 | 523.51 | 1.00 | 103.00 | 329.00 | 541.00 | 2094.00 |
| | | | Month 3 | 43 | 2 | 2809.07 | 2307.31 | 1.00 | 1037.00 | 2177.00 | 4347.00 | 10316.00 |
| | | gEVAR/E | Day 0 | 45 | 0 | 165.16 | 246.51 | 1.00 | 35.00 | 116.00 | 203.00 | 1551.00 |
| | | | Month 1 | 44 | 1 | 712.59 | 540.93 | 1.00 | 228.00 | 728.50 | 1048.00 | 2381.00 |
| | | | Month 2 | 45 | 0 | 465.58 | 354.74 | 1.00 | 184.00 | 385.00 | 667.00 | 1239.00 |
| | | | Month 3 | 45 | 0 | 2550.27 | 2304.36 | 1.00 | 945.00 | 1713.00 | 3910.00 | 9561.00 |
| | Varilrix | gE/Y | Day 0 | 9 | 1 | 941.44 | 645.88 | 446.00 | 492.00 | 617.00 | 967.00 | 2217.00 |
| | | | Month 1 | 9 | 1 | 1092.22 | 1164.69 | 1.00 | 249.00 | 469.00 | 1576.00 | 3480.00 |
| | | | Month 2 | 9 | 1 | 1482.00 | 1067.28 | 393.00 | 906.00 | 1148.00 | 1715.00 | 3938.00 |
| | | | Month 3 | 9 | 1 | 1551.22 | 851.75 | 484.00 | 869.00 | 1275.00 | 2083.00 | 3112.00 |
| | | gEVAR/Y | Day 0 | 10 | 0 | 1074.70 | 505.73 | 414.00 | 748.00 | 988.00 | 1265.00 | 2094.00 |
| | | | Month 1 | 10 | 0 | 903.00 | 887.48 | 1.00 | 486.00 | 650.50 | 880.00 | 3256.00 |
| | | | Month 2 | 9 | 1 | 2403.33 | 1122.05 | 989.00 | 1679.00 | 2086.00 | 3309.00 | 4127.00 |
| | | | Month 3 | 10 | 0 | 2791.90 | 1716.41 | 1043.00 | 1472.00 | 2186.50 | 3978.00 | 6004.00 |
| | | VAR/E | Day 0 | 44 | 1 | 536.80 | 592.24 | 1.00 | 135.50 | 403.50 | 710.00 | 3190.00 |
| | | | Month 1 | 43 | 2 | 866.63 | 984.53 | 1.00 | 220.00 | 608.00 | 1154.00 | 4813.00 |
| | | | Month 2 | 44 | 1 | 711.09 | 830.59 | 1.00 | 204.50 | 452.50 | 907.50 | 4261.00 |
| | | | Month 3 | 45 | 0 | 828.55 | 733.60 | 1.00 | 331.00 | 632.00 | 1076.00 | 2948.00 |
| | | gE/E | Day 0 | 44 | 1 | 701.02 | 866.81 | 1.00 | 97.50 | 280.00 | 885.50 | 3493.00 |
| | | | Month 1 | 42 | 3 | 1076.55 | 1440.99 | 1.00 | 233.00 | 548.00 | 1316.00 | 6726.00 |
| | | | Month 2 | 43 | 2 | 785.88 | 884.51 | 1.00 | 167.00 | 515.00 | 971.00 | 3707.00 |
| | | | Month 3 | 43 | 2 | 1866.37 | 1721.01 | 1.00 | 670.00 | 1569.00 | 2295.00 | 7835.00 |
| | | gEVAR/E | Day 0 | 45 | 0 | 465.67 | 489.70 | 1.00 | 142.00 | 334.00 | 557.00 | 2107.00 |
| | | | Month 1 | 44 | 1 | 1056.59 | 942.76 | 18.00 | 441.50 | 802.00 | 1408.50 | 4071.00 |

TABLE C.1-continued

Intracellular Cytokine Staining (ICS): Descriptive Statistics on CD4 T cells at each time point (Total vaccinated Cohort)

| Test | Antigen | Group | Timing | N | N miss. | Mean | SD | Min | Q1 | Median | Q3 | Max |
|---|---|---|---|---|---|---|---|---|---|---|---|---|
| | | | Month 2 | 45 | 0 | 885.89 | 853.16 | 1.00 | 328.00 | 628.00 | 1013.00 | 3815.00 |
| | | | Month 3 | 45 | 0 | 2114.20 | 1524.74 | 72.00 | 993.00 | 1660.00 | 3199.00 | 5671.00 |
| CD4-TNFα | Pool gE | gE/Y | Day 0 | 9 | 1 | 99.33 | 94.45 | 1.00 | 32.00 | 68.00 | 189.00 | 245.00 |
| | | | Month 1 | 9 | 1 | 659.56 | 926.82 | 114.00 | 155.00 | 201.00 | 757.00 | 2960.00 |
| | | | Month 2 | 9 | 1 | 891.11 | 1360.20 | 71.00 | 261.00 | 347.00 | 868.00 | 4435.00 |
| | | | Month 3 | 9 | 1 | 1423.33 | 1570.82 | 238.00 | 494.00 | 914.00 | 1350.00 | 5269.00 |
| | | gEVAR/Y | Day 0 | 10 | 0 | 117.00 | 157.25 | 1.00 | 1.00 | 28.00 | 265.00 | 380.00 |
| | | | Month 1 | 10 | 0 | 649.30 | 523.37 | 34.00 | 352.00 | 551.00 | 805.00 | 1952.00 |
| | | | Month 2 | 9 | 1 | 804.67 | 520.96 | 39.00 | 504.00 | 717.00 | 1191.00 | 1578.00 |
| | | | Month 3 | 10 | 0 | 1770.00 | 890.04 | 470.00 | 1223.00 | 1865.00 | 2258.00 | 3054.00 |
| | | VAR/E | Day 0 | 44 | 1 | 211.11 | 697.05 | 1.00 | 1.00 | 73.00 | 158.00 | 4652.00 |
| | | | Month 1 | 43 | 2 | 271.98 | 755.07 | 1.00 | 43.00 | 109.00 | 217.00 | 4812.00 |
| | | | Month 2 | 44 | 1 | 149.80 | 172.34 | 1.00 | 38.50 | 109.00 | 233.00 | 1007.00 |
| | | | Month 3 | 45 | 0 | 291.98 | 713.57 | 1.00 | 1.00 | 108.00 | 198.00 | 4213.00 |
| | | gE/E | Day 0 | 44 | 1 | 125.23 | 143.92 | 1.00 | 1.00 | 54.00 | 213.00 | 531.00 |
| | | | Month 1 | 42 | 3 | 444.05 | 585.76 | 1.00 | 64.00 | 283.50 | 473.00 | 2574.00 |
| | | | Month 2 | 43 | 2 | 319.30 | 371.77 | 1.00 | 103.00 | 225.00 | 425.00 | 1808.00 |
| | | | Month 3 | 43 | 2 | 1902.56 | 1602.67 | 1.00 | 779.00 | 1414.00 | 2860.00 | 7655.00 |
| | | gEVAR/E | Day 0 | 45 | 0 | 153.76 | 193.78 | 1.00 | 33.00 | 129.00 | 190.00 | 1025.00 |
| | | | Month 1 | 44 | 1 | 432.39 | 326.71 | 1.00 | 135.50 | 410.50 | 694.50 | 1479.00 |
| | | | Month 2 | 45 | 0 | 318.69 | 273.85 | 1.00 | 96.00 | 265.00 | 438.00 | 1097.00 |
| | | | Month 3 | 45 | 0 | 1662.40 | 1570.03 | 1.00 | 671.00 | 1091.00 | 2194.00 | 6609.00 |
| | Varilrix | gE/Y | Day 0 | 9 | 1 | 754.44 | 694.51 | 260.00 | 286.00 | 315.00 | 902.00 | 2217.00 |
| | | | Month 1 | 9 | 1 | 812.11 | 925.84 | 1.00 | 131.00 | 370.00 | 1275.00 | 2851.00 |
| | | | Month 2 | 9 | 1 | 1204.56 | 980.05 | 420.00 | 690.00 | 738.00 | 1436.00 | 3581.00 |
| | | | Month 3 | 9 | 1 | 1129.33 | 872.35 | 286.00 | 592.00 | 719.00 | 1539.00 | 2972.00 |
| | | gEVAR/Y | Day 0 | 10 | 0 | 816.50 | 449.18 | 239.00 | 597.00 | 733.00 | 1024.00 | 1577.00 |
| | | | Month 1 | 10 | 0 | 660.20 | 520.39 | 217.00 | 342.00 | 482.50 | 895.00 | 1965.00 |
| | | | Month 2 | 9 | 1 | 1789.67 | 952.77 | 418.00 | 1084.00 | 1396.00 | 2627.00 | 3273.00 |
| | | | Month 3 | 10 | 0 | 2016.50 | 1220.42 | 437.00 | 1321.00 | 1774.00 | 3179.00 | 4156.00 |
| | | VAR/E | Day 0 | 44 | 1 | 467.02 | 590.33 | 1.00 | 86.50 | 303.00 | 607.50 | 3075.00 |
| | | | Month 1 | 43 | 2 | 751.72 | 934.46 | 1.00 | 223.00 | 405.00 | 1079.00 | 4794.00 |
| | | | Month 2 | 44 | 1 | 638.30 | 813.04 | 1.00 | 215.50 | 340.00 | 812.00 | 3974.00 |
| | | | Month 3 | 45 | 0 | 711.04 | 662.11 | 1.00 | 268.00 | 535.00 | 865.00 | 2893.00 |
| | | gE/E | Day 0 | 44 | 1 | 623.09 | 800.32 | 1.00 | 96.50 | 257.50 | 833.50 | 3426.01 |
| | | | Month 1 | 42 | 3 | 862.48 | 1203.33 | 1.00 | 197.00 | 389.00 | 1091.00 | 5641.01 |
| | | | Month 2 | 43 | 2 | 664.63 | 820.99 | 22.00 | 142.00 | 334.00 | 845.00 | 3582.01 |
| | | | Month 3 | 43 | 2 | 1508.67 | 1419.81 | 1.00 | 537.00 | 1353.00 | 1836.00 | 6451.01 |
| | | gEVAR/E | Day 0 | 45 | 0 | 405.42 | 379.35 | 1.00 | 168.00 | 260.00 | 558.00 | 1616.01 |
| | | | Month 1 | 44 | 1 | 814.70 | 780.82 | 1.00 | 274.50 | 574.50 | 989.00 | 3311.01 |
| | | | Month 2 | 45 | 0 | 699.20 | 628.49 | 1.00 | 232.00 | 549.00 | 898.00 | 2501.01 |
| | | | Month 3 | 45 | 0 | 1634.80 | 1160.30 | 73.00 | 854.00 | 1450.00 | 2097.00 | 4405.01 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years
N = number of subjects with available results
N miss. = number of subjects with missing results
SD = Standard Deviation
Min, Max = Minimum, Maximum
Q1, Q3 = First, Third quartile

SUPPLEMENTARY TABLE C.1

Intracellular Cytokine Staining (ICS): Descriptive Statistics on CD8 T cells at each time point (Total vaccinated Cohort)

| Test | Antigen | Group | Timing | N | N miss. | Mean | SD | MM | Q1 | Median | Q3 | Max |
|---|---|---|---|---|---|---|---|---|---|---|---|---|
| CD8-ALL DOUBLES | Pool gE | gE/Y | Day 0 | 9 | 1 | 37.78 | 48.76 | 1.00 | 1.00 | 1.00 | 68.00 | 137.00 |
| | | | Month 1 | 9 | 1 | 61.78 | 111.15 | 1.00 | 1.00 | 68.00 | 345.00 | |
| | | | Month 2 | 9 | 1 | 587.67 | 1585.68 | 1.00 | 1.00 | 1.00 | 137.00 | 4811.00 |
| | | | Month 3 | 9 | 1 | 38.67 | 50.04 | 1.00 | 1.00 | 1.00 | 67.00 | 141.00 |
| | | gEVAR/Y | Day 0 | 10 | 0 | 151.00 | 246.45 | 1.00 | 1.00 | 35.00 | 206.00 | 742.00 |
| | | | Month 1 | 10 | 0 | 34.30 | 65.70 | 1.00 | 1.00 | 1.00 | 64.00 | 205.00 |
| | | | Month 2 | 9 | 1 | 39.00 | 114.00 | 1.00 | 1.00 | 1.00 | 1.00 | 343.00 |
| | | | Month 3 | 10 | 0 | 177.80 | 313.49 | 1.00 | 1.00 | 36.00 | 272.00 | 1013.00 |
| | | VAR/E | Day 0 | 44 | 1 | 40.32 | 79.95 | 1.00 | 1.00 | 1.00 | 68.00 | 348.00 |
| | | | Month 1 | 43 | 2 | 33.16 | 59.81 | 1.00 | 1.00 | 1.00 | 72.00 | 216.00 |
| | | | Month 2 | 43 | 2 | 41.14 | 75.20 | 1.00 | 1.00 | 1.00 | 70.00 | 284.00 |
| | | | Month 3 | 45 | 0 | 29.20 | 62.99 | 1.00 | 1.00 | 1.00 | 1.00 | 286.00 |

SUPPLEMENTARY TABLE C.1-continued

Intracellular Cytokine Staining (ICS): Descriptive
Statistics on CD8 T cells at each time point (Total vaccinated Cohort)

| Test | Antigen | Group | Timing | N | N miss. | Mean | SD | MM | Q1 | Median | Q3 | Max |
|---|---|---|---|---|---|---|---|---|---|---|---|---|
| | | gE/E | Day 0 | 44 | 1 | 23.64 | 50.66 | 1.00 | 1.00 | 1.00 | 1.00 | 221.00 |
| | | | Month 1 | 42 | 3 | 35.17 | 82.74 | 1.00 | 1.00 | 1.00 | 28.00 | 422.00 |
| | | | Month 2 | 43 | 2 | 45.02 | 72.29 | 1.00 | 1.00 | 1.00 | 73.00 | 368.00 |
| | | | Month 3 | 43 | 2 | 34.74 | 86.80 | 1.00 | 1.00 | 1.00 | 1.00 | 461.00 |
| | | gEVAR/E | Day 0 | 43 | 2 | 15.58 | 39.75 | 1.00 | 1.00 | 1.00 | 1.00 | 220.00 |
| | | | Month 1 | 44 | 1 | 40.25 | 63.63 | 1.00 | 1.00 | 1.00 | 70.50 | 296.00 |
| | | | Month 2 | 45 | 0 | 30.38 | 55.59 | 1.00 | 1.00 | 1.00 | 68.00 | 267.00 |
| | | | Month 3 | 45 | 0 | 77.04 | 205.13 | 1.00 | 1.00 | 1.00 | 71.00 | 1135.00 |
| | Varilrix | gE/Y | Day 0 | 9 | 1 | 506.11 | 1386.23 | 1.00 | 1.00 | 2.00 | 69.00 | 4198.00 |
| | | | Month 1 | 9 | 1 | 594.89 | 1659.25 | 1.00 | 1.00 | 1.00 | 120.00 | 5015.00 |
| | | | Month 2 | 9 | 1 | 990.22 | 2761.19 | 1.00 | 1.00 | 68.00 | 136.00 | 8351.00 |
| | | | Month 3 | 9 | 1 | 419.33 | 1152.89 | 1.00 | 1.00 | 1.00 | 71.00 | 3491.00 |
| | | gEVAR/Y | Day 0 | 10 | 0 | 42.30 | 68.03 | 1.00 | 1.00 | 1.00 | 67.00 | 214.00 |
| | | | Month 1 | 10 | 0 | 21.50 | 45.55 | 1.00 | 1.00 | 1.00 | 1.00 | 134.00 |
| | | | Month 2 | 9 | 1 | 77.33 | 105.58 | 1.00 | 1.00 | 1.00 | 142.00 | 274.00 |
| | | | Month 3 | 10 | 0 | 98.40 | 149.12 | 1.00 | 1.00 | 37.00 | 141.00 | 481.00 |
| | | VAR/E | Day 0 | 44 | 1 | 228.18 | 753.26 | 1.00 | 1.00 | 1.00 | 138.00 | 4822.00 |
| | | | Month 1 | 43 | 2 | 205.77 | 502.36 | 1.00 | 1.00 | 70.00 | 149.00 | 3021.00 |
| | | | Month 2 | 44 | 1 | 191.41 | 509.66 | 1.00 | 1.00 | 34.00 | 136.00 | 3158.00 |
| | | | Month 3 | 45 | 0 | 356.69 | 1417.74 | 1.00 | 1.00 | 70.00 | 170.00 | 9496.00 |
| | | gE/E | Day 0 | 44 | 1 | 244.86 | 491.44 | 1.00 | 1.00 | 71.50 | 224.50 | 2300.00 |
| | | | Month 1 | 42 | 3 | 279.14 | 611.61 | 1.00 | 1.00 | 68.00 | 225.00 | 2909.00 |
| | | | Month 2 | 43 | 2 | 236.79 | 551.54 | 1.00 | 1.00 | 66.00 | 225.00 | 2663.00 |
| | | | Month 3 | 43 | 2 | 245.67 | 489.68 | 1.00 | 1.00 | 71.00 | 201.00 | 2491.00 |
| | | gEVAR/E | Day 0 | 43 | 2 | 159.93 | 381.14 | 1.00 | 1.00 | 1.00 | 130.00 | 2072.00 |
| | | | Month 1 | 44 | 1 | 188.82 | 311.58 | 1.00 | 1.00 | 69.50 | 217.00 | 1398.00 |
| | | | Month 2 | 45 | 0 | 223.47 | 517.02 | 1.00 | 1.00 | 1.00 | 212.00 | 2491.00 |
| | | | Month 3 | 45 | 0 | 304.16 | 520.03 | 1.00 | 1.00 | 143.00 | 290.00 | 2487.00 |
| CD8-CD40L | Pool gE | gE/Y | Day 0 | 9 | 1 | 30.11 | 34.57 | 1.00 | 1.00 | 1.00 | 68.00 | 68.00 |
| | | | Month 1 | 9 | 1 | 54.22 | 112.89 | 1.00 | 1.00 | 1.00 | 67.00 | 345.00 |
| | | | Month 2 | 9 | 1 | 565.11 | 1593.60 | 1.00 | 1.00 | 1.00 | 68.00 | 4811.00 |
| | | | Month 3 | 9 | 1 | 16.22 | 30.21 | 1.00 | 1.00 | 1.00 | 1.00 | 70.00 |
| | | gEVAR/Y | Day 0 | 10 | 0 | 130.10 | 235.43 | 1.00 | 1.00 | 1.00 | 206.00 | 674.00 |
| | | | Month 1 | 10 | 0 | 34.30 | 65.70 | 1.00 | 1.00 | 1.00 | 64.00 | 205.00 |
| | | | Month 2 | 9 | 1 | 31.33 | 91.00 | 1.00 | 1.00 | 1.00 | 1.00 | 274.00 |
| | | | Month 3 | 10 | 0 | 164.20 | 315.17 | 1.00 | 1.00 | 2.00 | 204.00 | 1013.00 |
| | | VAR/E | Day 0 | 44 | 1 | 13.66 | 31.15 | 1.00 | 1.00 | 1.00 | 1.00 | 142.00 |
| | | | Month 1 | 43 | 2 | 9.65 | 29.29 | 1.00 | 1.00 | 1.00 | 1.00 | 153.00 |
| | | | Month 2 | 43 | 2 | 5.19 | 19.42 | 1.00 | 1.00 | 1.00 | 1.00 | 105.00 |
| | | | Month 3 | 45 | 0 | 12.62 | 31.58 | 1.00 | 1.00 | 1.00 | 1.00 | 142.00 |
| | | gE/E | Day 0 | 44 | 1 | 12.32 | 26.28 | 1.00 | 1.00 | 1.00 | 1.00 | 76.00 |
| | | | Month 1 | 42 | 3 | 14.31 | 27.82 | 1.00 | 1.00 | 1.00 | 1.00 | 78.00 |
| | | | Month 2 | 43 | 2 | 17.26 | 33.86 | 1.00 | 1.00 | 1.00 | 1.00 | 146.00 |
| | | | Month 3 | 43 | 2 | 14.16 | 32.29 | 1.00 | 1.00 | 1.00 | 1.00 | 150.00 |
| | | gEVAR/E | Day 0 | 43 | 2 | 7.16 | 19.48 | 1.00 | 1.00 | 1.00 | 1.00 | 71.00 |
| | | | Month 1 | 44 | 1 | 18.95 | 46.55 | 1.00 | 1.00 | 1.00 | 1.00 | 221.00 |
| | | | Month 2 | 45 | 0 | 22.71 | 43.70 | 1.00 | 1.00 | 1.00 | 1.00 | 200.00 |
| | | | Month 3 | 45 | 0 | 45.80 | 146.31 | 1.00 | 1.00 | 1.00 | 1.00 | 780.00 |
| | Varilrix | gE/Y | Day 0 | 9 | 1 | 260.56 | 651.12 | 1.00 | 1.00 | 68.00 | 69.00 | 1992.00 |
| | | | Month 1 | 9 | 1 | 235.78 | 609.46 | 1.00 | 1.00 | 1.00 | 120.00 | 1854.00 |
| | | | Month 2 | 9 | 1 | 291.22 | 741.43 | 1.00 | 1.00 | 68.00 | 71.00 | 2264.00 |
| | | | Month 3 | 9 | 1 | 240.78 | 644.21 | 1.00 | 1.00 | 1.00 | 70.00 | 1954.00 |
| | | gEVAR/Y | Day 0 | 10 | 0 | 21.00 | 32.21 | 1.00 | 1.00 | 1.00 | 67.00 | 69.00 |
| | | | Month 1 | 10 | 0 | 1.00 | 0.00 | 1.00 | 1.00 | 1.00 | 1.00 | 1.00 |
| | | | Month 2 | 9 | 1 | 24.00 | 49.34 | 1.00 | 1.00 | 1.00 | 1.00 | 142.00 |
| | | | Month 3 | 10 | 0 | 62.60 | 153.10 | 1.00 | 1.00 | 1.00 | 1.00 | 481.00 |
| | | VAR/E | Day 0 | 44 | 1 | 15.89 | 33.39 | 1.00 | 1.00 | 1.00 | 1.00 | 152.00 |
| | | | Month 1 | 43 | 2 | 31.95 | 58.90 | 1.00 | 1.00 | 1.00 | 68.00 | 261.00 |
| | | | Month 2 | 44 | 1 | 17.93 | 45.21 | 1.00 | 1.00 | 1.00 | 1.00 | 156.00 |
| | | | Month 3 | 45 | 0 | 17.84 | 39.12 | 1.00 | 1.00 | 1.00 | 1.00 | 152.00 |
| | | gE/E | Day 0 | 44 | 1 | 23.45 | 53.70 | 1.00 | 1.00 | 1.00 | 1.50 | 227.00 |
| | | | Month 1 | 42 | 3 | 25.02 | 65.40 | 1.00 | 1.00 | 1.00 | 1.00 | 363.00 |
| | | | Month 2 | 43 | 2 | 11.16 | 30.54 | 1.00 | 1.00 | 1.00 | 1.00 | 154.00 |
| | | | Month 3 | 43 | 2 | 20.49 | 44.84 | 1.00 | 1.00 | 1.00 | 1.00 | 218.00 |
| | | gEVAR/E | Day 0 | 43 | 2 | 25.58 | 48.47 | 1.00 | 1.00 | 1.00 | 1.00 | 147.00 |
| | | | Month 1 | 44 | 1 | 27.93 | 55.29 | 1.00 | 1.00 | 1.00 | 68.00 | 304.00 |
| | | | Month 2 | 45 | 0 | 12.18 | 38.15 | 1.00 | 1.00 | 1.00 | 1.00 | 225.00 |
| | | | Month 3 | 45 | 0 | 19.80 | 43.49 | 1.00 | 1.00 | 1.00 | 1.00 | 209.00 |
| CD8-IFNγ | Pool gE | gE/Y | Day 0 | 9 | 1 | 15.22 | 28.26 | 1.00 | 1.00 | 1.00 | 1.00 | 68.00 |
| | | | Month 1 | 9 | 1 | 38.44 | 35.55 | 1.00 | 1.00 | 67.00 | 68.00 | 72.00 |
| | | | Month 2 | 9 | 1 | 215.78 | 472.21 | 1.00 | 1.00 | 68.00 | 135.00 | 1464.00 |
| | | | Month 3 | 9 | 1 | 31.11 | 50.03 | 1.00 | 1.00 | 1.00 | 66.00 | 141.00 |
| | | gEVAR/Y | Day 0 | 10 | 0 | 89.40 | 110.49 | 1.00 | 1.00 | 68.00 | 143.00 | 336.00 |
| | | | Month 1 | 10 | 0 | 13.90 | 27.20 | 1.00 | 1.00 | 1.00 | 1.00 | 67.00 |

SUPPLEMENTARY TABLE C.1-continued

Intracellular Cytokine Staining (ICS): Descriptive
Statistics on CD8 T cells at each time point (Total vaccinated Cohort)

| Test | Antigen | Group | Timing | N | N miss. | Mean | SD | MM | Q1 | Median | Q3 | Max |
|---|---|---|---|---|---|---|---|---|---|---|---|---|
| | | | Month 2 | 9 | 1 | 31.11 | 68.87 | 1.00 | 1.00 | 1.00 | 1.00 | 205.00 |
| | | | Month 3 | 10 | 0 | 62.40 | 66.91 | 1.00 | 1.00 | 68.00 | 76.00 | 202.00 |
| | | VAR/E | Day 0 | 44 | 1 | 30.77 | 74.58 | 1.00 | 1.00 | 1.00 | 1.00 | 348.00 |
| | | | Month 1 | 43 | 2 | 21.30 | 50.45 | 1.00 | 1.00 | 1.00 | 1.00 | 216.00 |
| | | | Month 2 | 43 | 2 | 38.81 | 69.55 | 1.00 | 1.00 | 1.00 | 70.00 | 284.00 |
| | | | Month 3 | 45 | 0 | 15.13 | 38.77 | 1.00 | 1.00 | 1.00 | 1.00 | 146.00 |
| | | gE/E | Day 0 | 44 | 1 | 12.91 | 28.23 | 1.00 | 1.00 | 1.00 | 1.00 | 110.00 |
| | | | Month 1 | 42 | 3 | 30.40 | 71.67 | 1.00 | 1.00 | 1.00 | 1.00 | 351.00 |
| | | | Month 2 | 43 | 2 | 36.77 | 73.76 | 1.00 | 1.00 | 1.00 | 66.00 | 368.00 |
| | | | Month 3 | 43 | 2 | 31.33 | 85.07 | 1.00 | 1.00 | 1.00 | 1.00 | 461.00 |
| | | gEVAR/E | Day 0 | 43 | 2 | 12.63 | 38.39 | 1.00 | 1.00 | 1.00 | 1.00 | 220.00 |
| | | | Month 1 | 44 | 1 | 25.36 | 49.38 | 1.00 | 1.00 | 1.00 | 35.00 | 230.00 |
| | | | Month 2 | 45 | 0 | 11.67 | 25.17 | 1.00 | 1.00 | 1.00 | 1.00 | 75.00 |
| | | | Month 3 | 45 | 0 | 58.51 | 147.37 | 1.00 | 1.00 | 1.00 | 70.00 | 851.00 |
| | Varilrix | gE/Y | Day 0 | 9 | 1 | 475.11 | 1319.18 | 1.00 | 1.00 | 1.00 | 1.00 | 3984.00 |
| | | | Month 1 | 9 | 1 | 561.78 | 1644.43 | 1.00 | 1.00 | 1.00 | 1.00 | 4946.00 |
| | | | Month 2 | 9 | 1 | 935.22 | 2701.84 | 1.00 | 1.00 | 1.00 | 70.00 | 8139.00 |
| | | | Month 3 | 9 | 1 | 403.89 | 1183.38 | 1.00 | 1.00 | 1.00 | 1.00 | 3559.00 |
| | | gEVAR/Y | Day 0 | 10 | 0 | 49.30 | 87.98 | 1.00 | 1.00 | 1.00 | 68.00 | 283.00 |
| | | | Month 1 | 10 | 0 | 28.60 | 58.23 | 1.00 | 1.00 | 1.00 | 1.00 | 144.00 |
| | | | Month 2 | 9 | 1 | 61.44 | 86.91 | 1.00 | 1.00 | 1.00 | 68.00 | 208.00 |
| | | | Month 3 | 10 | 0 | 78.20 | 100.95 | 1.00 | 1.00 | 34.50 | 147.00 | 274.00 |
| | | VAR/E | Day 0 | 44 | 1 | 223.32 | 719.34 | 1.00 | 1.00 | 1.00 | 134.00 | 4534.00 |
| | | | Month 1 | 43 | 2 | 208.47 | 507.58 | 1.00 | 1.00 | 70.00 | 213.00 | 3021.00 |
| | | | Month 2 | 44 | 1 | 185.43 | 499.14 | 1.00 | 1.00 | 1.50 | 145.50 | 3085.00 |
| | | | Month 3 | 45 | 0 | 342.33 | 1408.21 | 1.00 | 1.00 | 31.00 | 147.00 | 9423.00 |
| | | gE/E | Day 0 | 44 | 1 | 227.52 | 482.15 | 1.00 | 1.00 | 1.00 | 204.50 | 2216.00 |
| | | | Month 1 | 42 | 3 | 273.88 | 613.11 | 1.00 | 1.00 | 66.00 | 225.00 | 2909.00 |
| | | | Month 2 | 43 | 2 | 228.79 | 542.44 | 1.00 | 1.00 | 70.00 | 206.00 | 2591.00 |
| | | | Month 3 | 43 | 2 | 235.33 | 490.73 | 1.00 | 1.00 | 69.00 | 189.00 | 2491.00 |
| | | gEVAR/E | Day 0 | 43 | 2 | 156.53 | 390.28 | 1.00 | 1.00 | 1.00 | 76.00 | 2000.00 |
| | | | Month 1 | 44 | 1 | 177.48 | 309.13 | 1.00 | 1.00 | 67.00 | 217.00 | 1398.00 |
| | | | Month 2 | 45 | 0 | 220.84 | 518.38 | 1.00 | 1.00 | 1.00 | 147.00 | 2491.00 |
| | | | Month 3 | 45 | 0 | 291.38 | 515.67 | 1.00 | 1.00 | 92.00 | 290.00 | 2418.00 |
| CD8-IL2 | Pool gE | gE/Y | Day 0 | 9 | 1 | 22.67 | 32.55 | 1.00 | 1.00 | 1.00 | 62.00 | 68.00 |
| | | | Month 1 | 9 | 1 | 61.78 | 111.15 | 1.00 | 1.00 | 1.00 | 68.00 | 345.00 |
| | | | Month 2 | 9 | 1 | 557.67 | 1595.67 | 1.00 | 1.00 | 1.00 | 68.00 | 4811.00 |
| | | | Month 3 | 9 | 1 | 31.33 | 50.21 | 1.00 | 1.00 | 1.00 | 66.00 | 141.00 |
| | | gEVAR/Y | Day 0 | 10 | 0 | 136.90 | 232.25 | 1.00 | 1.00 | 1.00 | 206.00 | 674.00 |
| | | | Month 1 | 10 | 0 | 34.30 | 65.70 | 1.00 | 1.00 | 1.00 | 64.00 | 205.00 |
| | | | Month 2 | 9 | 1 | 39.00 | 114.00 | 1.00 | 1.00 | 1.00 | 1.00 | 343.00 |
| | | | Month 3 | 10 | 0 | 170.70 | 315.26 | 1.00 | 1.00 | 35.50 | 272.00 | 1013.00 |
| | | VAR/E | Day 0 | 44 | 1 | 20.30 | 46.60 | 1.00 | 1.00 | 1.00 | 1.00 | 223.00 |
| | | | Month 1 | 43 | 2 | 13.14 | 36.17 | 1.00 | 1.00 | 1.00 | 1.00 | 153.00 |
| | | | Month 2 | 43 | 2 | 16.26 | 43.32 | 1.00 | 1.00 | 1.00 | 1.00 | 212.00 |
| | | | Month 3 | 45 | 0 | 17.49 | 38.46 | 1.00 | 1.00 | 1.00 | 1.00 | 152.00 |
| | | gE/E | Day 0 | 44 | 1 | 16.55 | 43.92 | 1.00 | 1.00 | 1.00 | 1.00 | 212.00 |
| | | | Month 1 | 42 | 3 | 19.29 | 36.16 | 1.00 | 1.00 | 1.00 | 1.00 | 140.00 |
| | | | Month 2 | 43 | 2 | 28.53 | 54.26 | 1.00 | 1.00 | 1.00 | 66.00 | 221.00 |
| | | | Month 3 | 43 | 2 | 16.28 | 44.66 | 1.00 | 1.00 | 1.00 | 1.00 | 229.00 |
| | | gEVAR/E | Day 0 | 43 | 2 | 7.21 | 19.47 | 1.00 | 1.00 | 1.00 | 1.00 | 71.00 |
| | | | Month 1 | 44 | 1 | 25.84 | 51.64 | 1.00 | 1.00 | 1.00 | 6.50 | 221.00 |
| | | | Month 2 | 45 | 0 | 24.18 | 44.41 | 1.00 | 1.00 | 1.00 | 3.00 | 149.00 |
| | | | Month 3 | 45 | 0 | 45.76 | 148.50 | 1.00 | 1.00 | 1.00 | 1.00 | 851.00 |
| | Varilrix | gE/Y | Day 0 | 9 | 1 | 102.78 | 207.48 | 1.00 | 1.00 | 1.00 | 69.00 | 640.00 |
| | | | Month 1 | 9 | 1 | 151.78 | 359.31 | 1.00 | 1.00 | 1.00 | 120.00 | 1098.00 |
| | | | Month 2 | 9 | 1 | 227.78 | 503.56 | 1.00 | 1.00 | 68.00 | 136.00 | 1556.00 |
| | | | Month 3 | 9 | 1 | 93.56 | 181.12 | 1.00 | 1.00 | 1.00 | 71.00 | 559.00 |
| | | gEVAR/Y | Day 0 | 10 | 0 | 14.40 | 28.25 | 1.00 | 1.00 | 1.00 | 1.00 | 69.00 |
| | | | Month 1 | 10 | 0 | 7.60 | 20.87 | 1.00 | 1.00 | 1.00 | 1.00 | 67.00 |
| | | | Month 2 | 9 | 1 | 39.11 | 60.89 | 1.00 | 1.00 | 1.00 | 67.00 | 142.00 |
| | | | Month 3 | 10 | 0 | 62.60 | 153.10 | 1.00 | 1.00 | 1.00 | 1.00 | 481.00 |
| | | VAR/E | Day 0 | 44 | 1 | 99.27 | 241.07 | 1.00 | 1.00 | 1.00 | 73.00 | 1223.00 |
| | | | Month 1 | 43 | 2 | 78.49 | 122.70 | 1.00 | 1.00 | 66.00 | 109.00 | 575.00 |
| | | | Month 2 | 44 | 1 | 97.00 | 226.12 | 1.00 | 1.00 | 1.00 | 75.50 | 1028.00 |
| | | | Month 3 | 45 | 0 | 144.38 | 452.96 | 1.00 | 1.00 | 1.00 | 137.00 | 2994.00 |
| | | gE/E | Day 0 | 44 | 1 | 140.34 | 240.41 | 1.00 | 1.00 | 33.50 | 153.00 | 1271.00 |
| | | | Month 1 | 42 | 3 | 124.21 | 246.93 | 1.00 | 1.00 | 1.00 | 145.00 | 1017.00 |
| | | | Month 2 | 43 | 2 | 99.79 | 166.75 | 1.00 | 1.00 | 1.00 | 144.00 | 863.00 |
| | | | Month 3 | 43 | 2 | 148.19 | 264.30 | 1.00 | 1.00 | 14.00 | 145.00 | 1173.00 |
| | | gEVAR/E | Day 0 | 43 | 2 | 68.81 | 116.27 | 1.00 | 1.00 | 1.00 | 77.00 | 573.00 |
| | | | Month 1 | 44 | 1 | 87.89 | 122.66 | 1.00 | 1.00 | 68.00 | 141.00 | 521.00 |
| | | | Month 2 | 45 | 0 | 113.91 | 231.46 | 1.00 | 1.00 | 1.00 | 138.00 | 1127.00 |
| | | | Month 3 | 45 | 0 | 163.44 | 232.53 | 1.00 | 1.00 | 71.00 | 215.00 | 967.00 |

SUPPLEMENTARY TABLE C.1-continued

Intracellular Cytokine Staining (ICS): Descriptive Statistics on CD8 T cells at each time point (Total vaccinated Cohort)

| Test | Antigen | Group | Timing | N | N miss. | Mean | SD | MM | Q1 | Median | Q3 | Max |
|---|---|---|---|---|---|---|---|---|---|---|---|---|
| CD8-TNFα | Pool gE | gE/Y | Day 0 | 9 | 1 | 23.33 | 33.50 | 1.00 | 1.00 | 1.00 | 68.00 | 68.00 |
| | | | Month 1 | 9 | 1 | 1.00 | 0.00 | 1.00 | 1.00 | 1.00 | 1.00 | 1.00 |
| | | | Month 2 | 9 | 1 | 15.89 | 44.67 | 1.00 | 1.00 | 1.00 | 1.00 | 135.00 |
| | | | Month 3 | 9 | 1 | 23.89 | 49.04 | 1.00 | 1.00 | 1.00 | 1.00 | 141.00 |
| | | gEVAR/Y | Day 0 | 10 | 0 | 35.00 | 65.20 | 1.00 | 1.00 | 1.00 | 68.00 | 201.00 |
| | | | Month 1 | 10 | 0 | 1.00 | 0.00 | 1.00 | 1.00 | 1.00 | 1.00 | 1.00 |
| | | | Month 2 | 9 | 1 | 8.56 | 22.67 | 1.00 | 1.00 | 1.00 | 1.00 | 69.00 |
| | | | Month 3 | 10 | 0 | 8.00 | 21.10 | 1.00 | 1.00 | 1.00 | 1.00 | 68.00 |
| | | VAR/E | Day 0 | 44 | 1 | 32.20 | 75.14 | 1.00 | 1.00 | 1.00 | 1.50 | 348.00 |
| | | | Month 1 | 43 | 2 | 33.05 | 63.48 | 1.00 | 1.00 | 1.00 | 72.00 | 288.00 |
| | | | Month 2 | 43 | 2 | 31.40 | 67.10 | 1.00 | 1.00 | 1.00 | 12.00 | 284.00 |
| | | | Month 3 | 45 | 0 | 19.80 | 48.19 | 1.00 | 1.00 | 1.00 | 1.00 | 207.00 |
| | | gE/E | Day 0 | 44 | 1 | 18.80 | 44.11 | 1.00 | 1.00 | 1.00 | 1.00 | 221.00 |
| | | | Month 1 | 42 | 3 | 32.60 | 77.37 | 1.00 | 1.00 | 1.00 | 37.00 | 422.00 |
| | | | Month 2 | 43 | 2 | 30.02 | 47.35 | 1.00 | 1.00 | 1.00 | 66.00 | 221.00 |
| | | | Month 3 | 43 | 2 | 24.53 | 67.55 | 1.00 | 1.00 | 1.00 | 1.00 | 306.00 |
| | | gEVAR/E | Day 0 | 43 | 2 | 15.79 | 40.14 | 1.00 | 1.00 | 1.00 | 1.00 | 220.00 |
| | | | Month 1 | 44 | 1 | 28.91 | 57.44 | 1.00 | 1.00 | 1.00 | 33.50 | 230.00 |
| | | | Month 2 | 45 | 0 | 21.13 | 41.06 | 1.00 | 1.00 | 1.00 | 1.00 | 149.00 |
| | | | Month 3 | 45 | 0 | 52.49 | 124.92 | 1.00 | 1.00 | 1.00 | 69.00 | 709.00 |
| | Varilrix | gE/Y | Day 0 | 9 | 1 | 459.33 | 1297.02 | 1.00 | 1.00 | 1.00 | 2.00 | 3913.00 |
| | | | Month 1 | 9 | 1 | 535.67 | 1526.03 | 1.00 | 1.00 | 1.00 | 70.00 | 4603.00 |
| | | | Month 2 | 9 | 1 | 928.11 | 2730.86 | 1.00 | 1.00 | 1.00 | 67.00 | 8210.00 |
| | | | Month 3 | 9 | 1 | 373.22 | 1090.66 | 1.00 | 1.00 | 1.00 | 1.00 | 3281.00 |
| | | gEVAR/Y | Day 0 | 10 | 0 | 35.60 | 68.51 | 1.00 | 1.00 | 1.00 | 67.00 | 214.00 |
| | | | Month 1 | 10 | 0 | 21.50 | 45.55 | 1.00 | 1.00 | 1.00 | 1.00 | 134.00 |
| | | | Month 2 | 9 | 1 | 69.33 | 102.76 | 1.00 | 1.00 | 1.00 | 70.00 | 274.00 |
| | | | Month 3 | 10 | 0 | 44.20 | 77.20 | 1.00 | 1.00 | 1.00 | 73.00 | 215.00 |
| | | VAR/E | Day 0 | 44 | 1 | 200.27 | 729.98 | 1.00 | 1.00 | 1.00 | 75.00 | 4678.00 |
| | | | Month 1 | 43 | 2 | 168.60 | 469.56 | 1.00 | 1.00 | 34.00 | 141.00 | 2805.00 |
| | | | Month 2 | 44 | 1 | 159.45 | 432.79 | 1.00 | 1.00 | 1.00 | 129.50 | 2717.00 |
| | | | Month 3 | 45 | 0 | 309.73 | 1310.43 | 1.00 | 1.00 | 1.00 | 133.00 | 8765.00 |
| | | gE/E | Day 0 | 44 | 1 | 201.23 | 441.88 | 1.00 | 1.00 | 1.00 | 150.50 | 2057.00 |
| | | | Month 1 | 42 | 3 | 230.05 | 531.94 | 1.00 | 1.00 | 47.50 | 225.00 | 2545.00 |
| | | | Month 2 | 43 | 2 | 221.44 | 535.05 | 1.00 | 1.00 | 66.00 | 225.00 | 2591.00 |
| | | | Month 3 | 43 | 2 | 189.44 | 402.52 | 1.00 | 1.00 | 61.00 | 189.00 | 2125.00 |
| | | gEVAR/E | Day 0 | 43 | 2 | 133.88 | 332.42 | 1.00 | 1.00 | 1.00 | 72.00 | 1712.00 |
| | | | Month 1 | 44 | 1 | 172.50 | 306.32 | 1.00 | 1.00 | 67.00 | 212.50 | 1398.00 |
| | | | Month 2 | 45 | 0 | 190.29 | 470.52 | 1.00 | 1.00 | 1.00 | 147.00 | 2340.00 |
| | | | Month 3 | 45 | 0 | 255.16 | 490.59 | 1.00 | 1.00 | 71.00 | 215.00 | 2279.00 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years
N = number of subjects with available results
N miss. = number of subjects with missing results
SD = Standard Deviation
Min, Max = Minimum, Maximum
Q1, Q3 = First, Third quartile

TABLE C.2

Intracellular Cytokine Staining (ICS): Inferential statistics: P-values from Kruskal-Wallis Tests for CD4 T cells at each time point (Total Vaccinated Cohort)

| T cells | Groups compared | Antigen | Test | P_value at day 0 | P_value at Month 1 | P_value at Month 2 | P_value at Month 3 |
|---|---|---|---|---|---|---|---|
| CD4 | VAR\E and gEVAR\E | Pool gE | ALL DOUBLES | 0.5025 | 0.0000 | 0.0015 | 0.0000 |
| | | | CD40L | 0.4448 | 0.0000 | 0.0004 | 0.0000 |
| | | | IFNγ | 0.5900 | 0.0001 | 0.0956 | 0.0000 |
| | | | IL2 | 0.6415 | 0.0000 | 0.0001 | 0.0000 |
| | | | TNFα | 0.2634 | 0.0000 | 0.0019 | 0.0000 |
| | | Varilrix | ALL DOUBLES | 0.7118 | 0.1489 | 0.3148 | 0.0000 |
| | | | CD40L | 0.6488 | 0.1664 | 0.2609 | 0.0000 |
| | | | IFNγ | 0.3602 | 0.2905 | 0.2277 | 0.0000 |
| | | | IL2 | 0.4880 | 0.1442 | 0.2406 | 0.0000 |
| | | | TNFα | 0.8631 | 0.2624 | 0.2455 | 0.0000 |

TABLE C.2-continued

Intracellular Cytokine Staining (ICS): Inferential statistics: P-values from Kruskal-Wallis Tests for CD4 T cells at each time point (Total Vaccinated Cohort)

| T cells | Groups compared | Antigen | Test | P_value at day 0 | P_value at Month 1 | P_value at Month 2 | P_value at Month 3 |
|---|---|---|---|---|---|---|---|
| | VAR\E and gE\E | Pool gE | ALL DOUBLES | 0.9764 | 0.0004 | 0.0100 | 0.0000 |
| | | | CD40L | 0.9765 | 0.0003 | 0.0026 | 0.0000 |
| | | | IFNγ | 0.9665 | 0.0228 | 0.2961 | 0.0000 |
| | | | IL2 | 0.7183 | 0.0001 | 0.0035 | 0.0000 |
| | | | TNFα | 0.9026 | 0.0069 | 0.0053 | 0.0000 |
| | | Varilrix | ALL DOUBLES | 0.9069 | 0.9965 | 0.8552 | 0.0002 |
| | | | CD40L | 0.8904 | 0.9790 | 0.9155 | 0.0002 |
| | | | IFNγ | 0.8806 | 0.5797 | 0.6868 | 0.0010 |
| | | | IL2 | 0.9601 | 0.9860 | 0.9054 | 0.0003 |
| | | | TNFα | 0.6073 | 0.9719 | 0.8154 | 0.0016 |
| | gE\E and gEVAR\E | Pool gE | ALL DOUBLES | 0.4951 | 0.1777 | 0.5702 | 0.4832 |
| | | | CD40L | 0.3731 | 0.2215 | 0.5312 | 0.5368 |
| | | | IFNγ | 0.7732 | 0.2331 | 0.5958 | 0.8576 |
| | | | IL2 | 0.9406 | 0.3059 | 0.4181 | 0.5069 |
| | | | TNFα | 0.3949 | 0.2039 | 0.5613 | 0.3287 |
| | | Varilrix | ALL DOUBLES | 0.8469 | 0.1876 | 0.2409 | 0.2687 |
| | | | CD40L | 0.9803 | 0.1980 | 0.2060 | 0.2277 |
| | | | IFNγ | 0.7520 | 0.2103 | 0.1205 | 0.2182 |
| | | | IL2 | 0.7211 | 0.2135 | 0.2375 | 0.3045 |
| | | | TNFα | 0.8118 | 0.2134 | 0.1817 | 0.2778 |

VAR/E = Varilrix/50-70 years
gE/E = gE-AS1/50-70 years
gEVAR/E = gE-AS1 + Varilrix/50-70 years

SUPPLEMENTARY TABLE C.2

Intracellular Cytokine Staining (ICS): Inferential statistics: P-values from Kruskal-Wallis Tests for CD8 T cells at each time point (Total Vaccinated Cohort)

| T cells | Groups compared | Antigen | Test | P_value at day 0 | P_value at Month 1 | P_value at Month 2 | P_value at Month 3 |
|---|---|---|---|---|---|---|---|
| CD8 | VAR\E and gEVAR\E | Pool gE | ALL DOUBLES | 0.1477 | 0.4418 | 0.8141 | 0.2762 |
| | | | CD40L | 0.2897 | 0.2513 | 0.0126 | 0.3511 |
| | | | IFNγ | 0.1695 | 0.4069 | 0.0478 | 0.0478 |
| | | | IL2 | 0.2705 | 0.1316 | 0.2008 | 0.5872 |
| | | | TNFα | 0.2968 | 0.7017 | 0.6470 | 0.0947 |
| | | Varilrix | ALL DOUBLES | 0.9267 | 0.7605 | 0.9651 | 0.1197 |
| | | | CD40L | 0.6260 | 0.9111 | 0.6512 | 0.8826 |
| | | | IFNγ | 0.9846 | 0.9611 | 0.9225 | 0.1009 |
| | | | IL2 | 0.7027 | 0.6963 | 0.4626 | 0.1181 |
| | | | TNFα | 0.9047 | 0.4655 | 0.9929 | 0.1639 |
| | VAR\E and gE\E | Pool gE | ALL DOUBLES | 0.4117 | 0.9608 | 0.4570 | 0.9320 |
| | | | CD40L | 0.7891 | 0.2636 | 0.0315 | 0.7302 |
| | | | IFNγ | 0.4922 | 0.5672 | 0.7960 | 0.3690 |
| | | | IL2 | 0.6092 | 0.2137 | 0.1416 | 0.6416 |
| | | | TNFα | 0.5891 | 0.8828 | 0.4633 | 0.9530 |
| | | Varilrix | ALL DOUBLES | 0.2336 | 0.9168 | 0.4792 | 0.6436 |
| | | | CD40L | 0.5969 | 0.3443 | 0.6968 | 0.8133 |
| | | | IFNγ | 0.3606 | 0.9342 | 0.3019 | 0.5406 |
| | | | IL2 | 0.1743 | 0.6509 | 0.2577 | 0.4652 |
| | | | TNFα | 0.3405 | 0.7627 | 0.3869 | 0.5577 |
| | gE/E and gEVAR\E | Pool gE | ALL DOUBLES | 0.4942 | 0.3322 | 0.2975 | 0.3120 |
| | | | CD40L | 0.1831 | 0.9898 | 0.6047 | 0.5555 |
| | | | IFNγ | 0.4515 | 0.8129 | 0.0948 | 0.2325 |
| | | | IL2 | 0.6171 | 0.7224 | 0.8439 | 0.3147 |
| | | | TNFα | 0.6064 | 0.7472 | 0.2571 | 0.1078 |
| | | Varilrix | ALL DOUBLES | 0.2524 | 0.8479 | 0.4410 | 0.2783 |
| | | | CD40L | 0.9594 | 0.3385 | 0.9095 | 0.9433 |
| | | | IFNγ | 0.3465 | 0.9277 | 0.3691 | 0.2849 |
| | | | IL2 | 0.2333 | 0.5263 | 0.7101 | 0.4173 |
| | | | TNFα | 0.4678 | 0.7167 | 0.3198 | 0.4684 |

VAR/E = Varilrix/50-70 years
gE/E = gE-AS1/50-70 years
gEVAR/E = gE-AS1 + Varilrix/50-70 years

TABLE C.3

Intracellular Cytokine Staining (ICS): Descriptive Statistics on CD4 T cells at POST−PRE (Total vaccinated Cohort)

| Test | Antigen | Group | Timing | N | N miss. | Mean | SD | Min | Q1 | Median | Q3 | Max |
|---|---|---|---|---|---|---|---|---|---|---|---|---|
| CD4−ALL DOUBLES | Pool gE | gE/Y | Month 1 | 9 | 1 | 1170.33 | 1640.79 | −80.00 | 230.00 | 434.00 | 1332.00 | 5096.00 |
| | | | Month 2 | 9 | 1 | 1574.11 | 1884.90 | 256.00 | 496.00 | 723.00 | 1285.00 | 5428.00 |
| | | | Month 3 | 9 | 1 | 2526.44 | 1927.96 | 442.00 | 1329.00 | 2233.00 | 2647.00 | 6852.00 |
| | | gEVAR/Y | Month 1 | 10 | 0 | 926.50 | 846.70 | −348.00 | 393.00 | 865.50 | 1363.00 | 2752.00 |
| | | | Month 2 | 9 | 1 | 1308.56 | 846.35 | −233.00 | 845.00 | 1681.00 | 1995.00 | 2178.00 |
| | | | Month 3 | 10 | 0 | 3045.30 | 1361.87 | 1288.00 | 1969.00 | 2830.50 | 4533.00 | 5057.00 |
| | | VAR/E | Month 1 | 42 | 3 | 147.90 | 460.77 | −436.00 | −49.00 | 25.50 | 155.00 | 1898.00 |
| | | | Month 2 | 43 | 2 | −84.23 | 947.38 | −5979.00 | −60.00 | 35.00 | 179.00 | 658.00 |
| | | | Month 3 | 44 | 1 | 173.16 | 1441.28 | −5191.00 | −128.00 | 0.00 | 146.00 | 6263.00 |
| | | gE/E | Month 1 | 42 | 3 | 691.74 | 1008.97 | −163.00 | 135.00 | 310.00 | 826.00 | 4210.00 |
| | | | Month 2 | 43 | 2 | 352.00 | 515.95 | −337.00 | 39.00 | 206.00 | 485.00 | 1974.00 |
| | | | Month 3 | 42 | 3 | 3118.48 | 2537.47 | −112.00 | 1324.00 | 2344.50 | 4620.00 | 11479.00 |
| | | gEVAR/E | Month 1 | 44 | 1 | 616.02 | 505.69 | −184.00 | 165.00 | 597.50 | 902.00 | 2377.00 |
| | | | Month 2 | 45 | 0 | 303.13 | 389.20 | −549.00 | 52.00 | 266.00 | 515.00 | 1234.00 |
| | | | Month 3 | 45 | 0 | 2712.02 | 2508.85 | −542.00 | 925.00 | 1601.00 | 4223.00 | 10467.00 |
| | Varilrix | gE/Y | Month 1 | 9 | 1 | 256.89 | 842.23 | −811.00 | −214.00 | −87.00 | 712.00 | 1612.00 |
| | | | Month 2 | 9 | 1 | 610.22 | 651.41 | −72.00 | 129.00 | 361.00 | 831.00 | 1904.00 |
| | | | Month 3 | 9 | 1 | 770.56 | 891.01 | −787.00 | 548.00 | 718.00 | 1165.00 | 2343.00 |
| | | gEVAR/Y | Month 1 | 10 | 0 | −98.40 | 1180.58 | −1610.00 | −647.00 | −31.50 | 75.00 | 2732.00 |
| | | | Month 2 | 9 | 1 | 1547.67 | 993.79 | 225.00 | 797.00 | 1286.00 | 2179.00 | 3188.00 |
| | | | Month 3 | 10 | 0 | 2181.30 | 1781.51 | 151.00 | 698.00 | 1867.00 | 2861.00 | 6210.00 |
| | | VAR/E | Month 1 | 42 | 3 | 366.95 | 798.30 | −663.00 | 0.00 | 173.00 | 536.00 | 4145.00 |
| | | | Month 2 | 43 | 2 | 169.07 | 569.41 | −2100.00 | −39.00 | 197.00 | 325.00 | 1608.00 |
| | | | Month 3 | 44 | 1 | 362.93 | 662.91 | −2100.00 | 54.00 | 267.50 | 633.50 | 1906.00 |
| | | gE/E | Month 1 | 42 | 3 | 524.74 | 946.86 | −660.00 | 0.00 | 229.00 | 734.00 | 4178.00 |
| | | | Month 2 | 43 | 2 | 95.30 | 633.65 | −1405.00 | −205.00 | 18.00 | 254.00 | 1961.00 |
| | | | Month 3 | 42 | 3 | 1533.69 | 1557.01 | −600.00 | 528.00 | 1090.00 | 2181.00 | 7044.00 |
| | | gEVAR/E | Month 1 | 44 | 1 | 664.14 | 765.08 | −555.00 | 184.50 | 575.00 | 1109.00 | 3364.00 |
| | | | Month 2 | 45 | 0 | 451.04 | 652.53 | −397.00 | 34.00 | 244.00 | 639.00 | 2601.00 |
| | | | Month 3 | 45 | 0 | 1973.73 | 1577.30 | 70.00 | 918.00 | 1480.00 | 2659.00 | 6575.00 |
| CD4-CD40L | Pool gE | gE/Y | Month 1 | 9 | 1 | 1142.67 | 1567.96 | −77.00 | 290.00 | 434.00 | 1272.00 | 4889.00 |
| | | | Month 2 | 9 | 1 | 1519.78 | 1786.74 | 336.00 | 465.00 | 680.00 | 1369.00 | 5120.00 |
| | | | Month 3 | 9 | 1 | 2363.22 | 1772.92 | 375.00 | 1303.00 | 1870.00 | 2323.00 | 6282.00 |
| | | gEVAR/Y | Month 1 | 10 | 0 | 868.50 | 852.69 | −348.00 | 381.00 | 813.00 | 1265.00 | 2782.00 |
| | | | Month 2 | 9 | 1 | 1278.44 | 841.17 | −233.00 | 691.00 | 1620.00 | 2027.00 | 2048.00 |
| | | | Month 3 | 10 | 0 | 2915.50 | 1350.46 | 1150.00 | 1816.00 | 2785.50 | 4273.00 | 5088.00 |
| | | VAR/E | Month 1 | 42 | 3 | 141.24 | 434.95 | −487.00 | −22.00 | 44.00 | 161.00 | 1837.00 |
| | | | Month 2 | 43 | 2 | −80.09 | 893.99 | −5627.00 | −74.00 | 26.00 | 195.00 | 601.00 |
| | | | Month 3 | 44 | 1 | 169.66 | 1401.60 | −4969.00 | −100.00 | 6.50 | 136.00 | 6071.00 |
| | | gE/E | Month 1 | 42 | 3 | 691.05 | 975.64 | −183.00 | 154.00 | 323.00 | 814.00 | 4153.00 |
| | | | Month 2 | 43 | 2 | 367.37 | 493.31 | −306.00 | 64.00 | 222.00 | 546.00 | 1976.00 |
| | | | Month 3 | 42 | 3 | 3036.88 | 2447.00 | −189.00 | 1342.00 | 2320.00 | 4568.00 | 10509.00 |
| | | gEVAR/E | Month 1 | 44 | 1 | 603.75 | 496.38 | −112.00 | 183.00 | 583.50 | 878.50 | 2268.00 |
| | | | Month 2 | 45 | 0 | 308.96 | 364.06 | −493.00 | 115.00 | 266.00 | 515.00 | 1185.00 |
| | | | Month 3 | 45 | 0 | 2692.24 | 2497.48 | −397.00 | 918.00 | 1652.00 | 4189.00 | 10417.00 |
| | Varilrix | gE/Y | Month 1 | 9 | 1 | 236.33 | 828.70 | −790.00 | −212.00 | −62.00 | 634.00 | 1594.00 |
| | | | Month 2 | 9 | 1 | 581.89 | 584.04 | −74.00 | 217.00 | 361.00 | 781.00 | 1587.00 |
| | | | Month 3 | 9 | 1 | 722.89 | 892.40 | −737.00 | 210.00 | 747.00 | 1091.00 | 2284.00 |
| | | gEVAR/Y | Month 1 | 10 | 0 | −122.90 | 1156.16 | −1604.00 | −613.00 | −114.50 | 75.00 | 2676.00 |
| | | | Month 2 | 9 | 1 | 1519.67 | 1018.54 | 259.00 | 684.00 | 1228.00 | 2137.00 | 3210.00 |
| | | | Month 3 | 10 | 0 | 2054.60 | 1759.67 | 36.00 | 554.00 | 1840.50 | 2421.00 | 6057.00 |
| | | VAR/E | Month 1 | 42 | 3 | 355.62 | 780.99 | −623.00 | 25.00 | 150.50 | 529.00 | 4128.00 |
| | | | Month 2 | 43 | 2 | 160.72 | 567.36 | −2024.00 | −32.00 | 158.00 | 349.00 | 1631.00 |
| | | | Month 3 | 44 | 1 | 351.45 | 663.33 | −2024.00 | 4.00 | 199.00 | 616.50 | 1972.00 |
| | | gE/E | Month 1 | 42 | 3 | 509.52 | 852.27 | −679.00 | −5.00 | 213.50 | 747.00 | 3242.00 |
| | | | Month 2 | 43 | 2 | 109.05 | 630.36 | −1378.00 | −181.00 | 27.00 | 257.00 | 2004.00 |
| | | | Month 3 | 42 | 3 | 1501.02 | 1546.41 | −881.00 | 562.00 | 1036.50 | 2095.00 | 7128.00 |
| | | gEVAR/E | Month 1 | 44 | 1 | 661.55 | 758.32 | −487.00 | 155.50 | 593.50 | 1066.50 | 3519.00 |
| | | | Month 2 | 45 | 0 | 457.07 | 652.72 | −411.00 | 33.00 | 290.00 | 580.00 | 2646.00 |
| | | | Month 3 | 45 | 0 | 1931.53 | 1542.71 | 71.00 | 916.00 | 1427.00 | 2686.00 | 6529.00 |
| CD4-IFNγ | Pool gE | gE/Y | Month 1 | 9 | 1 | 855.89 | 1270.64 | −83.00 | 56.00 | 498.00 | 823.00 | 3836.00 |
| | | | Month 2 | 9 | 1 | 1152.67 | 1414.76 | 192.00 | 402.00 | 511.00 | 1087.00 | 4569.00 |
| | | | Month 3 | 9 | 1 | 1841.44 | 1805.38 | 254.00 | 894.00 | 1227.00 | 1892.00 | 6156.00 |
| | | gEVAR/Y | Month 1 | 10 | 0 | 646.20 | 866.49 | −241.00 | 194.00 | 402.00 | 739.00 | 2897.00 |
| | | | Month 2 | 9 | 1 | 898.89 | 743.23 | −203.00 | 367.00 | 1064.00 | 1602.00 | 1789.00 |
| | | | Month 3 | 10 | 0 | 2108.30 | 1216.76 | 920.00 | 1089.00 | 1854.50 | 2667.00 | 5000.00 |
| | | VAR/E | Month 1 | 42 | 3 | 104.52 | 323.14 | −231.00 | −17.00 | 29.50 | 84.00 | 1809.00 |
| | | | Month 2 | 43 | 2 | −25.56 | 505.62 | −3122.00 | −24.00 | 33.00 | 117.00 | 561.00 |
| | | | Month 3 | 44 | 1 | 99.75 | 731.24 | −2787.00 | −32.00 | 11.00 | 88.50 | 3037.00 |
| | | gE/E | Month 1 | 42 | 3 | 395.14 | 676.51 | −72.00 | 45.00 | 174.50 | 333.00 | 3116.00 |
| | | | Month 2 | 43 | 2 | 161.98 | 330.61 | −305.00 | 5.00 | 54.00 | 219.00 | 1539.00 |
| | | | Month 3 | 42 | 3 | 1583.48 | 1568.34 | −47.00 | 491.00 | 1224.00 | 2077.00 | 6308.00 |
| | | gEVAR/E | Month 1 | 44 | 1 | 350.95 | 333.21 | −34.00 | 91.00 | 270.50 | 554.00 | 1349.00 |
| | | | Month 2 | 45 | 0 | 172.09 | 273.80 | −186.00 | 8.00 | 82.00 | 274.00 | 1062.00 |
| | | | Month 3 | 45 | 0 | 1392.40 | 1301.10 | −29.00 | 484.00 | 875.00 | 1961.00 | 5786.00 |

TABLE C.3-continued

Intracellular Cytokine Staining (ICS): Descriptive Statistics on
CD4 T cells at POST−PRE (Total vaccinated Cohort)

| Test | Antigen | Group | Timing | N | N miss. | Mean | SD | Min | Q1 | Median | Q3 | Max |
|---|---|---|---|---|---|---|---|---|---|---|---|---|
| | Varilrix | gE/Y | Month 1 | 9 | 1 | 196.44 | 699.90 | −663.00 | −156.00 | −144.00 | 431.00 | 1472.00 |
| | | | Month 2 | 9 | 1 | 428.22 | 503.10 | −132.00 | 84.00 | 332.00 | 743.00 | 1342.00 |
| | | | Month 3 | 9 | 1 | 507.00 | 696.91 | −781.00 | 196.00 | 471.00 | 831.00 | 1563.00 |
| | | gEVAR/Y | Month 1 | 10 | 0 | −25.40 | 1073.83 | −1588.00 | −456.00 | −20.00 | 106.00 | 2599.00 |
| | | | Month 2 | 9 | 1 | 1246.56 | 985.49 | 88.00 | 467.00 | 945.00 | 1661.00 | 3056.00 |
| | | | Month 3 | 10 | 0 | 1768.90 | 1593.80 | 168.00 | 634.00 | 1485.50 | 2136.00 | 5549.00 |
| | | VAR/E | Month 1 | 42 | 3 | 309.07 | 689.54 | −701.00 | 16.00 | 187.50 | 396.00 | 3829.00 |
| | | | Month 2 | 43 | 2 | 116.07 | 496.80 | −1934.00 | −74.00 | 134.00 | 283.00 | 1515.00 |
| | | | Month 3 | 44 | 1 | 254.25 | 539.74 | −1750.00 | 23.00 | 161.50 | 445.00 | 1861.00 |
| | | gE/E | Month 1 | 42 | 3 | 405.48 | 723.30 | −631.00 | −25.00 | 204.00 | 515.00 | 2775.00 |
| | | | Month 2 | 43 | 2 | 33.23 | 464.33 | −1258.00 | −102.00 | 42.00 | 204.00 | 1236.00 |
| | | | Month 3 | 42 | 3 | 1042.86 | 1155.33 | −529.00 | 402.00 | 805.00 | 1590.00 | 6357.00 |
| | | gEVAR/E | Month 1 | 44 | 1 | 548.59 | 714.90 | −621.00 | 111.00 | 374.50 | 757.50 | 3276.00 |
| | | | Month 2 | 45 | 0 | 399.91 | 618.77 | −454.00 | 47.00 | 231.00 | 474.00 | 2730.00 |
| | | | Month 3 | 45 | 0 | 1382.96 | 1099.42 | −1.00 | 652.00 | 1088.00 | 1679.00 | 4831.00 |
| CD4-IL2 | Pool gE | gE/Y | Month 1 | 9 | 1 | 1093.00 | 1486.37 | −40.00 | 228.00 | 465.00 | 1118.00 | 4669.00 |
| | | | Month 2 | 9 | 1 | 1495.67 | 1762.08 | 316.00 | 524.00 | 623.00 | 1301.00 | 5044.00 |
| | | | Month 3 | 9 | 1 | 2151.22 | 1569.05 | 344.00 | 1086.00 | 2010.00 | 2510.00 | 5502.00 |
| | | gEVAR/Y | Month 1 | 10 | 0 | 750.70 | 647.88 | −348.00 | 466.00 | 613.00 | 1063.00 | 2048.00 |
| | | | Month 2 | 9 | 1 | 1167.22 | 708.40 | −79.00 | 801.00 | 1192.00 | 1802.00 | 1974.00 |
| | | | Month 3 | 10 | 0 | 2510.60 | 1142.73 | 1026.00 | 1562.00 | 2307.50 | 3545.00 | 4153.00 |
| | | VAR/E | Month 1 | 42 | 3 | 106.40 | 368.83 | −361.00 | −83.00 | 54.00 | 126.00 | 1897.00 |
| | | | Month 2 | 43 | 2 | −85.70 | 860.78 | −5429.00 | −81.00 | 0.00 | 159.00 | 634.00 |
| | | | Month 3 | 44 | 1 | 125.25 | 1203.10 | −4856.00 | −80.50 | 0.00 | 137.00 | 4576.00 |
| | | gE/E | Month 1 | 42 | 3 | 617.10 | 907.63 | −49.00 | 128.00 | 312.50 | 692.00 | 3736.00 |
| | | | Month 2 | 43 | 2 | 314.26 | 460.49 | −271.00 | 25.00 | 189.00 | 389.00 | 1723.00 |
| | | | Month 3 | 42 | 3 | 2711.76 | 2304.96 | 0.00 | 1008.00 | 2082.00 | 4222.00 | 10315.00 |
| | | gEVAR/E | Month 1 | 44 | 1 | 543.70 | 465.89 | −111.00 | 104.00 | 508.50 | 826.00 | 1920.00 |
| | | | Month 2 | 45 | 0 | 300.42 | 336.69 | −460.00 | 103.00 | 300.00 | 429.00 | 1088.00 |
| | | | Month 3 | 45 | 0 | 2385.11 | 2307.17 | −460.00 | 819.00 | 1478.00 | 3888.00 | 9485.00 |
| | Varilrix | gE/Y | Month 1 | 9 | 1 | 150.78 | 735.34 | −812.00 | −271.00 | −77.00 | 664.00 | 1263.00 |
| | | | Month 2 | 9 | 1 | 540.56 | 597.57 | −125.00 | 211.00 | 316.00 | 712.00 | 1721.00 |
| | | | Month 3 | 9 | 1 | 609.78 | 735.25 | −565.00 | 377.00 | 576.00 | 895.00 | 1986.00 |
| | | gEVAR/Y | Month 1 | 10 | 0 | −171.70 | 949.81 | −1498.00 | −545.00 | −111.00 | 135.00 | 1991.00 |
| | | | Month 2 | 9 | 1 | 1396.11 | 925.12 | 443.00 | 678.00 | 1111.00 | 1980.00 | 3192.00 |
| | | | Month 3 | 10 | 0 | 1717.20 | 1413.72 | 133.00 | 532.00 | 1356.50 | 2606.00 | 4739.00 |
| | | VAR/E | Month 1 | 42 | 3 | 290.62 | 714.95 | −689.00 | 5.00 | 161.00 | 401.00 | 3784.00 |
| | | | Month 2 | 43 | 2 | 121.05 | 534.68 | −2122.00 | −83.00 | 134.00 | 369.00 | 1492.00 |
| | | | Month 3 | 44 | 1 | 257.48 | 599.43 | −1964.00 | −17.00 | 196.00 | 504.50 | 1857.00 |
| | | gE/E | Month 1 | 42 | 3 | 438.14 | 817.33 | −695.00 | −21.00 | 173.00 | 644.00 | 3233.00 |
| | | | Month 2 | 43 | 2 | 71.42 | 575.91 | −1320.00 | −274.00 | 69.00 | 255.00 | 1678.00 |
| | | | Month 3 | 42 | 3 | 1254.76 | 1389.73 | −548.00 | 382.00 | 827.50 | 1798.00 | 6315.00 |
| | | gEVAR/E | Month 1 | 44 | 1 | 586.45 | 695.20 | −363.00 | 169.50 | 437.50 | 858.00 | 3292.00 |
| | | | Month 2 | 45 | 0 | 420.22 | 582.63 | −416.00 | 78.00 | 185.00 | 545.00 | 2287.00 |
| | | | Month 3 | 45 | 0 | 1648.53 | 1355.42 | 71.00 | 742.00 | 1148.00 | 2418.00 | 5462.00 |
| CD4-TNFα | Pool gE | gE/Y | Month 1 | 9 | 1 | 560.22 | 934.14 | 12.00 | 65.00 | 123.00 | 756.00 | 2903.00 |
| | | | Month 2 | 9 | 1 | 791.78 | 1375.33 | 3.00 | 149.00 | 315.00 | 623.00 | 4378.00 |
| | | | Month 3 | 9 | 1 | 1324.00 | 1590.20 | 206.00 | 415.00 | 831.00 | 1105.00 | 5212.00 |
| | | gEVAR/Y | Month 1 | 10 | 0 | 532.30 | 452.83 | −11.00 | 253.00 | 503.50 | 651.00 | 1572.00 |
| | | | Month 2 | 9 | 1 | 715.00 | 462.65 | 38.00 | 503.00 | 712.00 | 1039.00 | 1314.00 |
| | | | Month 3 | 10 | 0 | 1653.00 | 811.66 | 465.00 | 1195.00 | 1850.50 | 1931.00 | 2902.00 |
| | | VAR/E | Month 1 | 42 | 3 | 51.69 | 229.81 | −470.00 | −57.00 | 41.00 | 115.00 | 1215.00 |
| | | | Month 2 | 43 | 2 | −86.14 | 688.49 | −4412.00 | −46.00 | 2.00 | 126.00 | 254.00 |
| | | | Month 3 | 44 | 1 | 77.75 | 960.07 | −3944.00 | −80.00 | 1.00 | 94.00 | 4212.00 |
| | | gE/E | Month 1 | 42 | 3 | 325.40 | 519.68 | −165.00 | 0.00 | 161.50 | 419.00 | 2302.00 |
| | | | Month 2 | 43 | 2 | 191.19 | 319.19 | −246.00 | 0.00 | 119.00 | 225.00 | 1367.00 |
| | | | Month 3 | 42 | 3 | 1815.83 | 1594.15 | −152.00 | 690.00 | 1389.50 | 2762.00 | 7491.00 |
| | | gEVAR/E | Month 1 | 44 | 1 | 275.16 | 261.28 | −156.00 | 57.50 | 233.50 | 480.00 | 1045.00 |
| | | | Month 2 | 45 | 0 | 164.93 | 267.03 | −494.00 | 26.00 | 126.00 | 316.00 | 675.00 |
| | | | Month 3 | 45 | 0 | 1508.64 | 1548.74 | −433.00 | 508.00 | 875.00 | 2193.00 | 6403.00 |
| | Varilrix | gE/Y | Month 1 | 9 | 1 | 57.67 | 443.72 | −683.00 | −219.00 | 47.00 | 528.00 | 634.00 |
| | | | Month 2 | 9 | 1 | 450.11 | 411.03 | −101.00 | 184.00 | 411.00 | 513.00 | 1364.00 |
| | | | Month 3 | 9 | 1 | 374.89 | 664.84 | −945.00 | 113.00 | 404.00 | 637.00 | 1536.00 |
| | | gEVAR/Y | Month 1 | 10 | 0 | −156.30 | 634.57 | −1203.00 | −365.00 | −107.50 | 217.00 | 941.00 |
| | | | Month 2 | 9 | 1 | 1047.56 | 757.92 | 179.00 | 535.00 | 765.00 | 1585.00 | 2566.00 |
| | | | Month 3 | 10 | 0 | 1200.00 | 918.82 | −123.00 | 626.00 | 1214.50 | 1693.00 | 3132.00 |
| | | VAR/E | Month 1 | 42 | 3 | 250.64 | 695.21 | −805.00 | −33.00 | 138.50 | 281.00 | 3707.00 |
| | | | Month 2 | 43 | 2 | 110.26 | 519.34 | −1984.00 | −121.00 | 103.00 | 294.00 | 1491.00 |
| | | | Month 3 | 44 | 1 | 210.23 | 548.98 | −1984.00 | −10.00 | 167.50 | 423.50 | 1806.00 |
| | | gE/E | Month 1 | 42 | 3 | 298.93 | 637.78 | −566.00 | −45.00 | 146.50 | 405.00 | 2494.00 |
| | | | Month 2 | 43 | 2 | 29.81 | 538.43 | −1359.00 | −171.00 | 13.00 | 150.00 | 1845.00 |
| | | | Month 3 | 42 | 3 | 967.05 | 1085.98 | −609.00 | 239.00 | 707.50 | 1502.00 | 4441.00 |

TABLE C.3-continued

Intracellular Cytokine Staining (ICS): Descriptive Statistics on
CD4 T cells at POST−PRE (Total vaccinated Cohort)

| Test | Antigen | Group | Timing | N | N miss. | Mean | SD | Min | Q1 | Median | Q3 | Max |
|---|---|---|---|---|---|---|---|---|---|---|---|---|
| | | gEVAR/E | Month 1 | 44 | 1 | 405.30 | 604.26 | −432.00 | 90.00 | 304.50 | 554.50 | 2871.00 |
| | | | Month 2 | 45 | 0 | 293.78 | 495.54 | −347.00 | −34.00 | 167.00 | 324.00 | 2242.00 |
| | | | Month 3 | 45 | 0 | 1229.38 | 1061.80 | −73.00 | 492.00 | 913.00 | 1565.00 | 4380.00 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years
N = number of subjects with available results
N miss. = number of subjects with missing results
SD = Standard Deviation
Min, Max = Minimum, Maximum
Q1, Q3 = First, Third quartile

SUPPLEMENTARY TABLE C.3

Intracellular Cytokine Staining (ICS): Descriptive
Statistics on CD8 T cells at POST−PRE (Total vaccinated Cohort)

| Test | Antigen | Group | POST | N | N miss. | Mean | SD | Min | Q1 | Median | Q3 | Max |
|---|---|---|---|---|---|---|---|---|---|---|---|---|
| CD8-ALL DOUBLES | Pool gE | gE/Y | Month 1 | 9 | 1 | 24.00 | 136.52 | −136.00 | −61.00 | 0.00 | 67.00 | 344.00 |
| | | | Month 2 | 9 | 1 | 549.891 | 599.52 | −67.00 | −2.00 | 0.00 | 69.00 | 4810.00 |
| | | | Month 3 | 9 | 1 | 0.89 | 83.03 | −136.00 | −61.00 | 0.00 | 65.00 | 140.00 |
| | | gEVAR/Y | Month 1 | 10 | 0 | −116.70 | 198.88 | −537.00 | −139.00 | −34.00 | 0.00 | 63.00 |
| | | | Month 2 | 9 | 1 | −128.67 | 170.57 | −413.00 | −205.00 | −68.00 | 0.00 | 0.00 |
| | | | Month 3 | 10 | 0 | 26.80 | 117.89 | −142.00 | −68.00 | 0.00 | 69.00 | 271.00 |
| | | VAR/E | Month 1 | 42 | 3 | −13.38 | 97.87 | −278.00 | −65.00 | 0.00 | 0.00 | 210.00 |
| | | | Month 2 | 42 | 3 | −3.50 | 76.50 | −222.00 | −22.00 | 0.00 | 0.00 | 209.00 |
| | | | Month 3 | 44 | 1 | −10.48 | 107.47 | −347.00 | −11.00 | 0.00 | 0.00 | 285.00 |
| | | gE/E | Month 1 | 42 | 3 | 10.45 | 95.31 | −211.00 | 0.00 | 0.00 | 1.00 | 421.00 |
| | | | Month 2 | 43 | 2 | 22.51 | 95.28 | −220.00 | 0.00 | 0.00 | 70.00 | 367.00 |
| | | | Month 3 | 42 | 3 | 7.29 | 88.24 | −211.00 | 0.00 | 0.00 | 0.00 | 460.00 |
| | | gEVAR/E | Month 1 | 42 | 3 | 26.12 | 69.05 | −71.00 | 0.00 | 0.00 | 68.00 | 295.00 |
| | | | Month 2 | 43 | 2 | 16.16 | 62.56 | −147.00 | 0.00 | 0.00 | 67.00 | 201.00 |
| | | | Month 3 | 43 | 2 | 65.00 | 217.39 | −219.00 | 0.00 | 0.00 | 70.00 | 1134.00 |
| | Varilrix | gE/Y | Month 1 | 9 | 1 | 88.78 | 274.69 | −67.00 | −1.00 | 0.00 | 0.00 | 817.00 |
| | | | Month 2 | 9 | 1 | 484.11 | 1376.23 | −1.00 | 0.00 | 1.00 | 68.00 | 4153.00 |
| | | | Month 3 | 9 | 1 | −86.78 | 246.23 | −707.00 | −68.00 | 0.00 | 0.00 | 135.00 |
| | | gEVAR/Y | Month 1 | 10 | 0 | −20.80 | 71.94 | −141.00 | −66.00 | 0.00 | 0.00 | 133.00 |
| | | | Month 2 | 9 | 1 | 30.44 | 143.10 | −213.00 | −66.00 | 0.00 | 139.00 | 273.00 |
| | | | Month 3 | 10 | 0 | 56.10 | 163.61 | −213.00 | 0.00 | 35.00 | 140.00 | 414.00 |
| | | VAR/E | Month 1 | 42 | 3 | −31.67 | 340.22 | −1801.00 | −71.00 | 0.00 | 74.00 | 491.00 |
| | | | Month 2 | 43 | 2 | −52.51 | 298.58 | −1664.00 | −68.00 | 0.00 | 68.00 | 362.00 |
| | | | Month 3 | 44 | 1 | 131.75 | 725.55 | −611.00 | −26.00 | 0.00 | 104.50 | 4674.00 |
| | | gE/E | Month 1 | 42 | 3 | 59.62 | 265.24 | −296.00 | −72.00 | 0.00 | 81.00 | 1015.00 |
| | | | Month 2 | 43 | 2 | −10.51 | 382.79 | −1736.00 | −42.00 | 0.00 | 71.00 | 1242.00 |
| | | | Month 3 | 42 | 3 | 28.60 | 190.71 | −423.00 | −71.00 | 0.00 | 72.00 | 597.00 |
| | | gEVAR/E | Month 1 | 42 | 3 | 5.90 | 351.50 | −1924.00 | −1.00 | 0.00 | 73.00 | 694.00 |
| | | | Month 2 | 43 | 2 | 15.98 | 365.42 | −1594.00 | −70.00 | 0.00 | 143.00 | 1213.00 |
| | | | Month 3 | 43 | 2 | 129.19 | 225.91 | −149.00 | 0.00 | 16.00 | 265.00 | 916.00 |
| CD8-CD40L | Pool gE | gE/Y | Month 1 | 9 | 1 | 24.11 | 127.75 | −67.00 | −61.00 | 0.00 | 0.00 | 344.00 |
| | | | Month 2 | 9 | 1 | 535.00 | 1604.13 | −67.00 | 0.00 | 0.00 | 0.00 | 4810.00 |
| | | | Month 3 | 9 | 1 | −13.89 | 55.72 | −67.00 | −67.00 | 0.00 | 0.00 | 69.00 |
| | | gEVAR/Y | Month 1 | 10 | 0 | −95.80 | 189.16 | −469.00 | −139.00 | 0.00 | 0.00 | 63.00 |
| | | | Month 2 | 9 | 1 | −113.11 | 179.39 | −413.00 | −205.00 | 0.00 | 0.00 | 0.00 |
| | | | Month 3 | 10 | 0 | 34.10 | 138.26 | −210.00 | 0.00 | 0.00 | 69.00 | 339.00 |
| | | VAR/E | Month 1 | 42 | 3 | −4.40 | 43.17 | −141.00 | 0.00 | 0.00 | 0.00 | 152.00 |
| | | | Month 2 | 42 | 3 | −7.29 | 37.64 | −141.00 | 0.00 | 0.00 | 0.00 | 104.00 |
| | | | Month 3 | 44 | 1 | −0.77 | 37.03 | −73.00 | 0.00 | 0.00 | 0.00 | 102.00 |
| | | gE/E | Month 1 | 42 | 3 | 1.45 | 39.39 | −75.00 | 0.00 | 0.00 | 0.00 | 76.00 |
| | | | Month 2 | 43 | 2 | 6.33 | 45.80 | −75.00 | 0.00 | 0.00 | 0.00 | 145.00 |
| | | | Month 3 | 42 | 3 | −1.93 | 36.10 | −75.00 | 0.00 | 0.00 | 0.00 | 72.00 |
| | | gEVAR/E | Month 1 | 42 | 3 | 10.86 | 48.91 | −70.00 | 0.00 | 0.00 | 0.00 | 220.00 |
| | | | Month 2 | 43 | 2 | 16.56 | 45.02 | −70.00 | 0.00 | 0.00 | 65.00 | 145.00 |
| | | | Month 3 | 43 | 2 | 40.72 | 152.63 | −70.00 | 0.00 | 0.00 | 0.00 | 779.00 |
| | Varilrix | gE/Y | Month 1 | 9 | 1 | −24.78 | 56.16 | −138.00 | −67.00 | 0.00 | 0.00 | 51.00 |
| | | | Month 2 | 9 | 1 | 30.67 | 102.65 | −68.00 | −1.00 | 0.00 | 69.00 | 272.00 |
| | | | Month 3 | 9 | 1 | −19.78 | 46.08 | −73.00 | −67.00 | 0.00 | 0.00 | 68.00 |
| | | gEVAR/Y | Month 1 | 10 | 0 | −20.00 | 32.21 | −68.00 | −66.00 | 0.00 | 0.00 | 0.00 |
| | | | Month 2 | 9 | 1 | 0.78 | 68.53 | −68.00 | −66.00 | 0.00 | 0.00 | 141.00 |
| | | | Month 3 | 10 | 0 | 41.60 | 134.83 | −68.00 | 0.00 | 0.00 | 0.00 | 414.00 |

SUPPLEMENTARY TABLE C.3-continued

Intracellular Cytokine Staining (ICS): Descriptive
Statistics on CD8 T cells at POST−PRE (Total vaccinated Cohort)

| Test | Antigen | Group | POST | N | N miss. | Mean | SD | Min | Q1 | Median | Q3 | Max |
|---|---|---|---|---|---|---|---|---|---|---|---|---|
| | | VAR/E | Month 1 | 42 | 3 | 16.17 | 63.26 | −72.00 | 0.00 | 0.00 | 0.00 | 260.00 |
| | | | Month 2 | 43 | 2 | 2.09 | 48.77 | −73.00 | 0.00 | 0.00 | 0.00 | 153.00 |
| | | | Month 3 | 44 | 1 | 2.34 | 43.59 | −73.00 | 0.00 | 0.00 | 0.00 | 146.00 |
| | | gE/E | Month 1 | 42 | 3 | 2.14 | 80.48 | −149.00 | 0.00 | 0.00 | 0.00 | 362.00 |
| | | | Month 2 | 43 | 2 | −11.23 | 59.14 | −218.00 | 0.00 | 0.00 | 0.00 | 152.00 |
| | | | Month 3 | 42 | 3 | −1.93 | 76.17 | −226.00 | 0.00 | 0.00 | 0.00 | 217.00 |
| | | gEVAR/E | Month 1 | 42 | 3 | 3.05 | 51.88 | −135.00 | 0.00 | 0.00 | 0.00 | 157.00 |
| | | | Month 2 | 43 | 2 | −12.88 | 47.07 | −145.00 | 0.00 | 0.00 | 0.00 | 78.00 |
| | | | Month 3 | 43 | 2 | −4.91 | 46.80 | −145.00 | 0.00 | 0.00 | 0.00 | 73.00 |
| CD8-IFNγ | Pool gE | gE/Y | Month 1 | 9 | 1 | 23.22 | 45.52 | −61.00 | 0.00 | 4.00 | 66.00 | 67.00 |
| | | | Month 2 | 9 | 1 | 200.56 | 477.92 | −61.00 | 0.00 | 67.00 | 133.00 | 1463.00 |
| | | | Month 3 | 9 | 1 | 15.89 | 65.31 | −67.00 | 0.00 | 0.00 | 65.00 | 140.00 |
| | | gEVAR/Y | Month 1 | 10 | 0 | −75.50 | 120.41 | −335.00 | −142.00 | −34.00 | 0.00 | 63.00 |
| | | | Month 2 | 9 | 1 | −68.11 | 59.39 | −142.00 | −131.00 | −67.00 | 0.00 | 0.00 |
| | | | Month 3 | 10 | 0 | −27.00 | 56.93 | −134.00 | −68.00 | 0.00 | 0.00 | 67.00 |
| | | VAR/E | Month 1 | 42 | 3 | −15.52 | 75.76 | −278.00 | 0.00 | 0.00 | 0.00 | 193.00 |
| | | | Month 2 | 42 | 3 | 2.43 | 62.84 | −139.00 | 0.00 | 0.00 | 0.00 | 192.00 |
| | | | Month 3 | 44 | 1 | −15.32 | 79.50 | −347.00 | 0.00 | 0.00 | 0.00 | 75.00 |
| | | gE/E | Month 1 | 42 | 3 | 16.93 | 72.52 | −109.00 | 0.00 | 0.00 | 0.00 | 282.00 |
| | | | Month 2 | 43 | 2 | 23.58 | 84.49 | −109.00 | 0.00 | 0.00 | 65.00 | 367.00 |
| | | | Month 3 | 42 | 3 | 18.57 | 70.71 | −66.00 | 0.00 | 0.00 | 0.00 | 392.00 |
| | | gEVAR/E | Month 1 | 42 | 3 | 13.55 | 62.27 | −146.00 | 0.00 | 0.00 | 0.00 | 229.00 |
| | | | Month 2 | 43 | 2 | −0.47 | 40.58 | −147.00 | 0.00 | 0.00 | 0.00 | 74.00 |
| | | | Month 3 | 43 | 2 | 48.56 | 146.44 | −144.00 | 0.00 | 0.00 | 68.00 | 781.00 |
| | Varilrix | gE/Y | Month 1 | 9 | 1 | 86.67 | 344.40 | −284.00 | 0.00 | 0.00 | 0.00 | 962.00 |
| | | | Month 2 | 9 | 1 | 460.11 | 1388.68 | −215.00 | 0.00 | 0.00 | 66.00 | 4155.00 |
| | | | Month 3 | 9 | 1 | −71.22 | 165.93 | −425.00 | 0.00 | 0.00 | 0.00 | 68.00 |
| | | gEVAR/Y | Month 1 | 10 | 0 | −20.70 | 71.64 | −139.00 | −67.00 | 0.00 | 0.00 | 133.00 |
| | | | Month 2 | 9 | 1 | 6.78 | 136.42 | −282.00 | −1.00 | 0.00 | 67.00 | 204.00 |
| | | | Month 3 | 10 | 0 | 28.90 | 155.44 | −282.00 | 0.00 | 0.50 | 146.00 | 273.00 |
| | | VAR/E | Month 1 | 42 | 3 | −23.81 | 304.92 | −1513.00 | 0.00 | 0.00 | 73.00 | 561.00 |
| | | | Month 2 | 43 | 2 | −53.65 | 284.04 | −1449.00 | 0.00 | 0.00 | 65.00 | 289.00 |
| | | | Month 3 | 44 | 1 | 121.93 | 758.36 | −610.00 | 0.00 | −0.50 | 73.00 | 4889.00 |
| | | gE/E | Month 1 | 42 | 3 | 74.10 | 267.93 | −296.00 | −2.00 | 0.00 | 71.00 | 1088.00 |
| | | | Month 2 | 43 | 2 | −4.00 | 372.80 | −1652.00 | −66.00 | 0.00 | 68.00 | 1170.00 |
| | | | Month 3 | 42 | 3 | 37.74 | 175.85 | −339.00 | −3.00 | 0.00 | 74.00 | 670.00 |
| | | gEVAR/E | Month 1 | 42 | 3 | −0.81 | 360.67 | −1999.00 | 0.00 | 0.00 | 73.00 | 694.00 |
| | | | Month 2 | 43 | 2 | 16.63 | 341.39 | −1452.00 | −66.00 | 0.00 | 72.00 | 1213.00 |
| | | | Month 3 | 43 | 2 | 119.21 | 197.20 | −284.00 | 0.00 | 16.00 | 221.00 | 659.00 |
| CD8-IL2 | Pool gE | gE/Y | Month 1 | 9 | 1 | 39.11 | 127.97 | −67.00 | −61.00 | 0.00 | 67.00 | 344.00 |
| | | | Month 2 | 9 | 1 | 535.00 | 1604.48 | −67.00 | −61.00 | 0.00 | 67.00 | 4810.00 |
| | | | Month 3 | 9 | 1 | 8.67 | 71.13 | −67.00 | −61.00 | 0.00 | 65.00 | 140.00 |
| | | gEVAR/Y | Month 1 | 10 | 0 | −102.60 | 186.54 | −469.00 | −139.00 | 0.00 | 0.00 | 63.00 |
| | | | Month 2 | 9 | 1 | −113.00 | 162.73 | −413.00 | −205.00 | 0.00 | 0.00 | 0.00 |
| | | | Month 3 | 10 | 0 | 33.80 | 125.98 | −142.00 | 0.00 | 0.00 | 69.00 | 339.00 |
| | | VAR/E | Month 1 | 42 | 3 | −7.79 | 57.52 | −148.00 | 0.00 | 0.00 | 0.00 | 152.00 |
| | | | Month 2 | 42 | 3 | −2.90 | 68.64 | −222.00 | 0.00 | 0.00 | 0.00 | 211.00 |
| | | | Month 3 | 44 | 1 | −4.02 | 64.96 | −222.00 | 0.00 | 0.00 | 0.00 | 151.00 |
| | | gE/E | Month 1 | 42 | 3 | 2.00 | 52.68 | −211.00 | 0.00 | 0.00 | 0.00 | 139.00 |
| | | | Month 2 | 43 | 2 | 13.28 | 64.17 | −211.00 | 0.00 | 0.00 | 65.00 | 218.00 |
| | | | Month 3 | 42 | 3 | −4.19 | 59.14 | −211.00 | 0.00 | 0.00 | 0.00 | 228.00 |
| | | gEVAR/E | Month 1 | 42 | 3 | 19.67 | 59.09 | −70.00 | 0.00 | 0.00 | 11.00 | 220.00 |
| | | | Month 2 | 43 | 2 | 18.05 | 48.05 | −70.00 | 0.00 | 0.00 | 65.00 | 148.00 |
| | | | Month 3 | 43 | 2 | 40.63 | 153.41 | −66.00 | 0.00 | 0.00 | 0.00 | 850.00 |
| | Varilrix | gE/Y | Month 1 | 9 | 1 | 49.00 | 156.22 | −67.00 | 0.00 | 0.00 | 0.00 | 458.00 |
| | | | Month 2 | 9 | 1 | 125.00 | 298.57 | −1.00 | 0.00 | 0.00 | 70.00 | 916.00 |
| | | | Month 3 | 9 | 1 | −9.22 | 73.85 | −81.00 | −68.00 | 0.00 | 0.00 | 136.00 |
| | | gEVAR/Y | Month 1 | 10 | 0 | −6.80 | 37.82 | −68.00 | 0.00 | 0.00 | 0.00 | 66.00 |
| | | | Month 2 | 9 | 1 | 23.22 | 76.53 | −68.00 | 0.00 | 0.00 | 66.00 | 141.00 |
| | | | Month 3 | 10 | 0 | 48.20 | 155.17 | −68.00 | 0.00 | 0.00 | 0.00 | 480.00 |
| | | VAR/E | Month 1 | 42 | 3 | −23.52 | 167.46 | −648.00 | −67.00 | 0.00 | 69.00 | 211.00 |
| | | | Month 2 | 43 | 2 | −10.63 | 110.07 | −289.00 | −72.00 | 0.00 | 1.00 | 361.00 |
| | | | Month 3 | 44 | 1 | 46.75 | 299.86 | −687.00 | 0.00 | 0.00 | 69.00 | 1771.00 |
| | | gE/E | Month 1 | 42 | 3 | −10.98 | 155.68 | −266.00 | −110.00 | 0.00 | 0.00 | 539.00 |
| | | | Month 2 | 43 | 2 | −40.56 | 207.85 | −1030.00 | −72.00 | 0.00 | 0.00 | 367.00 |
| | | | Month 3 | 42 | 3 | 13.12 | 137.98 | −226.00 | −71.00 | 0.00 | 60.00 | 662.00 |
| | | gEVAR/E | Month 1 | 42 | 3 | 21.33 | 123.99 | −425.00 | −2.00 | 0.00 | 71.00 | 488.00 |
| | | | Month 2 | 43 | 2 | 29.33 | 179.40 | −301.00 | −66.00 | 0.00 | 68.00 | 831.00 |
| | | | Month 3 | 43 | 2 | 86.84 | 165.87 | −136.00 | 0.00 | 0.00 | 199.00 | 709.00 |
| CD8-TNFα | Pool gE | gE/Y | Month 1 | 9 | 1 | −22.33 | 33.50 | −67.00 | −67.00 | 0.00 | 0.00 | 0.00 |
| | | | Month 2 | 9 | 1 | −7.44 | 40.26 | −67.00 | 0.00 | 0.00 | 0.00 | 67.00 |
| | | | Month 3 | 9 | 1 | 0.56 | 59.77 | −67.00 | −1.00 | 0.00 | 0.00 | 140.00 |
| | | gEVAR/Y | Month 1 | 10 | 0 | −34.00 | 65.20 | −200.00 | −67.00 | 0.00 | 0.00 | 0.00 |
| | | | Month 2 | 9 | 1 | −30.22 | 68.11 | −200.00 | 0.00 | 0.00 | 0.00 | 1.00 |
| | | | Month 3 | 10 | 0 | −27.00 | 71.95 | −200.00 | −67.00 | 0.00 | 0.00 | 67.00 |

SUPPLEMENTARY TABLE C.3-continued

Intracellular Cytokine Staining (ICS): Descriptive
Statistics on CD8 T cells at POST−PRE (Total vaccinated Cohort)

| Test | Antigen | Group | POST | N | N miss. | Mean | SD | Min | Q1 | Median | Q3 | Max |
|---|---|---|---|---|---|---|---|---|---|---|---|---|
| | | VAR/E | Month 1 | 42 | 3 | −6.71 | 90.36 | −278.00 | 0.00 | 0.00 | 0.00 | 210.00 |
| | | | Month 2 | 42 | 3 | −6.67 | 78.03 | −219.00 | −1.00 | 0.00 | 0.00 | 209.00 |
| | | | Month 3 | 44 | 1 | −11.98 | 89.66 | −347.00 | 0.00 | 0.00 | 0.00 | 206.00 |
| | | gE/E | Month 1 | 42 | 3 | 12.95 | 86.37 | −184.00 | 0.00 | 0.00 | 7.00 | 421.00 |
| | | | Month 2 | 43 | 2 | 10.81 | 69.64 | −220.00 | 0.00 | 0.00 | 65.00 | 220.00 |
| | | | Month 3 | 42 | 3 | 5.45 | 65.44 | −140.00 | 0.00 | 0.00 | 0.00 | 305.00 |
| | | gEVAR/E | Month 1 | 42 | 3 | 14.10 | 72.50 | −219.00 | 0.00 | 0.00 | 0.00 | 229.00 |
| | | | Month 2 | 43 | 2 | 6.28 | 57.99 | −219.00 | 0.00 | 0.00 | 0.00 | 148.00 |
| | | | Month 3 | 43 | 2 | 39.09 | 129.10 | −219.00 | 0.00 | 0.00 | 68.00 | 639.00 |
| | Varilrix | gE/Y | Month 1 | 9 | 1 | 76.33 | 232.77 | −71.00 | 0.00 | 0.00 | 0.00 | 690.00 |
| | | | Month 2 | 9 | 1 | 468.78 | 1436.63 | −143.00 | 0.00 | 0.00 | 0.00 | 4297.00 |
| | | | Month 3 | 9 | 1 | −86.11 | 218.67 | −632.00 | −1.00 | 0.00 | 0.00 | 70.00 |
| | | gEVAR/Y | Month 1 | 10 | 0 | −14.10 | 70.26 | −141.00 | −66.00 | 0.00 | 0.00 | 133.00 |
| | | | Month 2 | 9 | 1 | 29.89 | 146.91 | −213.00 | −66.00 | 0.00 | 69.00 | 273.00 |
| | | | Month 3 | 10 | 0 | 8.60 | 118.21 | −213.00 | −66.00 | 0.00 | 72.00 | 214.00 |
| | | VAR/E | Month 1 | 42 | 3 | −40.52 | 354.84 | −1873.00 | −68.00 | 0.00 | 69.00 | 491.00 |
| | | | Month 2 | 43 | 2 | −51.70 | 327.59 | −1961.00 | 0.00 | 0.00 | 6.00 | 361.00 |
| | | | Month 3 | 44 | 1 | 110.00 | 653.00 | −991.00 | 0.00 | 0.00 | 73.00 | 4087.00 |
| | | gE/E | Month 1 | 42 | 3 | 52.86 | 220.80 | −455.00 | −4.00 | 0.00 | 71.00 | 869.00 |
| | | | Month 2 | 43 | 2 | 17.14 | 356.23 | −1493.00 | −19.00 | 0.00 | 71.00 | 1312.00 |
| | | | Month 3 | 42 | 3 | 15.07 | 172.57 | −571.00 | 0.00 | 0.00 | 70.00 | 449.00 |
| | | gEVAR/E | Month 1 | 42 | 3 | 15.48 | 312.96 | −1711.00 | 0.00 | 0.00 | 134.00 | 694.00 |
| | | | Month 2 | 43 | 2 | 10.81 | 297.77 | −1440.00 | −66.00 | 0.00 | 67.00 | 838.00 |
| | | | Month 3 | 43 | 2 | 109.00 | 211.09 | −148.00 | 0.00 | 0.00 | 205.00 | 904.00 | gE/Y = gE-AS1/18-30 years;
gEVAR/Y = gE-AS1 + Varilrix/18-30 years
VAR/E = Varilrix/50-70 years;
gE/E = gE-AS1/50-70 years;
gEVAR/E = gE-AS1 + Varilrix/50-70 years
N = number of subjects with available results;
N miss. = number of subjects with missing results
SD = Standard Deviation
Min, Max = Minimum, Maximum
Q1, Q3 = First, Third quartile

TABLE C.4

Intracellular Cytokine Staining (ICS): Inferential statistics: P-values from Kruskal-Wallis Tests for CD4 T cells at POST-PRE (Total Vaccinated Cohort)

| T cells | Groups compared | Antigen | Test | P_value at Month 1-PRE | P_value at Month 2-PRE | P_value at Month 3-PRE |
|---|---|---|---|---|---|---|
| CD4 | VAR\E and gEVAR\E | Pool gE | ALL DOUBLES | 0.0000 | 0.0004 | 0.0000 |
| | | | CD40L | 0.0000 | 0.0002 | 0.0000 |
| | | | IFNγ | 0.0000 | 0.0429 | 0.0000 |
| | | | IL2 | 0.0000 | 0.0000 | 0.0000 |
| | | | TNFα | 0.0000 | 0.0009 | 0.0000 |
| | | Varilrix | ALL DOUBLES | 0.0078 | 0.1736 | 0.0000 |
| | | | CD40L | 0.0090 | 0.0727 | 0.0000 |
| | | | IFNγ | 0.0261 | 0.0447 | 0.0000 |
| | | | IL2 | 0.0067 | 0.0575 | 0.0000 |
| | | | TNFα | 0.0620 | 0.1957 | 0.0000 |
| | VAR\E and gE\E | Pool gE | ALL DOUBLES | 0.0000 | 0.0004 | 0.0000 |
| | | | CD40L | 0.0000 | 0.0001 | 0.0000 |
| | | | IFNγ | 0.0001 | 0.0880 | 0.0000 |
| | | | IL2 | 0.0000 | 0.0003 | 0.0000 |
| | | | TNFα | 0.0009 | 0.0018 | 0.0000 |
| | | Varilrix | ALL DOUBLES | 0.5370 | 0.1120 | 0.0000 |
| | | | CD40L | 0.5137 | 0.2217 | 0.0000 |
| | | | IFNγ | 0.7205 | 0.2367 | 0.0000 |
| | | | IL2 | 0.5791 | 0.3599 | 0.0000 |
| | | | TNFα | 0.8440 | 0.0880 | 0.0001 |
| | gE\E and gEVAR\E | Pool gE | ALL DOUBLES | 0.3100 | 0.6612 | 0.3060 |
| | | | CD40L | 0.3996 | 0.7134 | 0.3350 |
| | | | IFNγ | 0.2366 | 0.7134 | 0.6835 |
| | | | IL2 | 0.4707 | 0.3629 | 0.4148 |
| | | | TNFα | 0.3923 | 0.7134 | 0.2480 |

TABLE C.4-continued

Intracellular Cytokine Staining (ICS): Inferential statistics: P-values from Kruskal-Wallis Tests for CD4 T cells at POST-PRE (Total Vaccinated Cohort)

| T cells | Groups compared | Antigen | Test | P_value at Month 1-PRE | P_value at Month 2-PRE | P_value at Month 3-PRE |
|---|---|---|---|---|---|---|
| | | Varilrix | ALL DOUBLES | 0.1034 | 0.0049 | 0.1231 |
| | | | CD40L | 0.1262 | 0.0054 | 0.1305 |
| | | | IFNγ | 0.0832 | 0.0021 | 0.0910 |
| | | | IL2 | 0.0921 | 0.0040 | 0.0831 |
| | | | TNFα | 0.1179 | 0.0035 | 0.1372 |

VAR/E = Varilrix/50-70 years
gE/E = gE-AS1/50-70 years
gEVAR/E = gE-AS1 + Varilrix/50-70 years

SUPPLEMENTARY TABLE C.4

Intracellular Cytokine Staining (ICS): Inferential statistics: P-values from Kruskal-Wallis Tests for CD8 T cells at POST-PRE (Total Vaccinated Cohort)

| T cells | Groups compared | Antigen | Test description | P_value at Month 1-PRE | P_value at Month 2-PRE | P_value at Month 3-PRE |
|---|---|---|---|---|---|---|
| CD8 | VAR\E and gEVAR\E | Pool gE | ALL DOUBLES | 0.0575 | 0.2069 | 0.1364 |
| | | | CD40L | 0.1647 | 0.0113 | 0.1579 |
| | | | IFNγ | 0.1411 | 0.8759 | 0.0360 |
| | | | IL2 | 0.0456 | 0.1080 | 0.1442 |
| | | | TNFα | 0.2938 | 0.3356 | 0.0499 |
| | | Varilrix | ALL DOUBLES | 0.6363 | 0.8116 | 0.1785 |
| | | | CD40L | 0.6944 | 0.4151 | 0.9266 |
| | | | IFNγ | 0.5953 | 0.8108 | 0.0486 |
| | | | IL2 | 0.6656 | 0.5567 | 0.1544 |
| | | | TNFα | 0.3677 | 0.8788 | 0.2679 |
| | VAR\E and gE\E | Pool gE | ALL DOUBLES | 0.2913 | 0.1159 | 0.9259 |
| | | | CD40L | 0.5885 | 0.2542 | 0.9217 |
| | | | IFNγ | 0.1900 | 0.3113 | 0.4158 |
| | | | IL2 | 0.1687 | 0.1288 | 0.8127 |
| | | | TNFα | 0.3700 | 0.2008 | 0.8454 |
| | | Varilrix | ALL DOUBLES | 0.9067 | 0.9436 | 0.4197 |
| | | | CD40L | 0.1382 | 0.4574 | 0.7783 |
| | | | IFNγ | 0.7445 | 0.6841 | 0.8567 |
| | | | IL2 | 0.1893 | 0.3980 | 0.3536 |
| | | | TNFα | 0.6716 | 0.8132 | 0.6206 |
| | gE\E and gEVAR\E | Pool gE | ALL DOUBLES | 0.3308 | 0.6165 | 0.1380 |
| | | | CD40L | 0.4801 | 0.2231 | 0.1503 |
| | | | IFNγ | 0.9259 | 0.2911 | 0.1157 |
| | | | IL2 | 0.4306 | 1.0000 | 0.0678 |
| | | | TNFα | 0.9797 | 0.6343 | 0.0646 |
| | | Varilrix | ALL DOUBLES | 0.5447 | 0.7670 | 0.0227 |
| | | | CD40L | 0.2490 | 0.9913 | 0.8265 |
| | | | IFNγ | 0.4940 | 0.5395 | 0.0801 |
| | | | IL2 | 0.0705 | 0.1827 | 0.0264 |
| | | | TNFα | 0.6200 | 0.7754 | 0.1098 |

VAR/E = Varilrix/50-70 years
gE/E = gE-AS1/50-70 years
gEVAR/E = gE-AS1 + Varilrix/50-70 years Lymphoproliferation Tables

LIST OF TABLES

| | | PAGE |
|---|---|---|
| Table L.1 | Descriptive statistics on the Stimulating Index for lymphoproliferation (ATP cohort for immunogenicity) . . . | |
| Table L.2 | Lymphoproliferation: Geometric Mean (ATP cohort for immunogenicity) . . . | |
| Table L.3 | Lymphoproliferation: Inferential statistics on Stimultaing Index (ATP cohort for immunogenicity) . . . | |
| Table L.4 | Lymphoproliferation: Fold increase in Geometric Mean (GMR) (ATP cohort for immunogenicity) . . . | |

TABLE L.1

Descriptive statistics on the Stimulating Index for lymphoproliferation (ATP cohort for immunogenicity)

| Concentration | Stimulating Antigen | Group | Timing | N | N miss. | Mean | SD | Min | Q1 | Median | Q3 | Max |
|---|---|---|---|---|---|---|---|---|---|---|---|---|
| 0.1 CPAU/ml | VZV | VAR/E | Day 0 | 44 | 1 | 27.40 | 35.81 | 1.06 | 9.90 | 17.22 | 33.96 | 221.53 |
| | | | Month 1 | 44 | 1 | 29.82 | 25.70 | 0.94 | 9.36 | 23.66 | 45.66 | 92.16 |
| | | | Month 2 | 43 | 2 | 27.50 | 17.97 | 5.61 | 13.90 | 24.01 | 34.62 | 95.32 |
| | | | Month 3 | 43 | 2 | 29.34 | 24.53 | 6.72 | 13.62 | 20.55 | 36.93 | 124.46 |
| | | gE/E | Day 0 | 43 | 2 | 21.86 | 17.72 | 1.21 | 9.66 | 17.76 | 28.15 | 91.05 |
| | | | Month 1 | 42 | 3 | 28.36 | 23.99 | 2.55 | 12.13 | 21.85 | 31.99 | 107.18 |
| | | | Month 2 | 42 | 3 | 27.47 | 22.90 | 1.62 | 14.85 | 20.71 | 32.88 | 138.04 |
| | | | Month 3 | 42 | 3 | 28.52 | 17.80 | 2.16 | 15.28 | 24.92 | 40.87 | 87.26 |
| | | gE/Y | Day 0 | 10 | 0 | 37.50 | 16.31 | 9.36 | 28.85 | 33.88 | 43.11 | 67.30 |
| | | | Month 1 | 9 | 1 | 42.87 | 28.45 | 5.42 | 24.89 | 38.04 | 44.23 | 102.82 |
| | | | Month 2 | 10 | 0 | 47.78 | 29.73 | 12.35 | 24.79 | 42.91 | 63.27 | 108.21 |
| | | | Month 3 | 10 | 0 | 47.77 | 25.64 | 8.87 | 25.98 | 44.79 | 74.27 | 82.49 |
| | | gEVAR/E | Day 0 | 42 | 2 | 19.30 | 21.14 | 1.35 | 6.27 | 17.79 | 22.49 | 136.88 |
| | | | Month 1 | 42 | 2 | 28.63 | 18.39 | 3.31 | 15.08 | 21.69 | 44.13 | 68.92 |
| | | | Month 2 | 42 | 2 | 30.92 | 24.15 | 1.97 | 11.97 | 23.06 | 49.92 | 96.33 |
| | | | Month 3 | 43 | 1 | 37.51 | 29.04 | 4.45 | 19.92 | 29.98 | 43.02 | 142.50 |
| | | gEVARY | Day 0 | 10 | 0 | 49.64 | 22.42 | 29.45 | 39.22 | 41.28 | 57.67 | 106.72 |
| | | | Month 1 | 10 | 0 | 54.43 | 29.44 | 18.42 | 27.53 | 49.96 | 77.50 | 105.66 |
| | | | Month 2 | 9 | 1 | 51.83 | 24.74 | 11.07 | 34.87 | 52.85 | 74.34 | 82.69 |
| | | | Month 3 | 10 | 0 | 47.69 | 21.37 | 16.19 | 34.27 | 50.79 | 66.25 | 77.75 |
| 1 CPAU/ml | VZV | VAR/E | Day 0 | 44 | 1 | 35.73 | 29.28 | 0.81 | 15.47 | 27.32 | 49.16 | 143.45 |
| | | | Month 1 | 44 | 1 | 43.08 | 28.02 | 1.58 | 22.67 | 34.43 | 58.49 | 122.15 |
| | | | Month 2 | 43 | 2 | 50.16 | 87.00 | 12.27 | 23.16 | 34.68 | 41.08 | 586.25 |
| | | | Month 3 | 43 | 2 | 36.02 | 23.73 | 8.56 | 17.36 | 28.63 | 46.93 | 116.31 |
| | | gE/E | Day 0 | 43 | 2 | 32.54 | 26.56 | 4.59 | 17.91 | 27.88 | 39.18 | 139.71 |
| | | | Month 1 | 42 | 3 | 35.02 | 25.59 | 1.54 | 19.97 | 28.32 | 37.30 | 110.93 |
| | | | Month 2 | 42 | 3 | 35.73 | 22.52 | 1.46 | 21.91 | 31.20 | 41.19 | 107.68 |
| | | | Month 3 | 42 | 3 | 37.34 | 19.84 | 8.37 | 20.36 | 32.55 | 52.92 | 85.04 |
| | | gE/Y | Day 0 | 10 | 0 | 43.97 | 23.26 | 9.30 | 31.05 | 43.43 | 53.02 | 87.99 |
| | | | Month 1 | 9 | 1 | 51.10 | 35.47 | 6.31 | 37.60 | 44.42 | 57.47 | 132.58 |
| | | | Month 2 | 10 | 0 | 54.24 | 20.58 | 16.73 | 44.20 | 51.53 | 71.02 | 88.07 |
| | | | Month 3 | 10 | 0 | 56.04 | 37.19 | 13.72 | 35.84 | 45.31 | 68.27 | 143.80 |
| | | gEVAR/E | Day 0 | 42 | 2 | 29.13 | 24.91 | 1.20 | 12.54 | 23.70 | 39.25 | 146.46 |
| | | | Month 1 | 42 | 2 | 39.10 | 23.60 | 3.01 | 22.28 | 33.18 | 52.91 | 108.05 |
| | | | Month 2 | 42 | 2 | 41.11 | 26.67 | 7.67 | 21.90 | 35.00 | 55.75 | 126.34 |
| | | | Month 3 | 43 | 1 | 46.67 | 33.81 | 3.98 | 24.34 | 35.11 | 64.97 | 151.51 |
| | | gEVAR/Y | Day 0 | 10 | 0 | 59.60 | 32.75 | 27.66 | 39.90 | 46.26 | 75.47 | 138.10 |
| | | | Month 1 | 10 | 0 | 71.90 | 45.92 | 21.95 | 24.54 | 61.95 | 117.28 | 145.08 |
| | | | Month 2 | 9 | 1 | 68.71 | 36.16 | 28.77 | 34.89 | 69.01 | 94.82 | 128.29 |
| | | | Month 3 | 10 | 0 | 67.50 | 34.90 | 18.29 | 36.67 | 62.03 | 92.64 | 118.24 |
| 20 µg/ml | gE | VAR/E | Day 0 | 44 | 1 | 2.85 | 3.08 | 0.77 | 1.24 | 1.68 | 2.81 | 14.30 |
| | | | Month 1 | 44 | 1 | 3.53 | 3.87 | 0.57 | 1.34 | 2.03 | 4.31 | 20.96 |
| | | | Month 2 | 43 | 2 | 4.09 | 5.08 | 0.86 | 1.54 | 2.12 | 4.64 | 30.33 |
| | | | Month 3 | 43 | 2 | 3.66 | 3.01 | 0.60 | 1.53 | 2.48 | 5.72 | 14.05 |
| | | gE/E | Day 0 | 43 | 2 | 3.45 | 5.78 | 0.78 | 1.11 | 1.93 | 2.99 | 37.21 |
| | | | Month 1 | 42 | 3 | 12.69 | 10.72 | 0.76 | 5.41 | 8.88 | 17.63 | 45.95 |
| | | | Month 2 | 42 | 3 | 11.76 | 11.43 | 0.93 | 4.35 | 8.44 | 14.46 | 51.08 |
| | | | Month 3 | 42 | 3 | 30.34 | 21.83 | 1.97 | 15.69 | 21.16 | 40.12 | 101.46 |
| | | gE/Y | Day 0 | 10 | 0 | 2.62 | 1.24 | 1.01 | 1.75 | 2.18 | 3.71 | 4.88 |
| | | | Month 1 | 9 | 1 | 19.09 | 15.69 | 2.17 | 6.67 | 13.12 | 35.81 | 43.15 |
| | | | Month 2 | 10 | 0 | 25.50 | 18.51 | 9.37 | 10.31 | 16.67 | 32.61 | 60.58 |
| | | | Month 3 | 10 | 0 | 37.46 | 21.69 | 4.72 | 27.78 | 31.11 | 52.84 | 76.56 |
| | | gEVAR/E | Day 0 | 42 | 2 | 3.84 | 7.70 | 0.59 | 1.17 | 1.49 | 3.61 | 49.50 |
| | | | Month 1 | 42 | 2 | 9.78 | 9.70 | 0.94 | 3.82 | 6.44 | 12.74 | 49.37 |
| | | | Month 2 | 42 | 2 | 9.89 | 8.26 | 0.79 | 3.88 | 8.90 | 13.30 | 43.68 |
| | | | Month 3 | 43 | 1 | 34.03 | 25.88 | 3.01 | 14.92 | 30.69 | 45.24 | 117.38 |
| | | gEVAR/Y | Day 0 | 10 | 0 | 5.78 | 5.63 | 1.85 | 2.42 | 3.26 | 7.53 | 20.39 |
| | | | Month 1 | 10 | 0 | 19.80 | 16.75 | 5.89 | 9.80 | 13.77 | 18.38 | 51.54 |
| | | | Month 2 | 9 | 1 | 24.38 | 14.38 | 8.00 | 9.03 | 22.40 | 38.49 | 44.11 |
| | | | Month 3 | 10 | 0 | 33.17 | 19.70 | 6.72 | 11.15 | 32.50 | 52.45 | 58.00 |
| 4 µg/ml | gE | VAR/E | Day 0 | 44 | 1 | 2.19 | 2.64 | 0.67 | 1.14 | 1.37 | 2.30 | 14.80 |
| | | | Month 1 | 44 | 1 | 3.47 | 3.55 | 0.26 | 1.31 | 1.87 | 4.70 | 17.20 |
| | | | Month 2 | 43 | 2 | 2.86 | 2.94 | 0.62 | 1.10 | 1.52 | 3.55 | 15.40 |
| | | | Month 3 | 43 | 2 | 3.30 | 2.69 | 0.47 | 1.36 | 2.36 | 4.20 | 11.36 |
| | | gE/E | Day 0 | 43 | 2 | 2.74 | 4.00 | 0.29 | 1.04 | 1.37 | 3.24 | 25.55 |
| | | | Month 1 | 42 | 3 | 10.08 | 12.66 | 0.65 | 2.84 | 4.49 | 14.49 | 67.46 |
| | | | Month 2 | 42 | 3 | 8.07 | 8.23 | 0.87 | 2.88 | 4.02 | 10.16 | 38.39 |
| | | | Month 3 | 42 | 3 | 28.13 | 21.36 | 1.78 | 14.58 | 20.83 | 36.28 | 104.34 |
| | | gE/Y | Day 0 | 10 | 0 | 2.85 | 1.95 | 0.85 | 1.12 | 2.70 | 3.69 | 6.21 |
| | | | Month 1 | 9 | 1 | 14.39 | 15.26 | 0.83 | 5.17 | 9.06 | 13.73 | 49.06 |
| | | | Month 2 | 10 | 0 | 19.81 | 14.60 | 4.71 | 9.75 | 13.64 | 28.99 | 51.20 |
| | | | Month 3 | 10 | 0 | 32.53 | 17.61 | 3.93 | 26.84 | 32.60 | 43.71 | 56.99 |
| | | gEVAR/E | Day 0 | 42 | 2 | 3.30 | 6.69 | 0.66 | 1.11 | 1.56 | 2.64 | 43.49 |
| | | | Month 1 | 42 | 2 | 7.40 | 9.69 | 0.88 | 2.33 | 4.80 | 8.10 | 58.76 |

TABLE L.1-continued

Descriptive statistics on the Stimulating Index for
lymphoproliferation (ATP cohort for immunogenicity)

| Concentration | Stimulating Antigen | Group | Timing | N | N miss. | Mean | SD | Min | Q1 | Median | Q3 | Max |
|---|---|---|---|---|---|---|---|---|---|---|---|---|
| | | | Month 2 | 42 | 2 | 6.94 | 6.77 | 0.91 | 2.25 | 5.37 | 9.28 | 40.34 |
| | | | Month 3 | 43 | 1 | 30.45 | 25.08 | 4.02 | 9.63 | 24.42 | 43.85 | 110.76 |
| | | gEVAR/Y | Day 0 | 10 | 0 | 4.15 | 3.07 | 1.31 | 1.91 | 2.85 | 5.65 | 10.99 |
| | | | Month 1 | 10 | 0 | 15.96 | 10.92 | 3.86 | 10.96 | 13.00 | 15.98 | 40.77 |
| | | | Month 2 | 9 | 1 | 21.57 | 14.61 | 3.08 | 8.91 | 22.20 | 26.82 | 47.30 |
| | | | Month 3 | 10 | 0 | 30.11 | 19.58 | 3.58 | 8.61 | 30.13 | 51.66 | 54.23 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years
N = number of subjects with available results
N miss. = number of subjects with missing results
SD = Standard Deviation
Min, Max = Minimum, Maximum
Q1, Q3 = First, Third quartile

TABLE L.2

Lymphoproliferation: Geometric Mean of stimulation index
(ATP cohort for immunogenicity)

| Concentration | Stimulating Antigen | Group | Timing | N | N miss. | GMT | Min | Max |
|---|---|---|---|---|---|---|---|---|
| 0.1 CPAU/ml | VZV | VAR/E | Day 0 | 44 | 1 | 15.69 | 1.06 | 221.53 |
| | | | Month 1 | 44 | 1 | 19.10 | 0.94 | 92.16 |
| | | | Month 2 | 43 | 2 | 22.62 | 5.61 | 95.32 |
| | | | Month 3 | 43 | 2 | 22.77 | 6.72 | 124.46 |
| | | gE/E | Day 0 | 43 | 2 | 15.38 | 1.21 | 91.05 |
| | | | Month 1 | 42 | 3 | 20.48 | 2.55 | 107.18 |
| | | | Month 2 | 42 | 3 | 21.23 | 1.62 | 138.04 |
| | | | Month 3 | 42 | 3 | 22.60 | 2.16 | 87.26 |
| | | gE/Y | Day 0 | 10 | 0 | 33.69 | 9.36 | 67.30 |
| | | | Month 1 | 9 | 1 | 33.79 | 5.42 | 102.82 |
| | | | Month 2 | 10 | 0 | 39.66 | 12.35 | 108.21 |
| | | | Month 3 | 10 | 0 | 40.08 | 8.87 | 82.49 |
| | | gEVAR/E | Day 0 | 42 | 2 | 12.94 | 1.35 | 136.88 |
| | | | Month 1 | 42 | 2 | 22.67 | 3.31 | 68.92 |
| | | | Month 2 | 42 | 2 | 22.03 | 1.97 | 96.33 |
| | | | Month 3 | 43 | 1 | 28.62 | 4.45 | 142.50 |
| | | gEVAR/Y | Day 0 | 10 | 0 | 46.28 | 29.45 | 106.72 |
| | | | Month 1 | 10 | 0 | 46.68 | 18.42 | 105.66 |
| | | | Month 2 | 9 | 1 | 44.87 | 11.07 | 82.69 |
| | | | Month 3 | 10 | 0 | 42.48 | 16.19 | 77.75 |
| 1 CPAU/ml | VZV | VAR/E | Day 0 | 44 | 1 | 22.89 | 0.81 | 143.45 |
| | | | Month 1 | 44 | 1 | 33.48 | 1.58 | 122.15 |
| | | | Month 2 | 43 | 2 | 34.44 | 12.27 | 586.25 |
| | | | Month 3 | 43 | 2 | 29.76 | 8.56 | 116.31 |
| | | gE/E | Day 0 | 43 | 2 | 24.61 | 4.59 | 139.71 |
| | | | Month 1 | 42 | 3 | 27.63 | 1.54 | 110.93 |
| | | | Month 2 | 42 | 3 | 29.72 | 1.46 | 107.68 |
| | | | Month 3 | 42 | 3 | 31.84 | 8.37 | 85.04 |
| | | gE/Y | Day 0 | 10 | 0 | 37.53 | 9.30 | 87.99 |
| | | | Month 1 | 9 | 1 | 39.83 | 6.31 | 132.58 |
| | | | Month 2 | 10 | 0 | 49.89 | 16.73 | 88.07 |
| | | | Month 3 | 10 | 0 | 46.60 | 13.72 | 143.80 |
| | | gEVAR/E | Day 0 | 42 | 2 | 20.59 | 1.20 | 146.46 |
| | | | Month 1 | 42 | 2 | 32.04 | 3.01 | 108.05 |
| | | | Month 2 | 42 | 2 | 33.52 | 7.67 | 126.34 |
| | | | Month 3 | 43 | 1 | 35.94 | 3.98 | 151.51 |
| | | gEVAR/Y | Day 0 | 10 | 0 | 53.44 | 27.66 | 138.10 |
| | | | Month 1 | 10 | 0 | 57.76 | 21.95 | 145.08 |
| | | | Month 2 | 9 | 1 | 60.28 | 28.77 | 128.29 |
| | | | Month 3 | 10 | 0 | 58.44 | 18.29 | 118.24 |
| 20 μg/ml | gE | VAR/E | Day 0 | 44 | 1 | 2.05 | 0.77 | 14.30 |
| | | | Month 1 | 44 | 1 | 2.41 | 0.57 | 20.96 |
| | | | Month 2 | 43 | 2 | 2.75 | 0.86 | 30.33 |
| | | | Month 3 | 43 | 2 | 2.71 | 0.60 | 14.05 |
| | | gE/E | Day 0 | 43 | 2 | 2.15 | 0.78 | 37.21 |
| | | | Month 1 | 42 | 3 | 8.48 | 0.76 | 45.95 |

TABLE L.2-continued

Lymphoproliferation: Geometric Mean of stimulation index
(ATP cohort for immunogenicity)

| Concentration | Stimulating Antigen | Group | Timing | N | N miss. | GMT | Min | Max |
|---|---|---|---|---|---|---|---|---|
| | | | Month 2 | 42 | 3 | 7.76 | 0.93 | 51.08 |
| | | | Month 3 | 42 | 3 | 23.31 | 1.97 | 101.46 |
| | | gE/Y | Day 0 | 10 | 0 | 2.36 | 1.01 | 4.88 |
| | | | Month 1 | 9 | 1 | 12.71 | 2.17 | 43.15 |
| | | | Month 2 | 10 | 0 | 20.50 | 9.37 | 60.58 |
| | | | Month 3 | 10 | 0 | 30.14 | 4.72 | 76.56 |
| | | gEVAR/E | Day 0 | 42 | 2 | 2.08 | 0.59 | 49.50 |
| | | | Month 1 | 42 | 2 | 6.68 | 0.94 | 49.37 |
| | | | Month 2 | 42 | 2 | 7.09 | 0.79 | 43.68 |
| | | | Month 3 | 43 | 1 | 25.27 | 3.01 | 117.38 |
| | | gEVAR/Y | Day 0 | 10 | 0 | 4.29 | 1.85 | 20.39 |
| | | | Month 1 | 10 | 0 | 15.21 | 5.89 | 51.54 |
| | | | Month 2 | 9 | 1 | 20.06 | 8.00 | 44.11 |
| | | | Month 3 | 10 | 0 | 26.11 | 6.72 | 58.00 |
| 4 µg/ml | gE | VAR/E | Day 0 | 44 | 1 | 1.63 | 0.67 | 14.80 |
| | | | Month 1 | 44 | 1 | 2.37 | 0.26 | 17.20 |
| | | | Month 2 | 43 | 2 | 2.03 | 0.62 | 15.40 |
| | | | Month 3 | 43 | 2 | 2.48 | 0.47 | 11.36 |
| | | gE/E | Day 0 | 43 | 2 | 1.75 | 0.29 | 25.55 |
| | | | Month 1 | 42 | 3 | 5.74 | 0.65 | 67.46 |
| | | | Month 2 | 42 | 3 | 5.36 | 0.87 | 38.39 |
| | | | Month 3 | 42 | 3 | 20.95 | 1.78 | 104.34 |
| | | gE/Y | Day 0 | 10 | 0 | 2.26 | 0.85 | 6.21 |
| | | | Month 1 | 9 | 1 | 8.55 | 0.83 | 49.06 |
| | | | Month 2 | 10 | 0 | 15.55 | 4.71 | 51.20 |
| | | | Month 3 | 10 | 0 | 25.27 | 3.93 | 56.99 |
| | | gEVAR/E | Day 0 | 42 | 2 | 1.94 | 0.66 | 43.49 |
| | | | Month 1 | 42 | 2 | 4.64 | 0.88 | 58.76 |
| | | | Month 2 | 42 | 2 | 4.90 | 0.91 | 40.34 |
| | | | Month 3 | 43 | 1 | 21.47 | 4.02 | 110.76 |
| | | gEVAR/Y | Day 0 | 10 | 0 | 3.31 | 1.31 | 10.99 |
| | | | Month 1 | 10 | 0 | 13.14 | 3.86 | 40.77 |
| | | | Month 2 | 9 | 1 | 16.14 | 3.08 | 47.30 |
| | | | Month 3 | 10 | 0 | 22.09 | 3.58 | 54.23 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years
N = number of subjects with available results
N miss. = number of subjects with missing results
GMT = Geometric Mean Titer
LL, UL = Lower, Upper Limit of 95% confidence interval
Min, Max = Minimum, Maximum

TABLE L.3

Lymphoproliferation: Inferential statistics on Stimulating Index
(ATP cohort for immunogenicity)

| Groups compared | Concentration | Stimulating Antigen | Timing | P-value Kruskal-Wallis |
|---|---|---|---|---|
| gE\Y and gEVAR\Y | 0.1 CPAU/ml | VZV | Day 0 | 0.1509 |
| | | | Month 1 | 0.3272 |
| | | | Month 2 | 0.6242 |
| | | | Month 3 | 0.8206 |
| | 1 CPAU/ml | VZV | Day 0 | 0.3643 |
| | | | Month 1 | 0.3691 |
| | | | Month 2 | 0.5676 |
| | | | Month 3 | 0.3643 |
| | 20 µg/ml | gE | Day 0 | 0.0963 |
| | | | Month 1 | 0.7440 |
| | | | Month 2 | 0.8065 |
| | | | Month 3 | 0.7624 |
| | 4 µg/ml | gE | Day 0 | 0.2899 |
| | | | Month 1 | 0.3691 |
| | | | Month 2 | 0.9349 |
| | | | Month 3 | 0.7624 |

TABLE L.3-continued

Lymphoproliferation: Inferential statistics on Stimulating Index
(ATP cohort for immunogenicity)

| Groups compared | Concentration | Stimulating Antigen | Timing | P-value Kruskal-Wallis |
|---|---|---|---|---|
| VAR\E and gE\E | 0.1 CPAU/ml | VZV | Day 0 | 0.9594 |
| | | | Month 1 | 0.9037 |
| | | | Month 2 | 0.7317 |
| | | | Month 3 | 0.6226 |
| | 1 CPAU/ml | VZV | Day 0 | 0.6899 |
| | | | Month 1 | 0.1062 |
| | | | Month 2 | 0.5041 |
| | | | Month 3 | 0.4657 |
| | 20 µg/ml | gE | Day 0 | 0.9526 |
| | | | Month 1 | 0.0000 |
| | | | Month 2 | 0.0000 |
| | | | Month 3 | 0.0000 |
| | 4 µg/ml | gE | Day 0 | 0.7342 |
| | | | Month 1 | 0.0002 |
| | | | Month 2 | 0.0000 |
| | | | Month 3 | 0.0000 |

TABLE L.3-continued

Lymphoproliferation: Inferential statistics on Stimulating Index (ATP cohort for immunogenicity)

| Groups compared | Concentration | Stimulating Antigen | Timing | P-value Kruskal-Wallis |
|---|---|---|---|---|
| gE\E and gEVAR\E | 0.1 CPAU/ml | VzAg | Day 0 | 0.3794 |
| | | | Month 1 | 0.5489 |
| | | | Month 2 | 0.6939 |
| | | | Month 3 | 0.1903 |
| | 1 CPAU/ml | VzAg | Day 0 | 0.5097 |
| | | | Month 1 | 0.2412 |
| | | | Month 2 | 0.3855 |
| | | | Month 3 | 0.3653 |
| | 20 µg/ml | gE | Day 0 | 0.6226 |
| | | | Month 1 | 0.1375 |
| | | | Month 2 | 0.6164 |
| | | | Month 3 | 0.5737 |
| | 4 µg/ml | gE | Day 0 | 0.6226 |
| | | | Month 1 | 0.4524 |
| | | | Month 2 | 0.8161 |
| | | | Month 3 | 0.9160 |
| VAR\E and gEVAR\E | 0.1 CPAU/ml | VzAg | Day 0 | 0.5059 |
| | | | Month 1 | 0.5922 |
| | | | Month 2 | 0.8812 |
| | | | Month 3 | 0.0913 |
| | 1 CPAU/ml | VzAg | Day 0 | 0.2688 |
| | | | Month 1 | 0.5803 |
| | | | Month 2 | 0.7450 |
| | | | Month 3 | 0.1253 |
| | 20 µg/ml | gE | Day 0 | 0.7690 |
| | | | Month 1 | 0.0000 |
| | | | Month 2 | 0.0000 |
| | | | Month 3 | 0.0000 |
| | 4 µg/ml | gE | Day 0 | 0.3553 |
| | | | Month 1 | 0.0016 |
| | | | Month 2 | 0.0000 |
| | | | Month 3 | 0.0000 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years

TABLE L.4

Lymphoproliferation: Fold increase in Geometric Mean (GMR) (ATP cohort for immunogenicity)

| Concentration | Stimulating Antigen | Group | Ratio POST/PRE | N | N miss. | GMR | LL | UL | Min | Max |
|---|---|---|---|---|---|---|---|---|---|---|
| 0.1 CPAU/ml | VZV | VAR/E | Month 1/Month 0 | 43 | 2 | 1.54 | 1.01 | 2.34 | 0.04 | 27.05 |
| | | | Month 2/Month 0 | 42 | 3 | 1.65 | 1.05 | 2.58 | 0.09 | 52.56 |
| | | | Month 3/Month 0 | 42 | 3 | 2.04 | 1.39 | 2.99 | 0.29 | 48.92 |
| | | gE/E | Month 1/Month 0 | 41 | 4 | 1.39 | 1.01 | 1.92 | 0.15 | 18.32 |
| | | | Month 2/Month 0 | 41 | 4 | 1.42 | 0.94 | 2.12 | 0.02 | 20.08 |
| | | | Month 3/Month 0 | 41 | 4 | 1.86 | 1.38 | 2.52 | 0.13 | 14.83 |
| | | gE/Y | Month 1/Month 0 | 9 | 1 | 0.68 | 0.28 | 1.61 | 0.05 | 1.53 |
| | | | Month 2/Month 0 | 10 | 0 | 1.01 | 0.73 | 1.40 | 0.44 | 1.72 |
| | | | Month 3/Month 0 | 10 | 0 | 1.16 | 0.88 | 1.53 | 0.61 | 2.17 |
| | | gEVAR/E | Month 1/Month 0 | 40 | 4 | 2.10 | 1.45 | 3.04 | 0.13 | 31.67 |
| | | | Month 2/Month 0 | 40 | 4 | 2.06 | 1.36 | 3.11 | 0.06 | 58.19 |
| | | | Month 3/Month 0 | 41 | 3 | 3.22 | 2.28 | 4.54 | 0.86 | 82.33 |
| | | gEVAR/Y | Month 1/Month 0 | 10 | 0 | 0.87 | 0.63 | 1.20 | 0.34 | 1.44 |
| | | | Month 2/Month 0 | 9 | 1 | 0.87 | 0.52 | 1.43 | 0.18 | 1.37 |
| | | | Month 3/Month 0 | 10 | 0 | 0.64 | 0.37 | 1.11 | 0.12 | 1.06 |
| 1 CPAU/ml | VZV | VAR/E | Month 1/Month 0 | 43 | 2 | 1.73 | 1.17 | 2.56 | 0.06 | 86.17 |
| | | | Month 2/Month 0 | 42 | 3 | 1.63 | 1.06 | 2.51 | 0.08 | 124.71 |
| | | | Month 3/Month 0 | 42 | 3 | 1.79 | 1.24 | 2.59 | 0.47 | 70.57 |
| | | gE/E | Month 1/Month 0 | 41 | 4 | 1.18 | 0.90 | 1.53 | 0.05 | 13.44 |
| | | | Month 2/Month 0 | 41 | 4 | 1.16 | 0.82 | 1.64 | 0.01 | 18.94 |
| | | | Month 3/Month 0 | 41 | 4 | 1.64 | 1.23 | 2.18 | 0.09 | 19.91 |
| | | gE/Y | Month 1/Month 0 | 9 | 1 | 0.75 | 0.32 | 1.73 | 0.05 | 1.38 |
| | | | Month 2/Month 0 | 10 | 0 | 1.14 | 0.91 | 1.42 | 0.78 | 1.81 |
| | | | Month 3/Month 0 | 10 | 0 | 1.21 | 1.01 | 1.46 | 0.83 | 1.69 |
| | | gEVAR/E | Month 1/Month 0 | 40 | 4 | 1.85 | 1.40 | 2.43 | 0.46 | 15.65 |
| | | | Month 2/Month 0 | 40 | 4 | 1.82 | 1.33 | 2.49 | 0.13 | 48.63 |
| | | | Month 3/Month 0 | 41 | 3 | 2.52 | 1.88 | 3.38 | 0.88 | 80.53 |
| | | gEVAR/Y | Month 1/Month 0 | 10 | 0 | 0.93 | 0.75 | 1.17 | 0.48 | 1.33 |
| | | | Month 2/Month 0 | 9 | 1 | 0.98 | 0.79 | 1.22 | 0.60 | 1.26 |
| | | | Month 3/Month 0 | 10 | 0 | 0.76 | 0.46 | 1.26 | 0.15 | 1.29 |
| 20 µg/ml | gE | VAR/E | Month 1/Month 0 | 43 | 2 | 1.35 | 1.04 | 1.75 | 0.16 | 11.02 |
| | | | Month 2/Month 0 | 42 | 3 | 1.46 | 1.10 | 1.94 | 0.27 | 20.90 |
| | | | Month 3/Month 0 | 42 | 3 | 1.90 | 1.42 | 2.54 | 0.39 | 26.66 |
| | | gE/E | Month 1/Month 0 | 41 | 4 | 4.26 | 2.98 | 6.07 | 0.22 | 74.67 |
| | | | Month 2/Month 0 | 41 | 4 | 3.62 | 2.41 | 5.46 | 0.05 | 28.79 |
| | | | Month 3/Month 0 | 41 | 4 | 13.90 | 9.16 | 21.07 | 0.31 | 205.73 |
| | | gE/Y | Month 1/Month 0 | 9 | 1 | 3.84 | 1.17 | 12.65 | 0.11 | 12.75 |
| | | | Month 2/Month 0 | 10 | 0 | 7.45 | 5.15 | 10.77 | 3.91 | 15.23 |
| | | | Month 3/Month 0 | 10 | 0 | 12.50 | 7.41 | 21.10 | 3.14 | 37.77 |
| | | gEVAR/E | Month 1/Month 0 | 40 | 4 | 3.89 | 2.90 | 5.22 | 0.95 | 28.69 |
| | | | Month 2/Month 0 | 40 | 4 | 3.86 | 2.54 | 5.87 | 0.03 | 38.27 |
| | | | Month 3/Month 0 | 41 | 3 | 17.92 | 12.65 | 25.38 | 1.38 | 172.56 |

TABLE L.4-continued

Lymphoproliferation: Fold increase in Geometric Mean (GMR)
(ATP cohort for immunogenicity)

| Concentration | Stimulating Antigen | Group | Ratio POST/PRE | N | N miss. | GMR | LL | UL | Min | Max |
|---|---|---|---|---|---|---|---|---|---|---|
| | | gEVAR/Y | Month 1/Month 0 | 10 | 0 | 3.07 | 1.40 | 6.72 | 0.38 | 15.77 |
| | | | Month 2/Month 0 | 9 | 1 | 4.09 | 2.10 | 7.98 | 1.85 | 15.42 |
| | | | Month 3/Month 0 | 10 | 0 | 4.25 | 1.60 | 11.30 | 0.28 | 15.60 |
| 4 µg/ml | gE | VAR/E | Month 1/Month 0 | 43 | 2 | 1.75 | 1.36 | 2.25 | 0.08 | 8.82 |
| | | | Month 2/Month 0 | 42 | 3 | 1.40 | 1.03 | 1.89 | 0.12 | 36.27 |
| | | | Month 3/Month 0 | 42 | 3 | 2.17 | 1.60 | 2.95 | 0.51 | 66.05 |
| | | gE/E | Month 1/Month 0 | 41 | 4 | 3.32 | 2.34 | 4.69 | 0.31 | 36.29 |
| | | | Month 2/Month 0 | 41 | 4 | 3.10 | 2.02 | 4.76 | 0.04 | 25.22 |
| | | | Month 3/Month 0 | 41 | 4 | 14.32 | 9.39 | 21.82 | 0.26 | 110.97 |
| | | gE/Y | Month 1/Month 0 | 9 | 1 | 2.88 | 0.75 | 11.06 | 0.07 | 21.03 |
| | | | Month 2/Month 0 | 10 | 0 | 5.91 | 3.32 | 10.52 | 2.49 | 31.74 |
| | | | Month 3/Month 0 | 10 | 0 | 10.95 | 5.62 | 21.37 | 3.07 | 48.19 |
| | | gEVAR/E | Month 1/Month 0 | 40 | 4 | 2.90 | 2.26 | 3.71 | 0.54 | 22.40 |
| | | | Month 2/Month 0 | 40 | 4 | 2.96 | 2.08 | 4.21 | 0.10 | 35.98 |
| | | | Month 3/Month 0 | 41 | 3 | 16.40 | 11.62 | 23.15 | 1.51 | 237.09 |
| | | gEVAR/Y | Month 1/Month 0 | 10 | 0 | 3.43 | 1.61 | 7.32 | 0.41 | 16.60 |
| | | | Month 2/Month 0 | 9 | 1 | 3.98 | 1.76 | 9.01 | 0.91 | 31.37 |
| | | | Month 3/Month 0 | 10 | 0 | 4.65 | 1.72 | 12.60 | 0.30 | 19.48 | gE/Y = gE-AS1/18-30 years
gEVAR/Y = gE-AS1 + Varilrix/18-30 years
VAR/E = Varilrix/50-70 years
gE/E = gE-AS1/50-70 years
gEVAR/E = gE-AS1 + Varilrix/50-70 years
N = number of subjects with available results
N miss. = number of subjects with missing results
GMR = Geometric Mean ratio
LL, UL = Lower, Upper Limit of 95% confidence interval for GMR
Min, Max = Minimum, Maximum

CONCLUSIONS

The gE AS1 vaccine and the concomitant delivery of gE AS1 with the OKA strain both provoke a good immune response in comparison to the response obtained by the OKA strain alone.

What is claimed is:

1. An immunogenic composition consisting essentially of a varicella zoster virus (VZV) gE antigen truncated to remove the carboxy terminal anchor region, which gE is not in the form of a fusion protein, in combination with an adjuvant comprising QS21, 3D MPL, and liposomes comprising cholesterol.

2. A method of increasing cell-mediated immunity in a patient, said method comprising administering to said patient an effective amount of an immunogenic composition comprising varicella-zoster virus (VZV) gE, which gE is not in the form of a fusion protein, and a TH-1 adjuvant comprising QS21, 3D-MPL and liposomes, wherein the cell mediated immunity ameliorates at least one of shingles or post herpetic neuralgia in the patient.

3. The method according to claim 1, wherein the liposomes comprise cholesterol.

4. The method according to claim 1, wherein the 3D-MPL is within a liposome.

5. The method according to claim 1, wherein the gE is a truncate.

6. The method according to claim 5, wherein the gE is a C-terminal truncate.

7. The method according to claim 6, wherein the gE has the amino acid sequence of SEQ ID NO: 1.

8. The method according to claim 1, wherein the immunogenic composition is administered to an individual of at least 50 years of age.

9. The method according to claim 1, wherein the immunogenic composition is administered to an immunocompromised individual.

10. A method of increasing cell-mediated immunity in a patient, said method comprising administering to said patient an effective amount of an immunogenic composition comprising varicella-zoster virus (VZV) gE, which gE is not in the form of a fusion protein and a TH-1 adjuvant comprising QS21, 3D-MPL and liposomes, wherein the cell mediated immunity prevents herpes zoster reactivation in the patient.

11. The method according to claim 10, wherein the liposomes comprise cholesterol.

12. The method according to claim 10, wherein the 3D-MPL is within a liposome.

13. The method according to claim 10, wherein the gE is a truncate.

14. The method according to claim 13, wherein the gE is a C-terminal truncate.

15. The method according to claim 14, wherein the gE has the amino acid sequence of SEQ ID NO: 1.

16. The method according to claim 10, wherein the immunogenic composition is administered to an individual of at least 50 years of age.

17. The method according to claim 10, wherein the immunogenic composition is administered to an immunocompromised individual.

\* \* \* \* \*

```
SEQUENCE LISTING

<160> NUMBER OF SEQ ID NOS: 1

<210> SEQ ID NO 1
<211> LENGTH: 546
<212> TYPE: PRT
<213> ORGANISM: Varicella zoster

<400> SEQUENCE: 1

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
                20                  25                  30

Leu Arg Tyr Asp Asp Phe His Ile Asp Glu Asp Lys Leu Asp Thr Asn
            35                  40                  45

Ser Val Tyr Glu Pro Tyr Tyr His Ser Asp His Ala Glu Ser Ser Trp
        50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110
```

-continued

```
Arg Leu Met Gln Pro Thr Gln Met Ser Ala Gln Glu Asp Leu Gly Asp
        115                 120                 125
Asp Thr Gly Ile His Val Ile Pro Thr Leu Asn Gly Asp Asp Arg His
    130                 135                 140
Lys Ile Val Asn Val Asp Gln Arg Gln Tyr Gly Asp Val Phe Lys Gly
145                 150                 155                 160
Asp Leu Asn Pro Lys Pro Gln Gly Gln Arg Leu Ile Glu Val Ser Val
                165                 170                 175
Glu Glu Asn His Pro Phe Thr Leu Arg Ala Pro Ile Gln Arg Ile Tyr
            180                 185                 190
Gly Val Arg Tyr Thr Glu Thr Trp Ser Phe Leu Pro Ser Leu Thr Cys
        195                 200                 205
Thr Gly Asp Ala Ala Pro Ala Ile Gln His Ile Cys Leu Lys His Thr
    210                 215                 220
Thr Cys Phe Gln Asp Val Val Asp Val Asp Cys Ala Glu Asn Thr
225                 230                 235                 240
Lys Glu Asp Gln Leu Ala Glu Ile Ser Tyr Arg Phe Gln Gly Lys Lys
                245                 250                 255
Glu Ala Asp Gln Pro Trp Ile Val Val Asn Thr Ser Thr Leu Phe Asp
            260                 265                 270
Glu Leu Glu Leu Asp Pro Pro Glu Ile Glu Pro Gly Val Leu Lys Val
        275                 280                 285
Leu Arg Thr Glu Lys Gln Tyr Leu Gly Val Tyr Ile Trp Asn Met Arg
    290                 295                 300
Gly Ser Asp Gly Thr Ser Thr Tyr Ala Thr Phe Leu Val Thr Trp Lys
305                 310                 315                 320
Gly Asp Glu Lys Thr Arg Asn Pro Thr Pro Ala Val Thr Pro Gln Pro
                325                 330                 335
Arg Gly Ala Glu Phe His Met Trp Asn Tyr His Ser His Val Phe Ser
            340                 345                 350
Val Gly Asp Thr Phe Ser Leu Ala Met His Leu Gln Tyr Lys Ile His
        355                 360                 365
Glu Ala Pro Phe Asp Leu Leu Leu Glu Trp Leu Tyr Val Pro Ile Asp
    370                 375                 380
Pro Thr Cys Gln Pro Met Arg Leu Tyr Ser Thr Cys Leu Tyr His Pro
385                 390                 395                 400
Asn Ala Pro Gln Cys Leu Ser His Met Asn Ser Gly Cys Thr Phe Thr
                405                 410                 415
Ser Pro His Leu Ala Gln Arg Val Ala Ser Thr Val Tyr Gln Asn Cys
            420                 425                 430
Glu His Ala Asp Asn Tyr Thr Ala Tyr Cys Leu Gly Ile Ser His Met
        435                 440                 445
Glu Pro Ser Phe Gly Leu Ile Leu His Asp Gly Thr Thr Leu Lys
    450                 455                 460
Phe Val Asp Thr Pro Glu Ser Leu Ser Gly Leu Tyr Val Phe Val Val
465                 470                 475                 480
Tyr Phe Asn Gly His Val Glu Ala Val Ala Tyr Thr Val Ser Thr
                485                 490                 495
Val Asp His Phe Val Asn Ala Ile Glu Glu Arg Gly Phe Pro Pro Thr
            500                 505                 510
Ala Gly Gln Pro Pro Ala Thr Thr Lys Pro Lys Glu Ile Thr Pro Val
        515                 520                 525
Asn Pro Gly Thr Ser Pro Leu Ile Arg Tyr Ala Ala Trp Thr Gly Gly
    530                 535                 540
```

```
Leu Ala
545
```